(12) United States Patent
Guevremont et al.

(10) Patent No.: US 7,417,225 B2
(45) Date of Patent: Aug. 26, 2008

(54) APPARATUS AND METHOD FOR ADJUSTMENT OF ION SEPARATION RESOLUTION IN FAIMS

(75) Inventors: Roger Guevremont, Ottawa (CA);
Maria Guevremont, Ottawa (CA);
James T. Kapron, Ottawa (CA);
Govindanunny Thekkadath, Ottawa (CA); Greg Skotnicki, Ottawa (CA)

(73) Assignee: Thermo Finnigan LLC, San Jose, CA (US)

( * ) Notice: Subject to any disclaimer, the term of this patent is extended or adjusted under 35 U.S.C. 154(b) by 524 days.

(21) Appl. No.: 11/285,162

(22) Filed: Nov. 23, 2005

(65) Prior Publication Data

US 2006/0151694 A1 Jul. 13, 2006

Related U.S. Application Data

(63) Continuation-in-part of application No. 10/529,307, filed on Mar. 25, 2005, now Pat. No. 7,378,651, which is a continuation-in-part of application No. 11/068,767, filed on Mar. 2, 2005, now Pat. No. 7,223,971, application No. 11/285,162, which is a continuation-in-part of application No. 11/068,764, filed as application No. PCT/CA03/01350 on Sep. 5, 2003, now Pat. No. 7,041,969.

(60) Provisional application No. 60/630,193, filed on Nov. 24, 2004, provisional application No. 60/549,170, filed on Mar. 3, 2004, provisional application No. 60/413,162, filed on Sep. 25, 2002.

(51) Int. Cl.
*B01D 59/44* (2006.01)

(52) U.S. Cl. .............. 250/287; 250/281; 250/288; 250/293

(58) Field of Classification Search .......... 250/281–300
See application file for complete search history.

(56) References Cited

U.S. PATENT DOCUMENTS

| 6,653,627 | B2 |   | 11/2003 | Guevremont et al. |         |
|-----------|----|---|---------|-------------------|---------|
| 6,690,004 | B2 | * | 2/2004  | Miller et al.     | 250/286 |
| 6,727,496 | B2 | * | 4/2004  | Miller et al.     | 250/287 |
| 6,770,875 | B1 |   | 8/2004  | Guevremont et al. |         |
| 6,815,668 | B2 | * | 11/2004 | Miller et al.     | 250/286 |
| 6,815,669 | B1 | * | 11/2004 | Miller et al.     | 250/286 |
| 2001/0030285 | A1 | * | 10/2001 | Miller et al.   | 250/288 |
| 2003/0034449 | A1 | * | 2/2003  | Miller et al.   | 250/287 |
| 2003/0146377 | A1 | * | 8/2003  | Miller et al.   | 250/286 |
| 2004/0124350 | A1 |   | 7/2004  | Miller et al.   |         |

OTHER PUBLICATIONS

Guevremont et al. "Atmospheric Pressure Ion Focusing in a High-Field Asymmetric Waveform Ion Mobility Spectrometer", Review of Scientific Instruments, 1999, vol. 70, No. 2, p. 1370-1383.

* cited by examiner

*Primary Examiner*—Jack I. Berman
*Assistant Examiner*—Andrew Smyth
(74) *Attorney, Agent, or Firm*—Freedman & Associates

(57) ABSTRACT

An apparatus for separating ions includes a FAIMS analyzer region having a first ion inlet for introducing ions into the FAIMS analyzer region. An ion outlet from the FAIMS analyzer region is provided for extracting a subset of the ions that is selectively transmitted along an average ion flow path defined through the FAIMS analyzer region. The apparatus also includes an actuator for controllably varying a length of the average ion flow path through the FAIMS analyzer region.

31 Claims, 49 Drawing Sheets

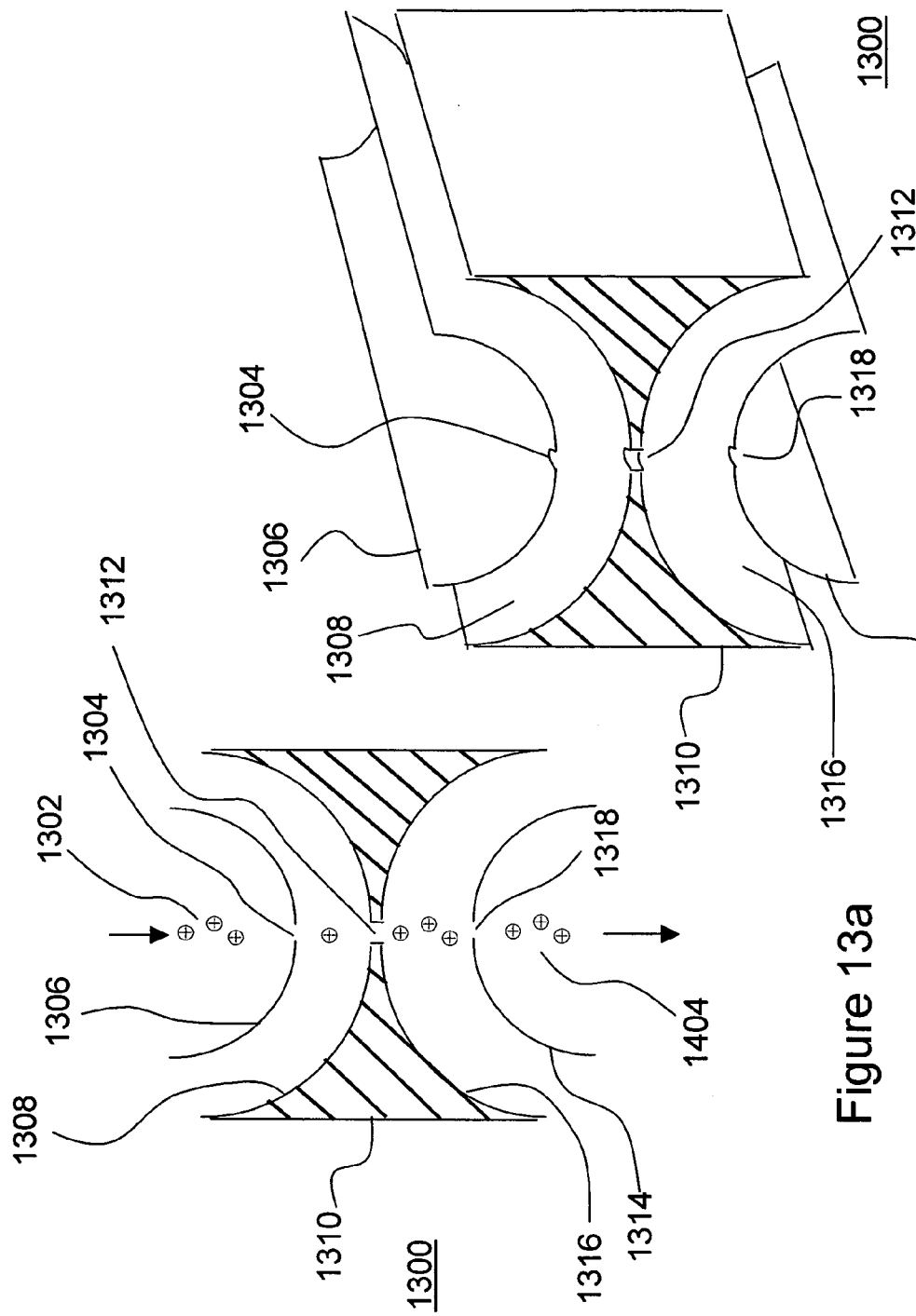

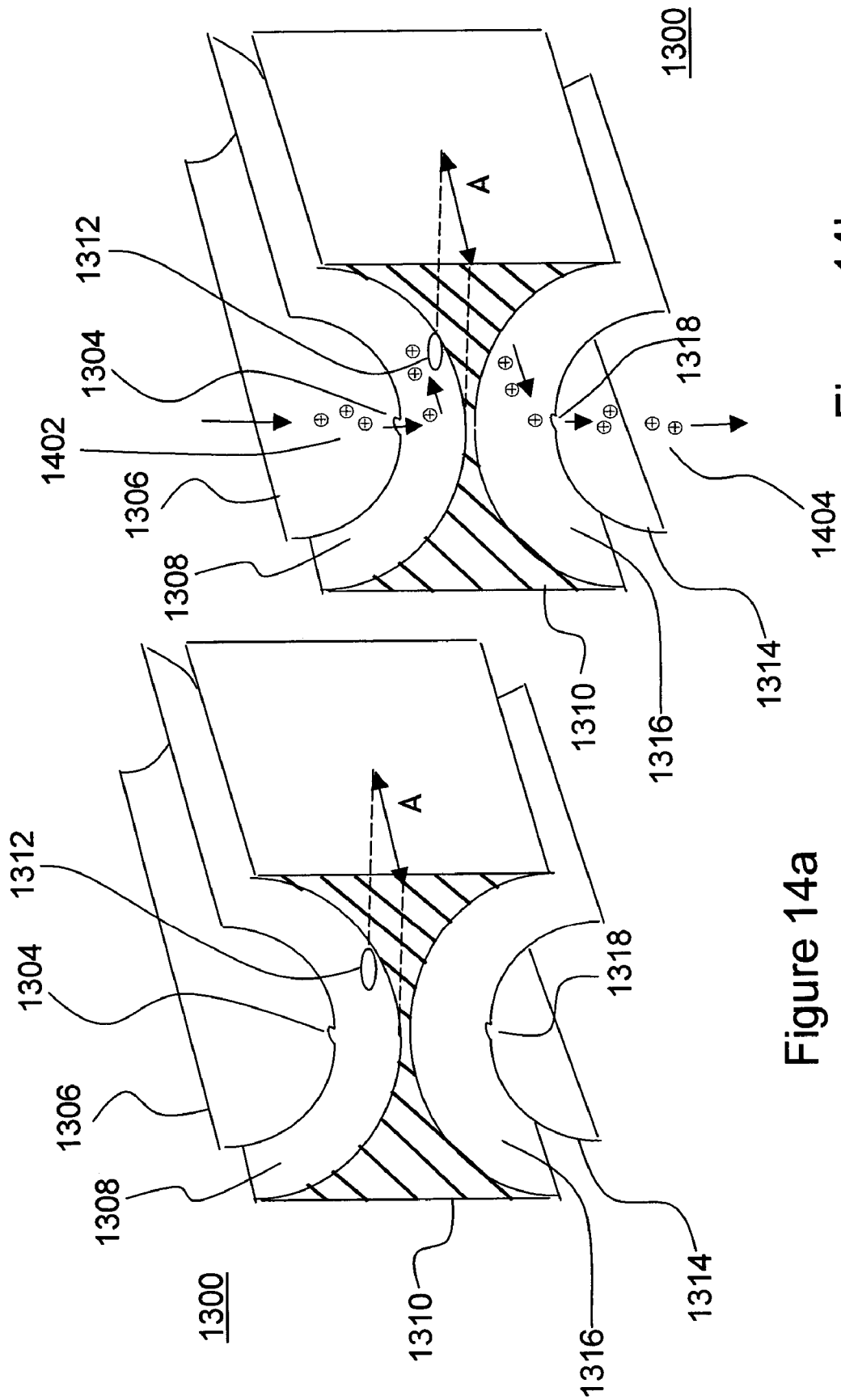

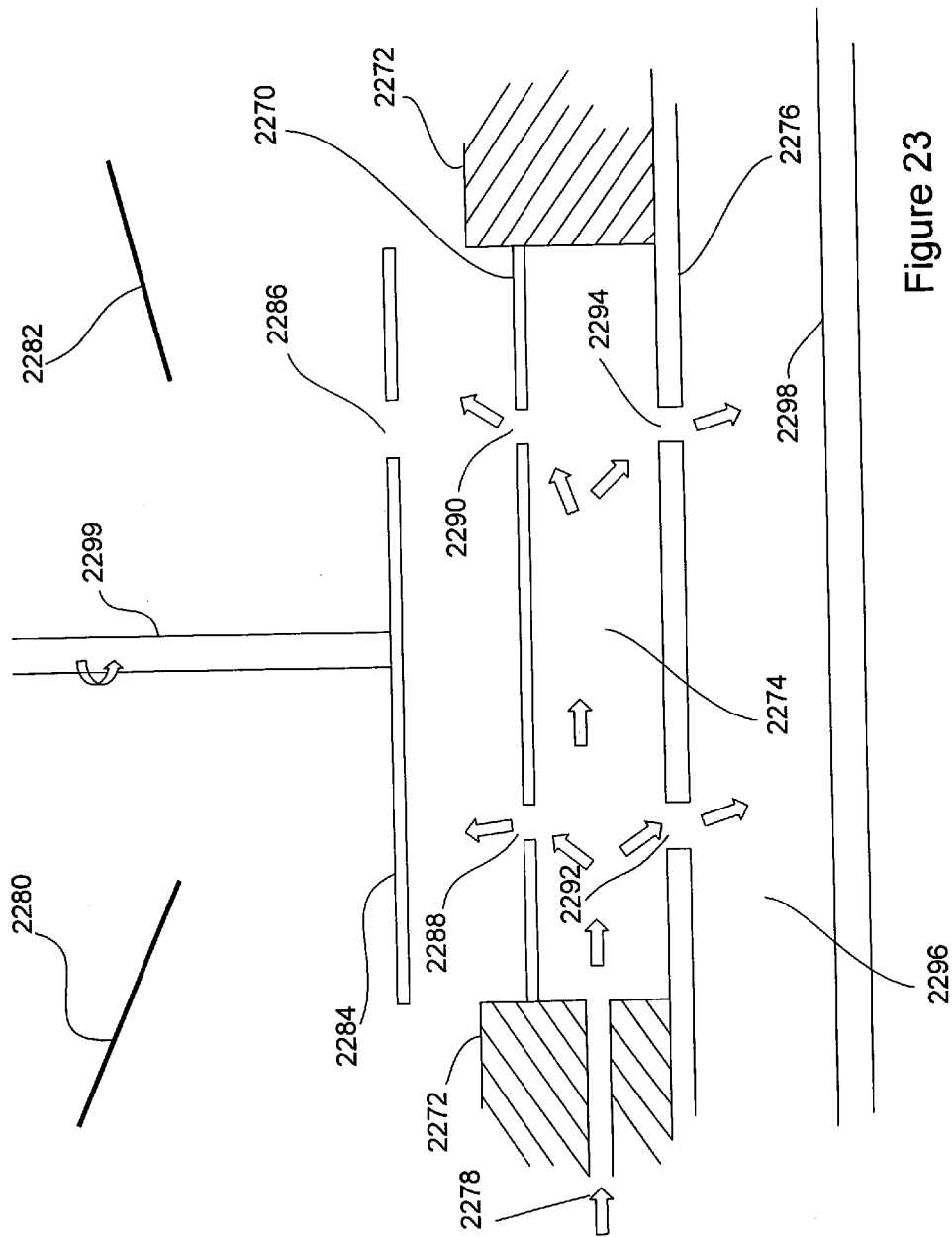

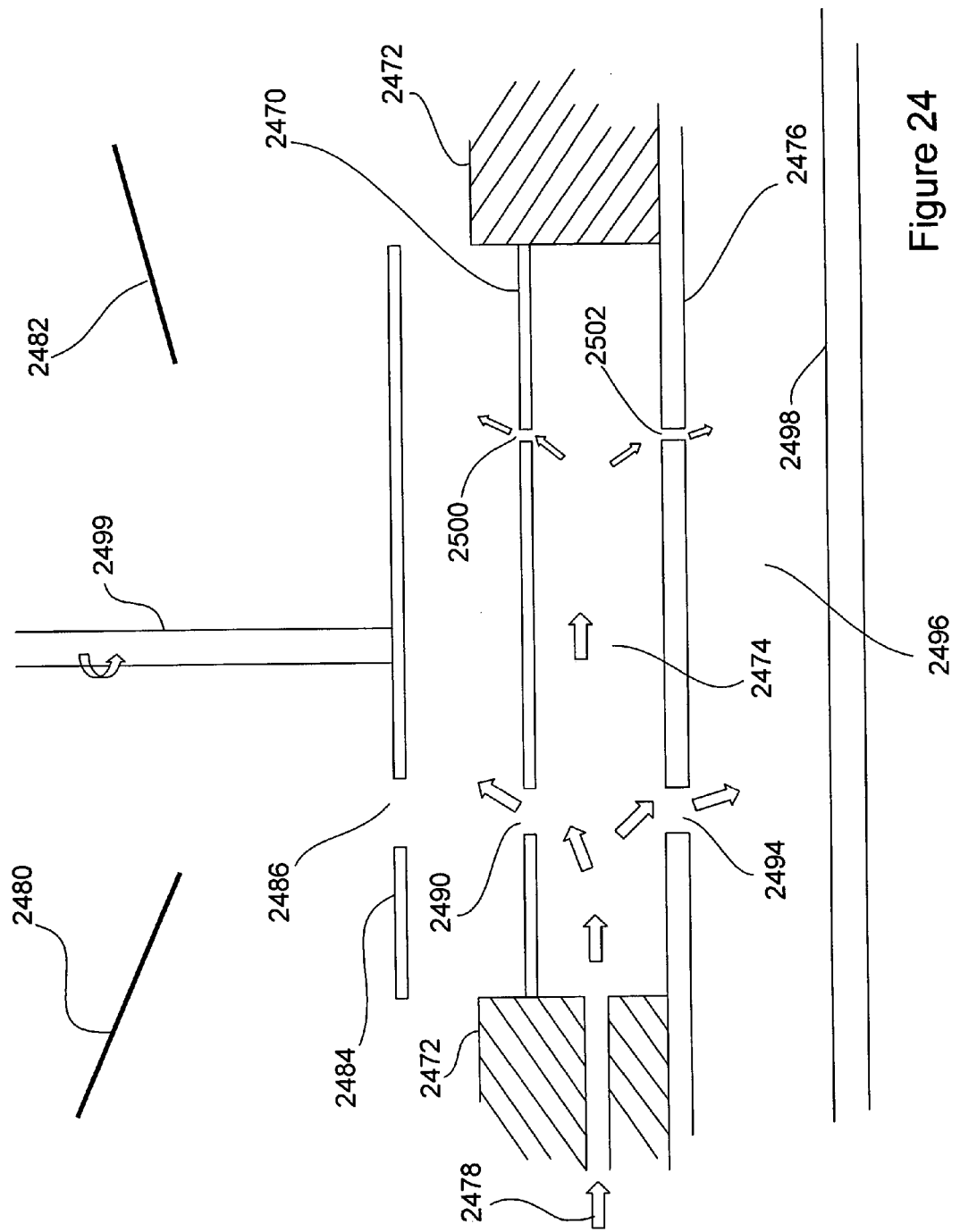

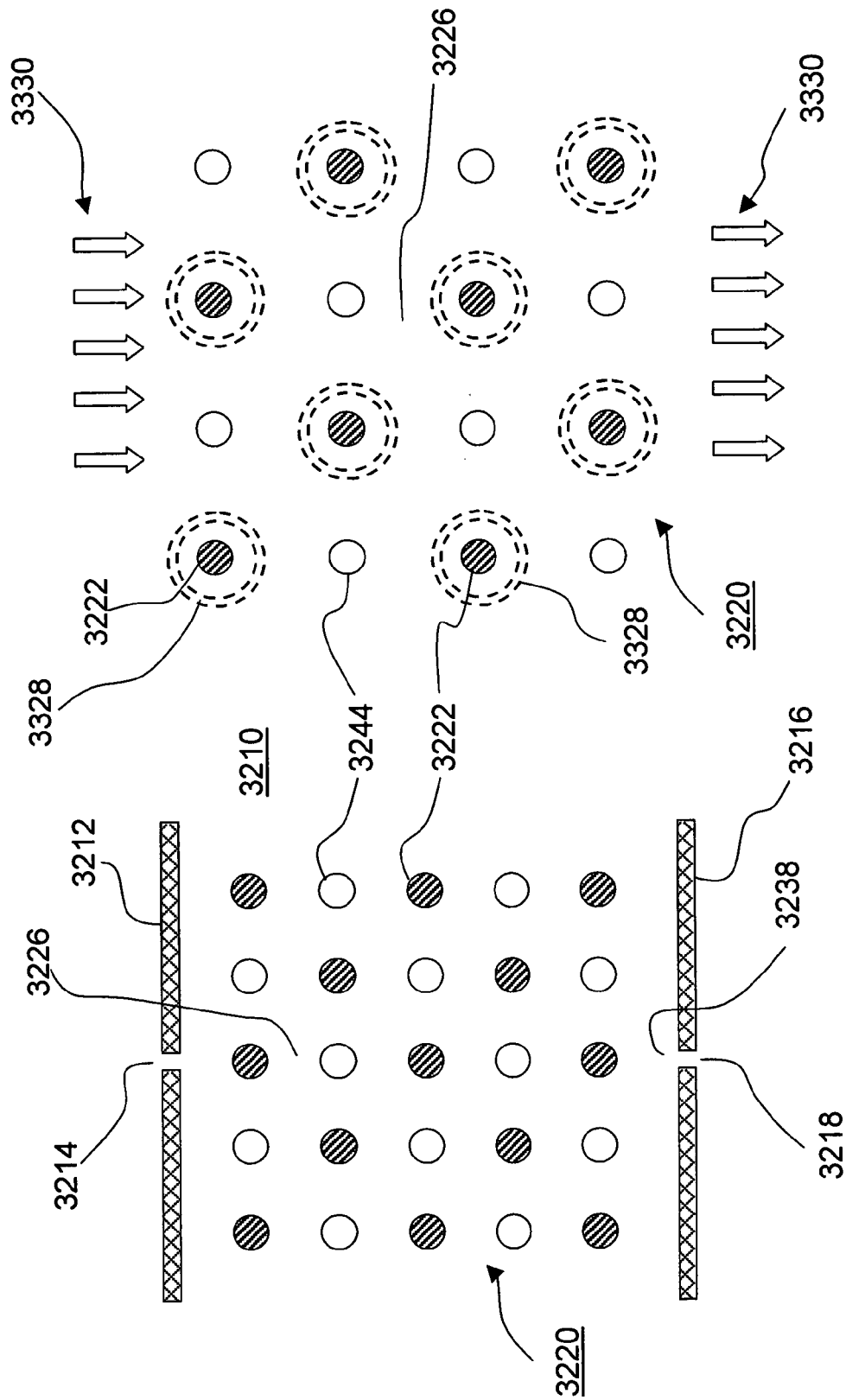

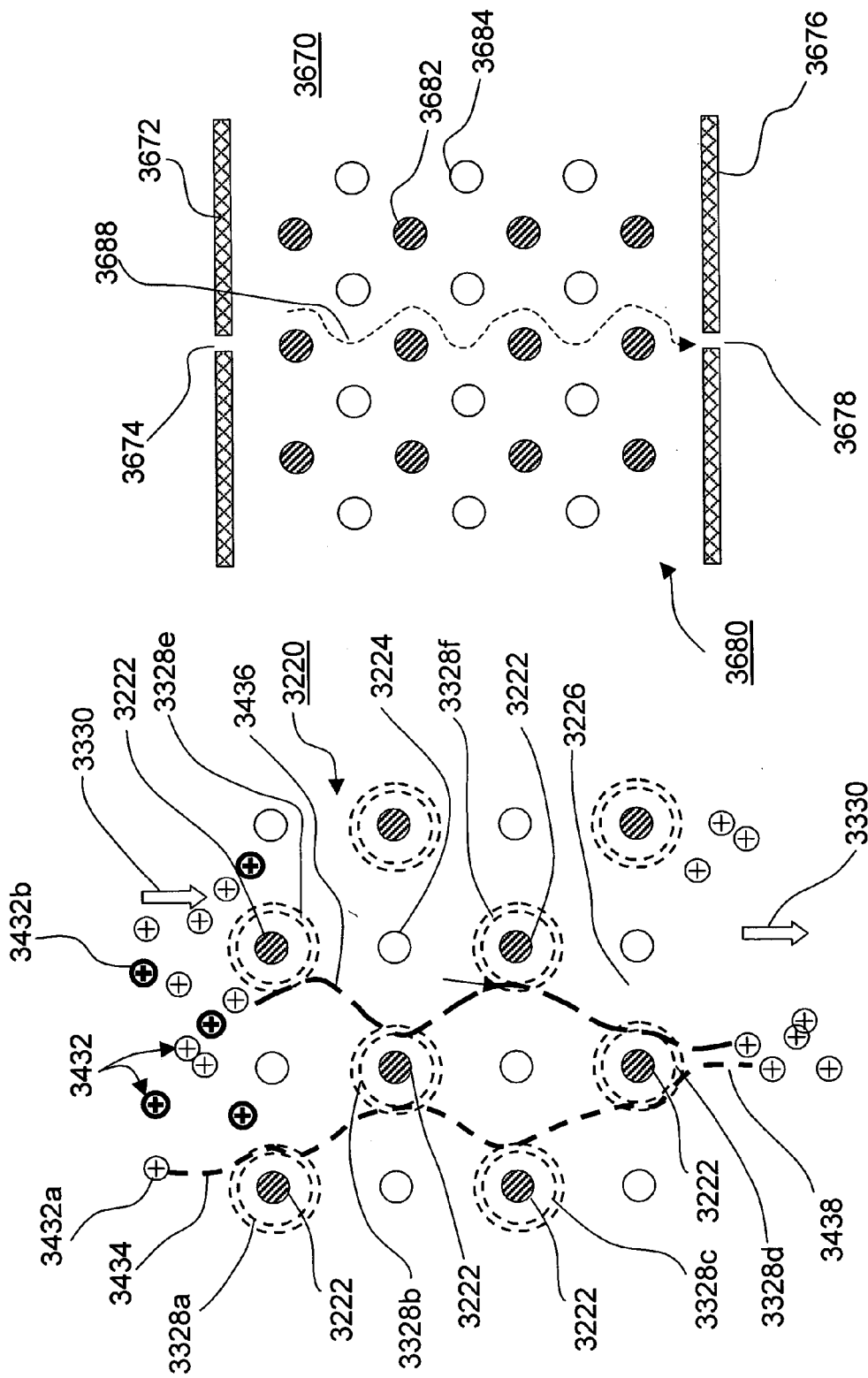

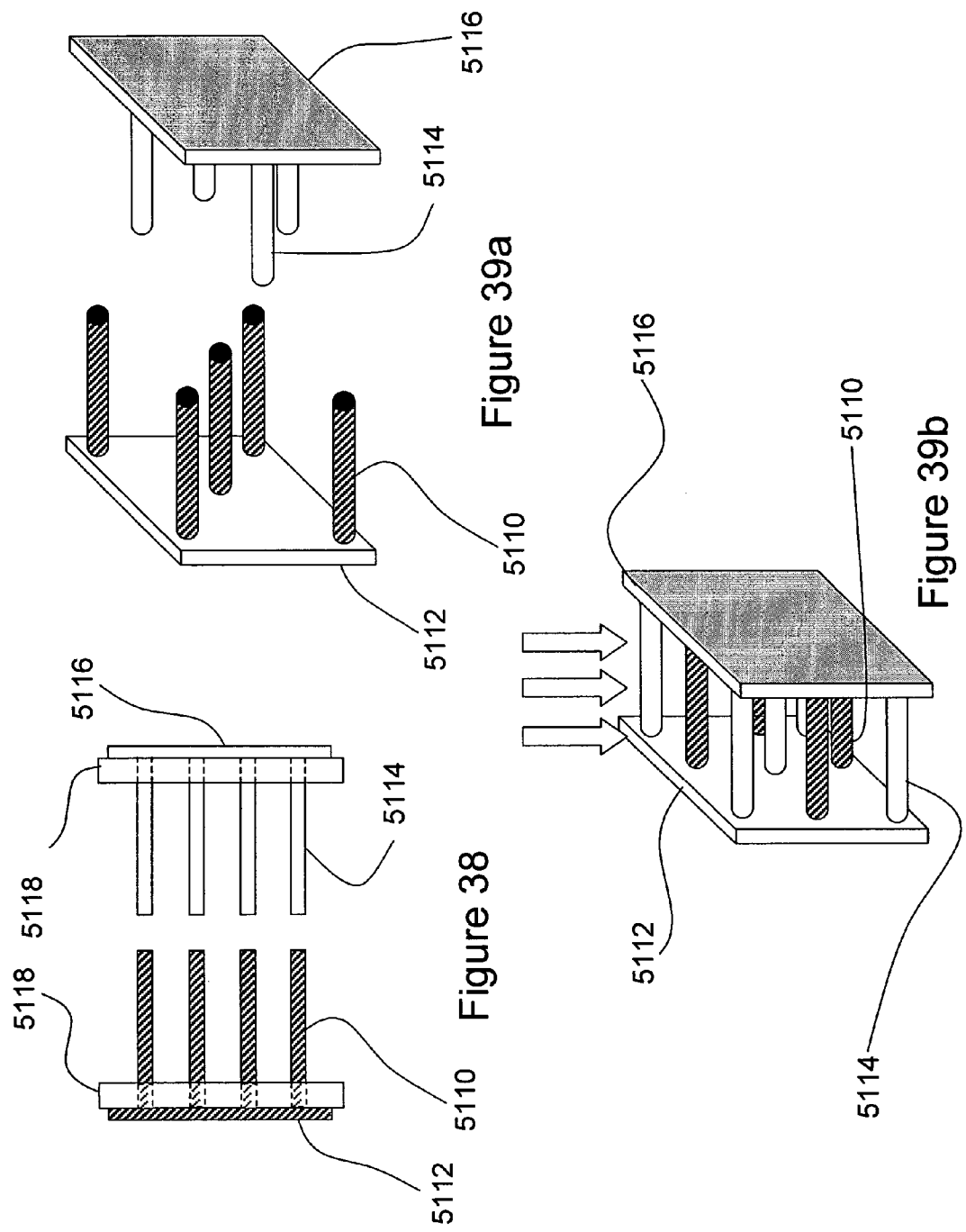

APPARATUS AND METHOD FOR ADJUSTMENT OF ION SEPARATION RESOLUTION IN FAIMS

This application is a continuation-in-part of Ser. No. 11/068,767 filed Mar. 2, 2005, the entire contents of which are incorporated herein by reference. This application is also a continuation-in-part of Ser. No. 11/068,764 filed Mar. 2, 2005, the entire contents of which are incorporated herein by reference. This application is also a continuation-in-part of Ser. No. 10/529,307 filed Mar. 25, 2005, the entire contents of which are incorporated herein by reference. This application also claims benefit from U.S. Provisional application 60/630, 193 filed Nov. 24, 2004, the entire contents of which are incorporated herein by reference.

FIELD OF THE INVENTION

The instant invention relates generally to High Field Asymmetric Waveform Ion Mobility Spectrometry (FAIMS), and more particularly to an apparatus and method for controllably varying specificity of a FAIMS-based ion separation.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 µs followed by −1000 V for 20 µs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform, an ion moves with a y-axis velocity component given by $V_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually is neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

In an analytical instrument that includes (1) a condensed phase separation including for example one of liquid chromatography (LC) or capillary electrophoresis, (2) an atmospheric pressure ionization source including for example electrospray ionization (ESI) or atmospheric pressure photoionization (APPI), (3) an atmospheric pressure gas phase ion separator including for example high-field asymmetric waveform ion mobility spectrometer (FAIMS) and (4) a detection system including for example mass spectrometry (MS), it is advantageous to support switching to convert the function of the intermediate gas phase separation device (FAIMS for example) from a mode of separation to a mode in which the ions are not separated. This non-separating mode is called "total ion transmission mode" (TITM). The TITM is beneficial for reviewing the mixture of ions that are arriving at the intermediate separation device, in order to assess whether any ions are being overlooked by application of the intermediate separation stage. The TITM mode in FAIMS is analogous to the rf-only mode of a quadrupole mass spectrometer, in which mode of operation a wide range of ions is transmitted simultaneously through the quadrupole. This rf-only mode supports tandem arrangement of several quadrupole devices, with one or more of the quadrupole devices operated optionally in non-separation mode so that the separation of ions only occurs in one of the series of tandem quadrupole devices.

SUMMARY OF THE INVENTION

It is an object of at least some embodiments of the instant invention to provide a FAIMS device that is selectively operable in a first separation mode and in a second separation mode, the second separation mode having an ion separation resolution that differs from the first separation mode.

It is a further object of at least some of the embodiments of the instant invention to provide a FAIMS device that is selectively operable in a conventional FAIMS separating mode and in a total ion transmission mode (TITM).

According to an aspect of the instant invention, there is provided an apparatus

According to an aspect of the instant invention, there is provided an apparatus

According to an aspect of the instant invention, there is provided a method

BRIEF DESCRIPTION OF THE DRAWINGS

Exemplary embodiments of the invention will now be described in conjunction with the following drawings, in which similar reference numerals designate similar items:

FIG. 8b is a plan view of the plate of FIG. 8a;

FIG. 10b is a simplified end view of the FAIMS of FIG. 10a;

FIG. 13a is a cross sectional end view of a FAIMS in the form of three electrodes with curved adjacent surfaces, with approximate alignment of the ion inlet, the inter-analyzer opening and the ion outlet;

FIG. 13b is a cross sectional end perspective view of the FAIMS of FIG. 13a with approximate alignment of the ion inlet, the inter-analyzer opening and the ion outlet;

FIG. 14a is a cross sectional end perspective view of the FAIMS of FIG. 13a with a displacement of distance A between the ion inlet and the inter-analyzer opening and between the inter-analyzer opening and the ion outlet;

FIG. 14b is a cross sectional end perspective view of the FAIMS of FIG. 13a with a displacement of distance A between the ion inlet and the inter-analyzer opening and between the inter-analyzer opening and the ion outlet, and showing ions flowing along an average ion flow path between the ion inlet and the ion outlet;

FIG. 23 shows patterns of the flow of gases supplied to the curtain region of the system of FIGS. 22a and 22b, when in the second mode of operation;

FIG. 24 shows the system of FIGS. 22a and 22b adapted for the special case of LockSpray™;

FIG. 32 is a simplified schematic view of a FAIMS analyzer including an array of rod-shaped electrodes according to an embodiment of the instant invention, taken along a first direction;

FIG. 33 is a schematic view of a portion of the FAIMS analyzer of FIG. 32, taken along the first direction;

FIG. 34 illustrates the effect of electric fields within the FAIMS analyzer of FIG. 32 on the trajectory of ions;

FIG. 36 is a simplified schematic view of yet another FAIMS analyzer including an array of rod-shaped electrodes according to yet another embodiment of the instant invention, taken along the first direction;

FIG. 38 is a simplified exploded view of yet another FAIMS analyzer including an array of rod-shaped electrodes according to the instant invention including two sets of electrode rods;

FIG. 39a is an exploded isometric view of the FAIMS analyzer of FIG. 38;

FIG. 39b is an isometric view of the FAIMS analyzer of FIG. 38;

DESCRIPTION OF EMBODIMENTS OF THE INVENTION

Figure 1:
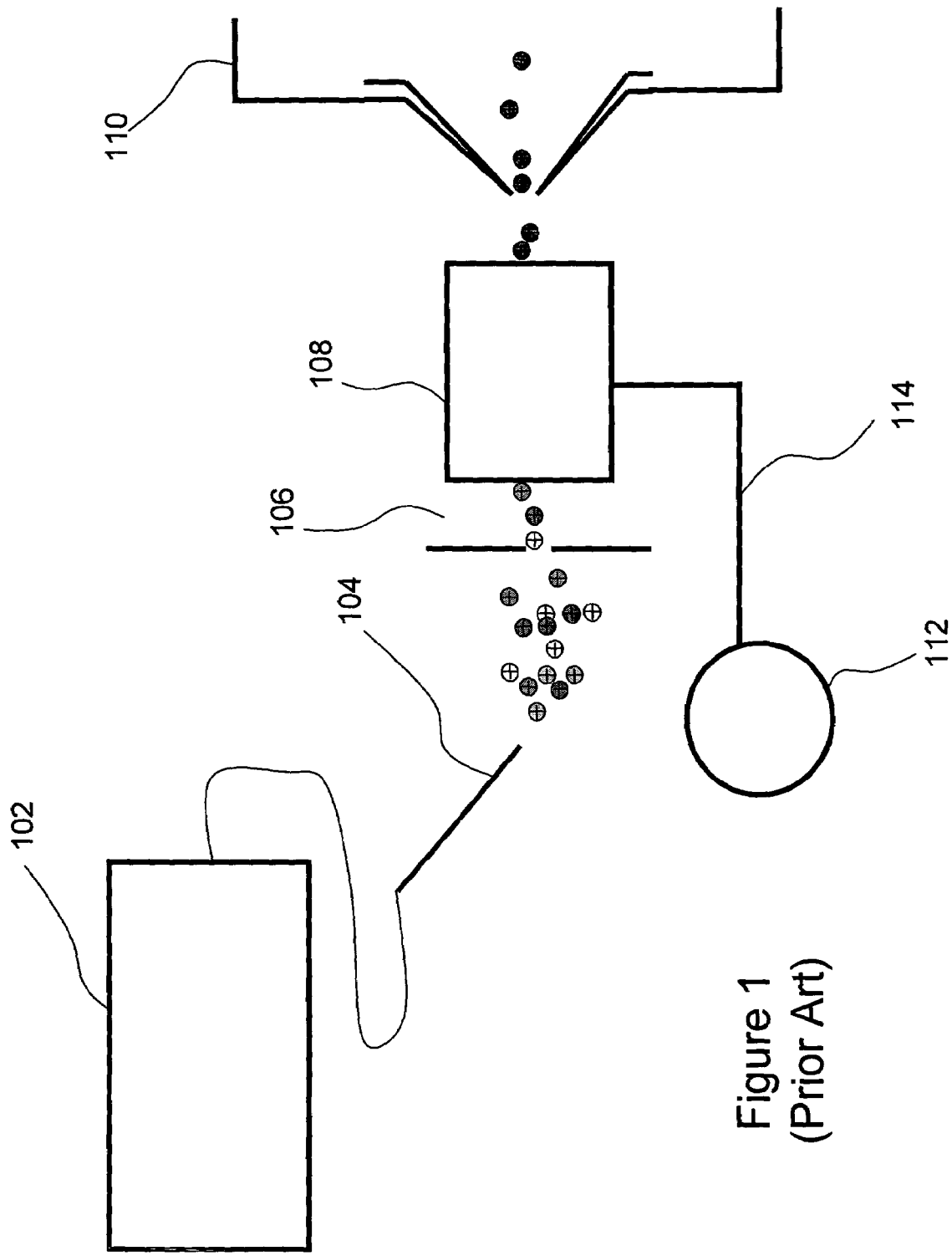
FIG. 1 is a simplified block diagram showing a prior art tandem arrangement including an ion source, a FAIMS, and a mass spectrometer.

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Throughout much of the following discussion it is assumed that the FAIMS electrodes are operating at atmospheric pressure, but the discussion is equally applicable at pressures below ambient atmospheric pressure and at pressures exceeding ambient atmospheric pressure. Furthermore, because ion separation and ion transmission in FAIMS is susceptible to changes in temperature it is desirable to operate FAIMS at a selected temperature setting. For example, a rise in temperature leads to a decrease in the number density of the gas (N, molecules per cc) and therefore the operating electric field (E/N) increases with rising temperature. Similarly an increase in gas pressure increases N and therefore decreases the effective E/N conditions. In order that experiments give consistent results when repeated, it is assumed that the temperatures and pressures are maintained at selected conditions, within selected tolerance limits.

It is also assumed that the physical conditions in the analyzer region of FAIMS do not significantly change the CV of the transmission of the ion of interest while it is passing through the analyzer region to a degree that prevents its transmission. For example, if conditions in different areas of the analyzer region differ substantially, those ions that are initially being successfully transmitted near the ion inlet region likely are lost to the electrode walls at a later time during their passage through the FAIMS analyzer region. This occurs, for instance, when conditions near the ion inlet are in a balanced state for a selected ion type, and the selected ion type is being transmitted near the ion inlet, but at a location elsewhere in the analyzer region the conditions are sufficiently different that the same selected ion type is migrating to the electrode walls and is being lost. Temperature, pressure, composition of the carrier gas and spacing between the electrodes, are a few non-limiting examples of the physical conditions, assuming constant applied voltages, that affect the CV of transmission of an ion. For example, a substantial difference in the electrode spacing near the ion inlet and near the ion outlet results in the field E/N near the inlet and near the outlet being different from each other. In some instances, moderate changes are beneficial for improving the resolution, or specificity, of ion separation, but larger changes that the ion experiences for longer times may result in complete loss of transmission of the ion. The term specificity is intended to describe the number of different ion types actually transmitted through a FAIMS device relative to the number of different ion types that are introduced via an ion inlet of the FAIMS. High specificity indicates that few or only one type of ion is actually being transmitted through the FAIMS, whereas low specificity indicates that many or all types of ion are actually being transmitted through the FAIMS. Of course, ion transmission efficiency may vary significantly with ion type, or may be relatively constant for different ion types. Thus, a total ion transmission mode (TITM) is by definition a low specificity mode of operation in which at least some fraction of many or all types of ions that are introduced via an ion inlet are transmitted through the FAIMS device to an ion outlet.

Referring now to FIG. 1, shown is a simplified block diagram of a prior art tandem arrangement including a condensed phase separation system 102, an ionization source 104, an ion desolvation region 106, a FAIMS 108, and a mass spectrometer 110. A power supply 112 applies voltages including an asymmetric waveform voltage and a compensation voltage to not illustrated electrodes of the FAIMS 108 via electrical connection 114. In FIG. 1 the ionization source 104 is shown, by way of non-limiting example, in the form of an electrospray ionization source. However, many other suitable ion sources are known, including photoionization sources, APCI sources, atmospheric pressure MALDI, radioactivity based sources, corona discharge sources, and other rf-based discharge sources, to name just a few non-limiting examples. The components 104, and 106 optionally are at elevated temperature to assist in desolvation of the ions, whereas 102, 108, and 110 are optionally at room temperature.

Referring still to FIG. 1, sample is provided from the condensed phase separation system 102 to ionization source 104. Ions produced from the sample are introduced into FAIMS 108 via desolvation region 106, and are separated according to the FAIMS principle. Ions that are transmitted through FAIMS 108 then travel to mass spectrometer 110 to be analyzed further or detected.

Figure 2:
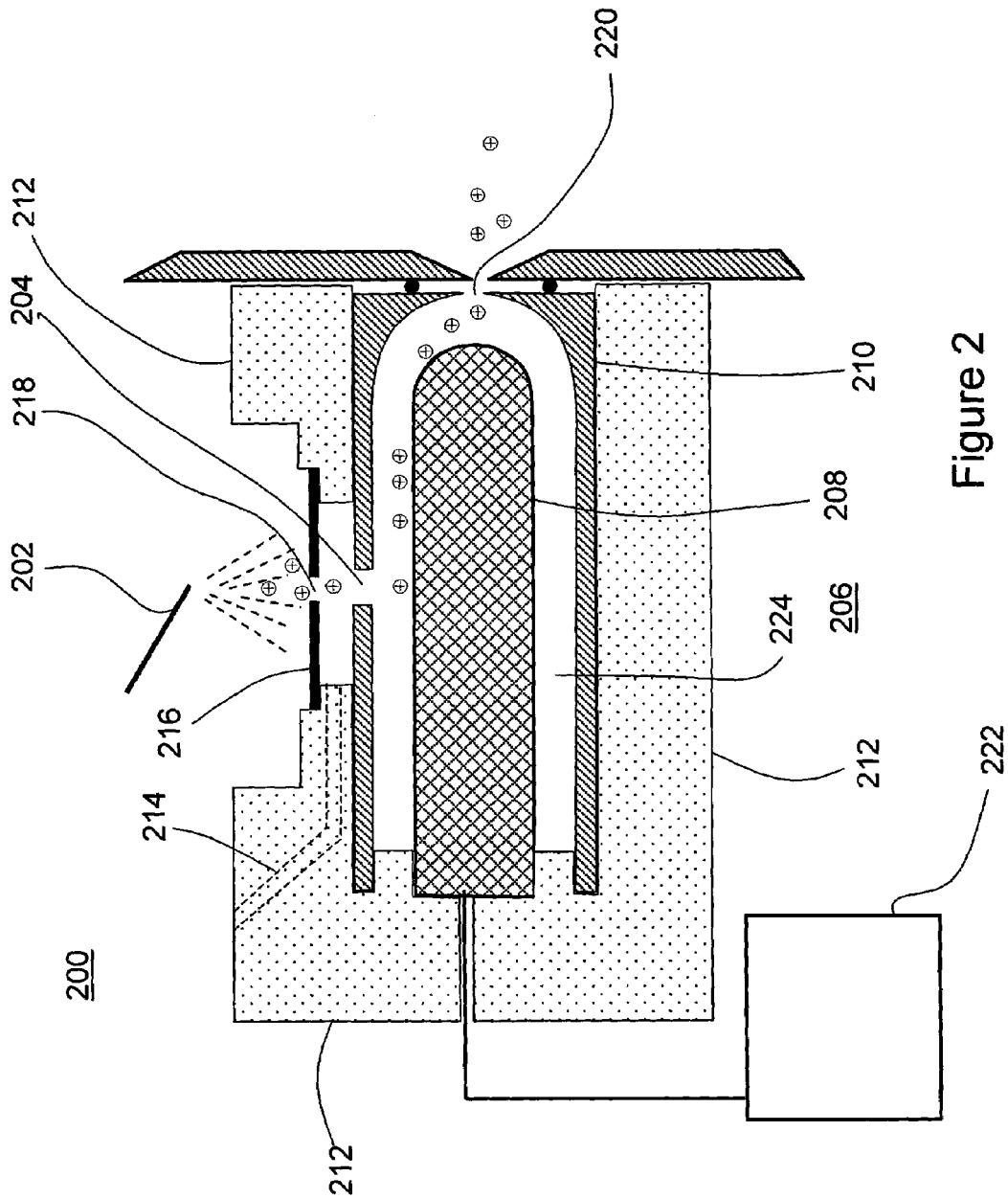
FIG. 2 is a longitudinal cross-sectional view of an electrospray ion source disposed in fluid communication with an ion inlet of a FAIMS.

Referring now to FIG. 2, shown is a longitudinal cross-sectional view of an ESI-FAIMS-MS tandem system, shown generally at 200. An electrospray ionization needle 202 is disposed in fluid communication with an ion inlet 204 of a FAIMS 206. The inner electrode 208 and the outer electrode 210 are supported in a spaced-apart arrangement by an insulating material 212 with high dielectric strength to prevent electrical discharge. Some non-limiting examples of suitable materials for use as the insulating material 212 include Teflon™ and PEEK. A passageway 214 for introducing a curtain gas is shown by dashed lines in FIG. 2, but often is omitted in later figures for simplicity of interpretation of the figures.

In FIG. 2, the ions are formed near the tip of electrospray needle 202 and drift towards a curtain plate 216. The curtain gas, introduced below the curtain plate 216 via the passageway 214, divides into two portions, one of which flows through an aperture 218 in the curtain plate 216, so as to prevent neutrals and droplets from entering the curtain plate aperture 218. Ions are driven against this flow of gas by a voltage gradient that is established between the needle 202 and the curtain plate 216. A field generated by a voltage difference applied between the curtain plate 216 and the FAIMS outer electrode 210 pushes ions that pass through the aperture 218 in the curtain plate 216 towards the ion inlet 204 of FAIMS 206. The second portion of the curtain gas flows into the ion inlet 204 and carries the ions along the length of the FAIMS electrodes to an ion outlet 220, and into a not illustrated mass spectrometer or other post-FAIMS analyzer/detector.

A high voltage asymmetric waveform is applied by electrical controller 222 to the inner electrode 208 of FAIMS 206, to produce an electric field that causes ions within an annular space between the inner electrode 208 and the outer electrode 210, which annular space is referred to as the analyzer region 224, to oscillate between the inner electrode 208 and the outer electrode 210. The waveform is generated in such a way to cause the ions to move in a first direction in a strong field for a short time, followed by motion in the other direction in a weaker field for a longer time. Absent any change in ion mobility between the high field and low field portions of this applied asymmetric waveform, after each cycle of the waveform the ion returns to its original position relative to the surface of the electrodes, without consideration of diffusion or ion-ion repulsion. In practice however, the mobility of many ions is different in strong and weak electric fields and for these ions the ion's position after one cycle of the waveform is not identical to its starting position relative to the electrode surfaces. A second, direct current voltage, which is referred to as the compensation voltage (CV), is applied to eliminate or compensate for this change of position. If the compensation voltage is of a magnitude that eliminates or compensates for the change of position that otherwise occurs absent the compensation voltage, the ion returns to the same relative location after each cycle of the waveform. Thus the ion does not migrate towards one or the other of the electrodes, and is transmitted through FAIMS 206. Other ions, for which the compensation voltage is too high or too low to compensate for the net displacement of the ion relative to the electrodes during one cycle of the waveform, drift towards an electrode and are unable to pass through FAIMS 206.

Still referring to FIG. 2, the cylindrical electrode geometry also permits ion focusing of the ion for which the asymmetric waveform voltage and compensation voltages are appropriate for transmission through FAIMS. This ion focusing mechanism means that ions, for which the compensation voltage exactly balances the change in position noted above, do not travel parallel to the walls of the electrodes as they are transported by the gas along the analyzer region 224. Under conditions of focusing, the ions that were originally near the electrode walls migrate to an optimum radial location between the electrodes. The ion cloud therefore tends to be located around this optimum radial location, thus 'focusing' the ions into a band within the space between the electrodes. Of course this cloud occupies a finite amount of space because the focusing is not strong and because diffusion, ion-ion electrostatic repulsion and other mechanical and chemical activity, including turbulence of the gas, tends to cause the ion cloud to spread out in space. At equilibrium the forces expanding the cloud are balanced by the focusing action of the electric fields in the analyzer region of FAIMS. This focusing effect is a result of the gradient of electric field E/N between the electrodes. In this example the gradient is generated because the electrodes are of cylindrical geometry, one of the possible physical geometries of electrodes that gives rise to non-constant E/N in space between the electrodes.

Two approaches are discussed for operating FAIMS 206 in total ion transmission mode. In a first approach the asymmetric waveform is deactivated and the inner electrode 208 and the outer electrode 210 are held at a same voltage. In a not illustrated second approach the asymmetric waveform is deactivated and the inner electrode 208 is retracted, or translated, so that the tip of the hemispherical end of the inner electrode 208 is no longer between the ion inlet 204 and the ion outlet 220. The voltages applied to the inner electrode 208 and to the outer electrode 210 are established empirically, to produce optimized ion transmission. In both of these approaches the mixture of ions that enters through ion inlet 204 is not separated by the FAIMS mechanism, and some of the non-separated mixture of ions exits through the ion outlet 220. The extent to which the ions are transmitted is influenced also by other mechanisms for relative selectivity of ion transmission, for example the relative rates of loss of various types of ions via diffusion. It is also important to note that the ion focusing properties of FAIMS are not operative absent the asymmetric waveform, since the variation in E/N in the radial direction is not sufficient for focusing, so that the ions are lost by mechanisms that include diffusion and ion-ion electrostatic mutual repulsion. Unfortunately, when operating in this optional non-separating mode, the length of the ion path between the ion inlet 204 and the ion outlet 220 is long, and the efficiency of transmission of the ions between the ion inlet 204 and the ion outlet 220 is low.

Figure 3:
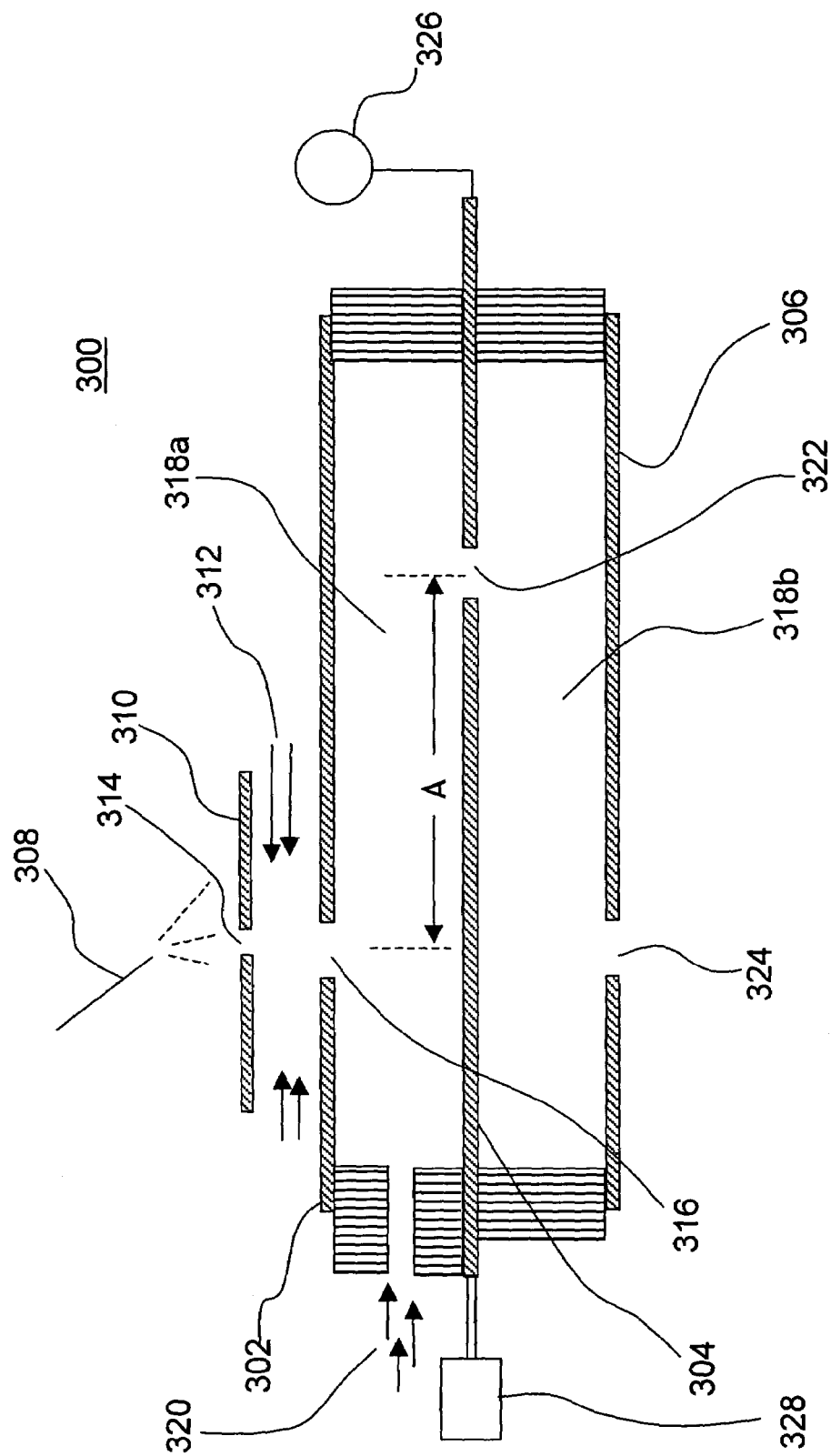
FIG. 3 is a longitudinal cross-sectional view of a parallel-plate geometry FAIMS, with a displacement of A between the openings in the top and middle plates and between the openings in the middle and lower plates.

FIG. 3 is a longitudinal cross-sectional view of a parallel plate FAIMS 300 including three stacked plates 302, 304 and 306, disposed in a spaced-apart relationship. The plates 302, 304 and 306 are stacked along a first direction, referred to as the stacking direction, such that a first electrode surface along plate 302 faces one side of the intermediate electrode plate 304, and a second electrode surface along plate 306 faces a side of the intermediate electrode plate 304 that is opposite the one side. Ions that are produced by ion source 308 drift along the first direction toward a curtain plate 310. A flow of a curtain gas 312, introduced below the curtain plate 310, divides into two portions, one of which flows outwardly through an aperture 314 in the curtain plate 310, so as to prevent neutrals and droplets from entering the curtain plate aperture 314. Ions are driven against this flow of gas by a voltage gradient that is established between the ion source 308 and the curtain plate 310. A field generated by a voltage difference between the curtain plate 310 and the FAIMS plate 302 pushes ions that pass through the aperture 314 in the curtain plate 310 towards the ion inlet 316 of FAIMS 300. The second portion of the curtain gas flows into the ion inlet 316 and carries the ions along the length of the FAIMS electrodes through the analyzer region 318a, along a second direction that is normal to the first direction. A second carrier gas flow 320 is optionally provided to assist in carrying the ions along the analyzer region 318a.

The ions travel along an average ion flow path, as is described hereinbelow. In particular, the ions travel an approximate distance along the average ion flow path indicated as "A" from the inlet 316 to an orifice, referred to as inter-analyzer aperture 322. The ions are carried by the flow of gas through the inter-analyzer aperture 322 into a second analyzer region 318b, and travel a second approximate distance "A" along the average ion flow path to the ion outlet 324. Accordingly, the inter-analyzer aperture defines a transition point, for changing the direction of ion flow along the average ion flow path. Since the asymmetric waveform and dc offset voltage is applied to the plate 304 from power supply 326, and assuming that the distance between plate 302 and 304 and between plate 304 and 306 are approximately equal, both analyzer regions 318a and 318b operate to separate ions in a substantially equivalent way. Optionally, to improve ion separation resolution, slightly different conditions are imposed in these analyzer regions 318a and 318b, for instance by varying electrode spacing or by application of different dc voltages to plates 302 and 306.

Figure 4:
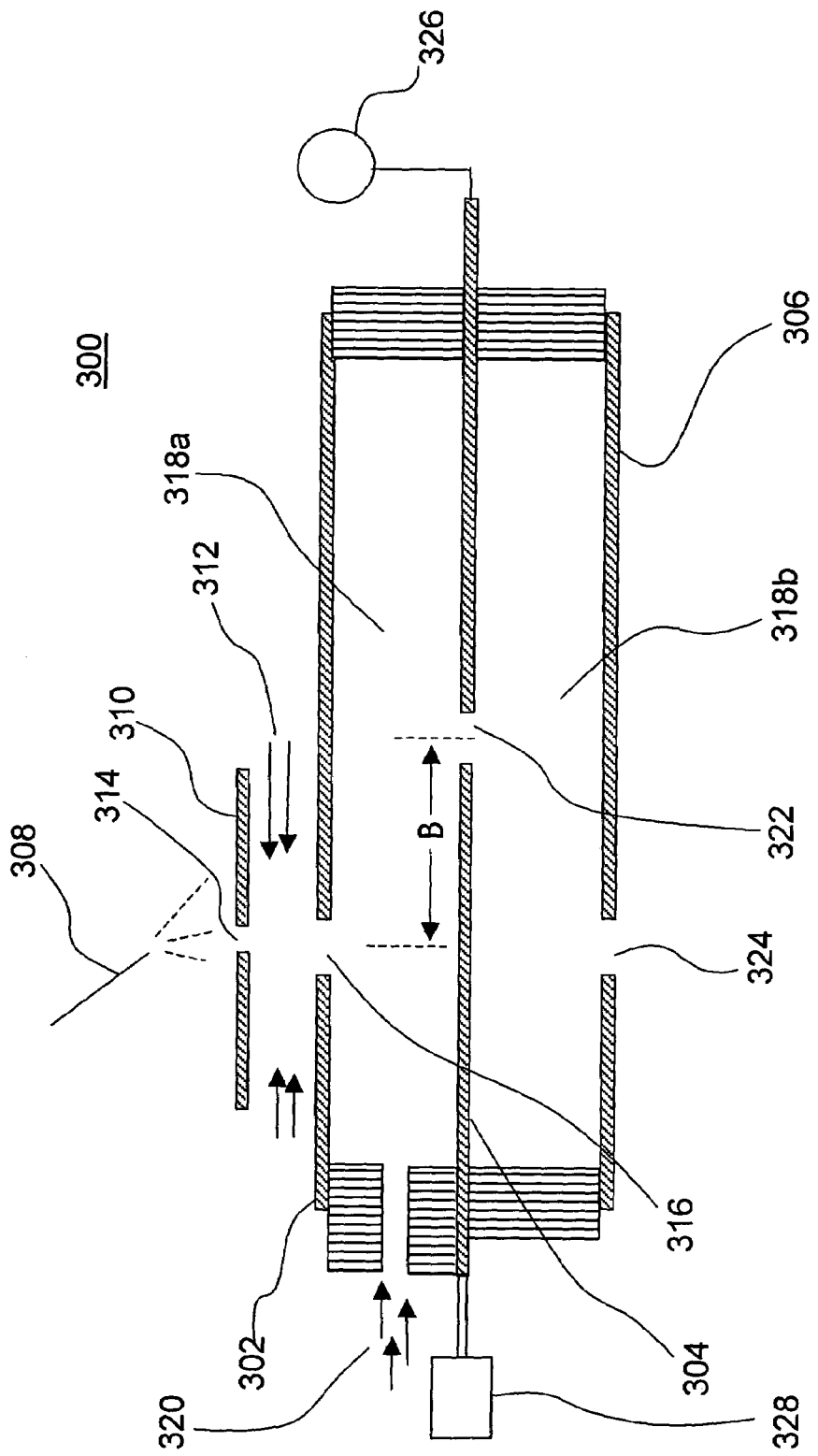
FIG. 4 is a longitudinal cross-sectional view of the FAIMS of FIG. 3 with a displacement of B between the openings in the top and middle plates and between the openings in the middle and lower plates.

FIG. 4 is a longitudinal cross-sectional view of the FAIMS of FIG. 3, with the inter-analyzer aperture 322 located at a distance "B" from the ion inlet 316. This system is designed such that the position of the inter-analyzer aperture 322 is selectable relative to the ion inlet 316 and the ion outlet 324. For instance, a controller including an actuator 328 is provided for translating the intermediate electrode plate 304 along the second direction, so as to translate the transition point as defined by the inter-analyzer aperture 322, and thereby controllably vary a length of the average ion flow path. The actuator 328 is optionally one of manually operable and automatically operable. For instance, the actuator 328 optionally includes a thumb-screw, an adjustable wheel or knob, or some other manually operable control mechanism for supporting manual adjustment of the inter-analyzer aperture 322 position. Alternatively, the actuator 328 optionally includes a motor that drives the electrode 304 in one of a continuous and a stepped manner via a linkage member.

FIG. 4 illustrates that this arrangement of electrodes provides the benefit of an adjustable ion transit time, allowing the separation of ions and the efficiency of ion transmission to be established empirically by adjusting the position of the inter-analyzer aperture 322 relative to the ion inlet 316 and the ion outlet 324. If the gas flow rate is sufficiently high that the ion residence time is too short to achieve a desired degree of separation of one type of ion from another type of ion, the distance B between the ion inlet 316 and the inter-analyzer aperture 322 is increased, for instance to distance "A" as shown previously in FIG. 3. Optionally this distance is adjusted by mechanical horizontal translation of plate 304, however, those knowledgeable in the field will appreciate that this distance is readily adjusted in many different ways.

In principle, the device as configured in either of FIG. 3 and FIG. 4 optionally is operated in a non-separating TITM by removal of the asymmetric waveform and the dc compensation voltage. In this condition the device shown in FIG. 3 and FIG. 4 passes a mixtures of ions without active FAIMS-based separation however the mixture of ions is required to travel some distance between the closely spaced electrodes/plates and ion transmission efficiency from the ion source to the post-FAIMS detector/analyzer is expected to be reduced.

Figure 5:
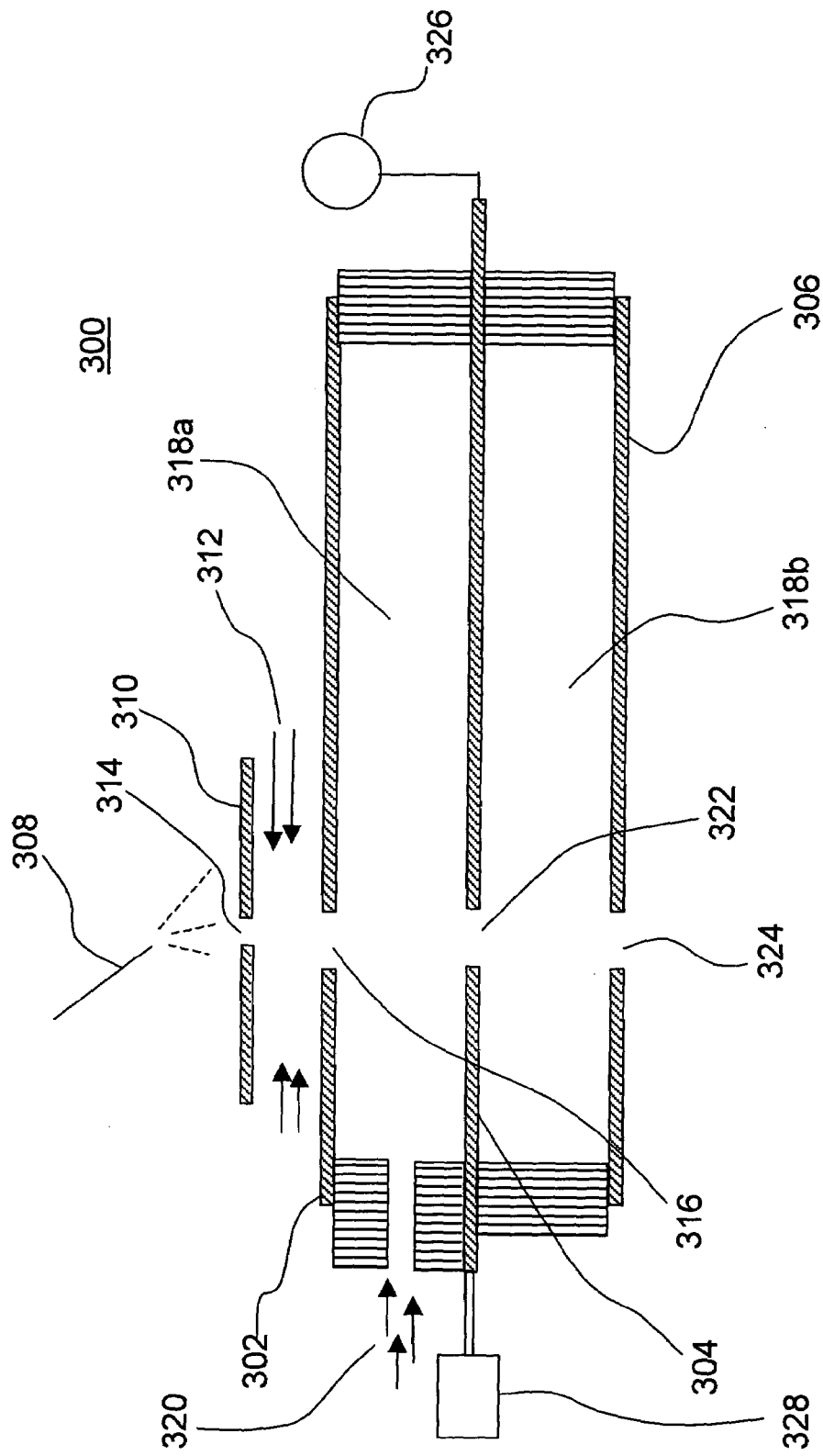
FIG. 5 is a longitudinal cross-sectional view of the FAIMS of FIG. 3 with the openings in the top, middle and lower plates vertically aligned.

It is an unforeseen benefit of the system shown in FIG. 3 and FIG. 4 that the distances "A" or "B" are optionally reduced effectively to zero, as shown in FIG. 5. This also has the advantage of de-activating the FAIMS, and thereby providing a readily available mechanism for total ion transmission mode (TITM). Referring now to FIG. 5, by aligning the ion inlet 316, the inter-analyzer aperture 322 and the ion outlet 324, the ion separation mechanism of FAIMS is minimized, so that the majority of ions passing through ion inlet 316 exit through the ion outlet 324. The transmission of ions is significantly higher with the alignment of the ion inlet 316, the inter-analyzer aperture 322 and the ion outlet 324, than if the inter-analyzer aperture 322 remained located at distance "A" or "B" as shown in FIGS. 3 and 4 with the asymmetric waveform and the dc compensation voltage removed. Furthermore, in FIG. 5 the ion transmission may be also controlled by removal of the applied asymmetric waveform and replacement of the dc voltages applied to plates 302, 304 and 306 with dc voltages that are determined empirically to maximize the efficiency of transport of ions from the ion inlet 316 to the ion outlet 324.

Still referring to FIG. 5, assuming the widths of the analyzer regions 318a and 318b are each 2 mm, the distance from the ion inlet 316 to the ion outlet 324 is now only 4 mm plus the thickness of the plate 304. The efficiency of transport of ions through this non-separating FAIMS is significantly higher than that of the system in the state shown in FIG. 3 or FIG. 4 operated in non-separating mode by removal of the waveform voltages, since for example in the system of FIG. 3 the ions travel twice the distance "A". Additionally, when operating in a non-separating mode the ions are difficult to transport unless the dc voltages applied to the plates 302, 304 and 306 are substantially equal, since any voltage difference adds an electric field that tends to force the ions to collide with one of the plates. Referring again to FIG. 5, the dc voltages applied to the plates 302, 304 and 306 are helpful in pulling the ions through the three co-aligned openings, namely ion inlet 316, inter-analyzer aperture 322 and ion outlet 324.

Although the system shown in FIGS. 3 through 5 include three separate electrode plates 302, 304 and 306, optionally the plates 302 and 306 are replaced by a single formed electrode having a generally "C-shaped" structure, such that a first electrode surface portion of the formed electrode faces one side of the intermediate electrode plate 304, and a second electrode surface portion of the same formed electrode faces a side of the intermediate electrode plate 304 that is opposite the one side.

Of course, the parallel plate version of FAIMS that is shown in FIGS. 3 through 5 is known to lack focusing properties, other than at the edges of the plates, in the absence of temperature gradients or any other conditions creating an electric field gradient between the electrodes. Fortunately, when temperature conditions between the parallel plate electrodes are established to mimic the E/N gradient in cylindrical geometry FAIMS, a beneficial focusing effect occurs. The transmission of ions at a fixed CV requires control of the temperature in the analyzer region, such that the CV conditions for transmission of a selected ion do not change significantly as the ion travels along the space between the electrodes. By controlling the temperature of the carrier gas and by controlling the temperature of each of the electrodes to create a temperature gradient in the gas between the electrodes, ion focusing conditions are established in the parallel plate version of FAIMS.

Figure 6:
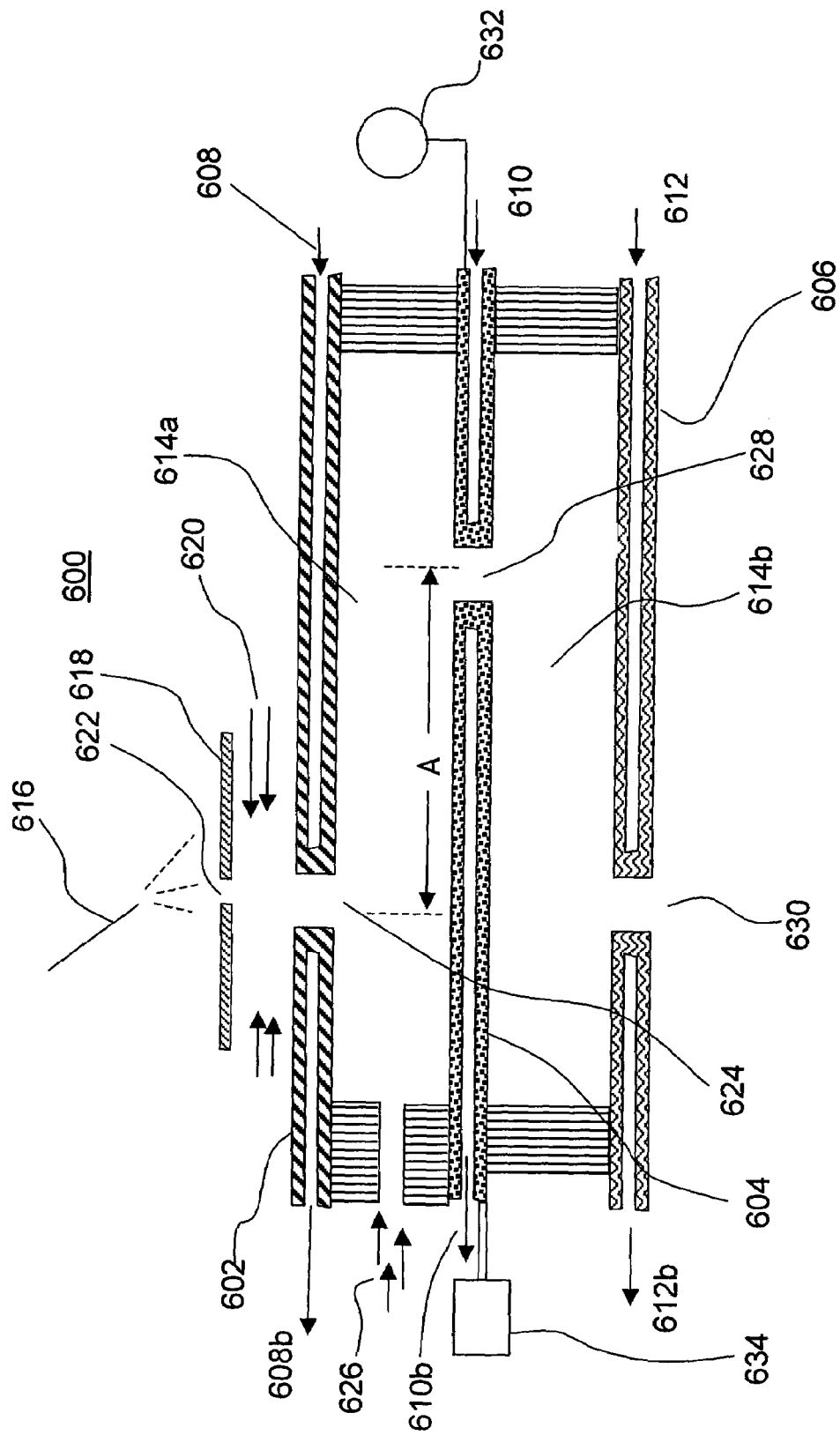
FIG. 6 is a longitudinal cross-sectional view of a parallel-plate geometry FAIMS including a temperature controller for controlling the temperature of the three plates.

FIG. 6 illustrates a FAIMS system 600 similar to that shown in FIGS. 3 through 5, however a temperature controller is provided to control the relative temperatures of each of the three plates 602, 604 and 606. Three flows 608, 610 and 612 of a heating/cooling fluid, referred to more generally as a heat-exchange fluid, are delivered to channels in the plates 602, 604 and 606 respectively. The heat-exchange fluid passes through channels in the plate and exits from the three plates as flows 608b, 610b and 612b from plates 602, 604 and 606 respectively. Preferably these three heat-exchange fluid flows are circulated and temperature controlled independently. The heat-exchange fluid flows are used to adjust and stabilize the temperatures of the three plates, with the benefit of producing temperature gradients between the electrodes. The temperature gradient produces a gradient of E/N between the plates during application of the asymmetric waveform and dc offset voltages between the electrodes. The gradient of E/N is beneficially controlled to maximize the ion transmission through the analyzer regions 614a and 614b.

Referring still to FIG. 6, ions that are produced by ion source 616 drift toward a curtain plate 618. A flow of a curtain gas 620, introduced below the curtain plate 618, divides into two portions, one of which flows outwardly through an aperture 622 in the curtain plate 618, so as to prevent neutrals and droplets from entering the curtain plate aperture 622. Ions are driven against this flow of gas by a voltage gradient that is established between the ion source 616 and the curtain plate 618. A field generated by a voltage difference between the curtain plate 618 and the FAIMS plate 602 pushes ions that pass through the aperture 622 in the curtain plate 618 towards the ion inlet 624 of FAIMS 600. The second portion of the curtain gas flows into the ion inlet 624 and carries the ions along the length of the FAIMS electrodes through the analyzer region 614a. A second carrier gas flow 626 is optionally provided to assist in carrying the ions along the analyzer region 614a.

The ions travel along an average ion flow path, as is described hereinbelow. In particular, the ions travel an approximate distance along the average ion flow path indicated as "A" from the inlet 624 to an orifice in the intermediate electrode plate 604, which is referred to as inter-analyzer aperture 628. The ions are carried by the flow of gas through the inter-analyzer aperture 628 into a second analyzer region 614b, and travel a second approximate distance "A" along the average ion flow path to the ion outlet 630. Accordingly, the inter-analyzer aperture 628 defines a transition point, for changing the direction of ion flow along the average ion flow path. Since the asymmetric waveform and dc offset voltage is applied to the plate 604 from power supply 632, and assuming that the distance between plate 602 and 604 and between plate 604 and 606 are approximately equal, both analyzer regions 614a and 614b operate to separate ions in a substantially equivalent way. Optionally, to improve resolution, slightly different conditions are imposed in these analyzer regions 614a and 614b, for instance by electrode spacing variation or by application of different dc voltages to plates 602 and 606.

Figure 7:
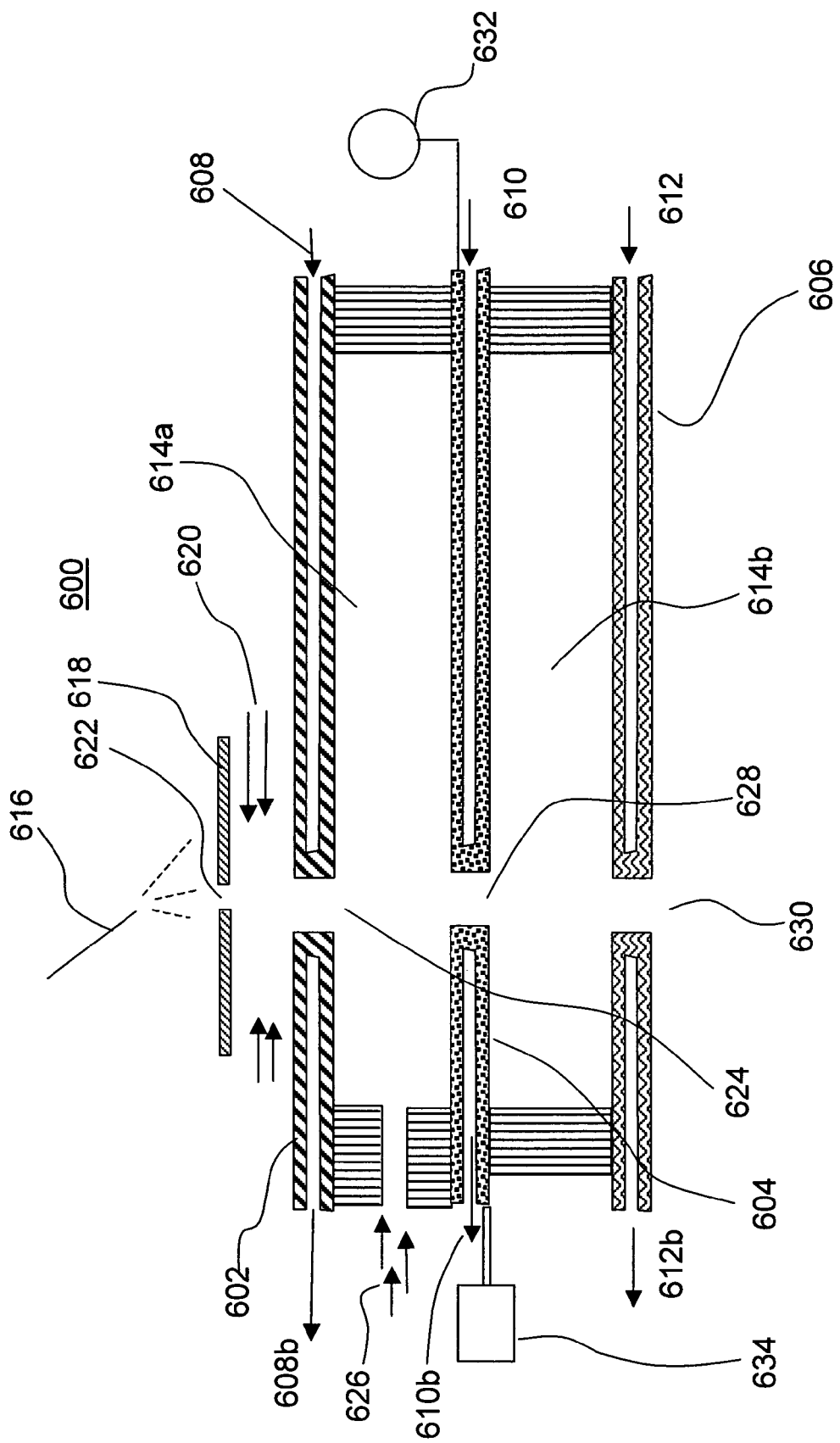
FIG. 7 is a longitudinal cross-sectional view of the FAIMS of FIG. 6 with the openings in the top, middle and lower plates vertically aligned.

FIG. 7 illustrates the same system that is shown in FIG. 6, but with the inter-analyzer aperture 628 located in alignment with the ion inlet 624 and the ion outlet 630. For instance, a controller including an actuator 634 is provided for translating the intermediate electrode plate 604 along a direction parallel to the plates 602 and 606, so as to translate the transition point as defined by the inter-analyzer aperture 628, and thereby controllably vary a length of the average ion flow path. The actuator 634 is optionally one of manually operable and automatically operable. For instance, the actuator 634 optionally includes a thumb-screw, an adjustable wheel or knob, or some other manually operable control mechanism for supporting manual adjustment of the inter-analyzer aperture 628 position. Alternatively, the actuator 634 optionally includes a motor that drives the intermediate electrode plate 604 in one of a continuous and a stepped manner via a linkage member. With alignment of the three openings the ions that are delivered to ion inlet 624 pass without separation to the ion outlet 630, with the device acting in total ion transmission mode. In this mode of operation, it is preferable that the asymmetric waveform be deactivated, and dc potentials placed on all three plates 602, 604 and 606. The dc potentials are selected to maximize the efficiency of transmitting ions from ion inlet 624 to ion outlet 630.

Figure 8A:
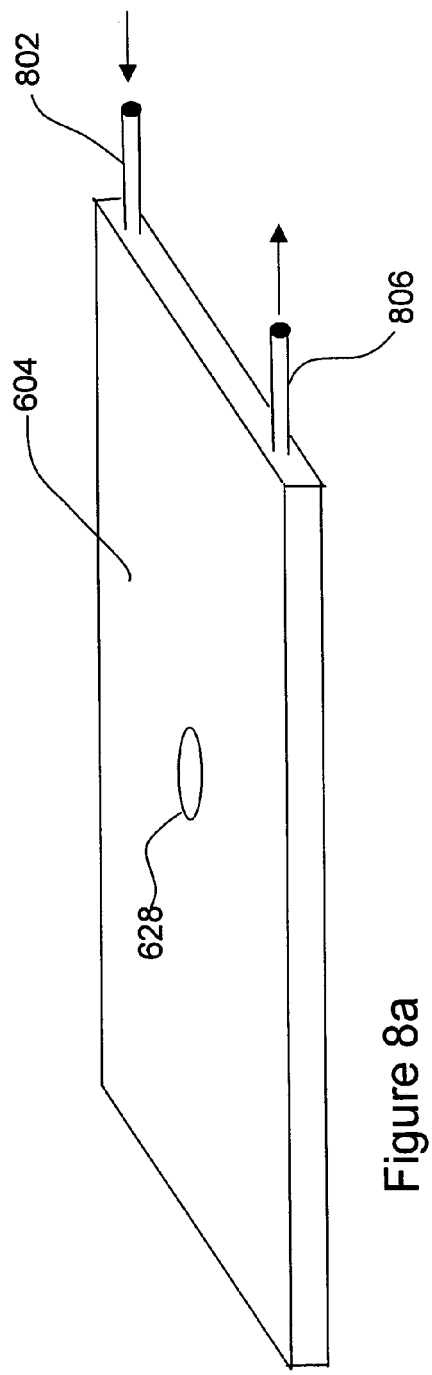
FIG. 8a is a perspective view of one of the plates of the FAIMS of FIG. 6, showing the heat-exchange fluid circulation system in greater detail.
Figure 8B:
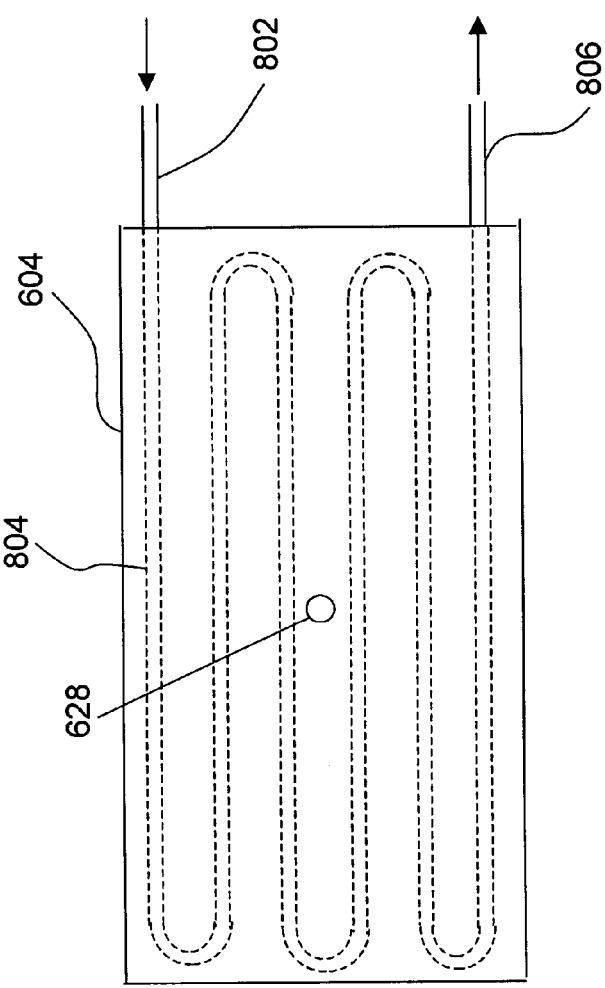

FIGS. 8a and 8b illustrate one approach to passing a heat-exchange fluid through the plates 602, 604 or 606 of the system shown in FIG. 6 and FIG. 7. In the specific example that is shown in FIGS. 8a and 8b, a flow of the heat-exchange fluid enters plate 604 through a fluid inlet 802, and having passed along a channel 804 within the plate, the fluid exits from fluid exit port 806. Optionally the plate is heated by resistive elements or thermoelectric elements embedded into the plate. Optionally, similar structure is provided for controlling temperature of plates 602 and 606.

Figure 9A:
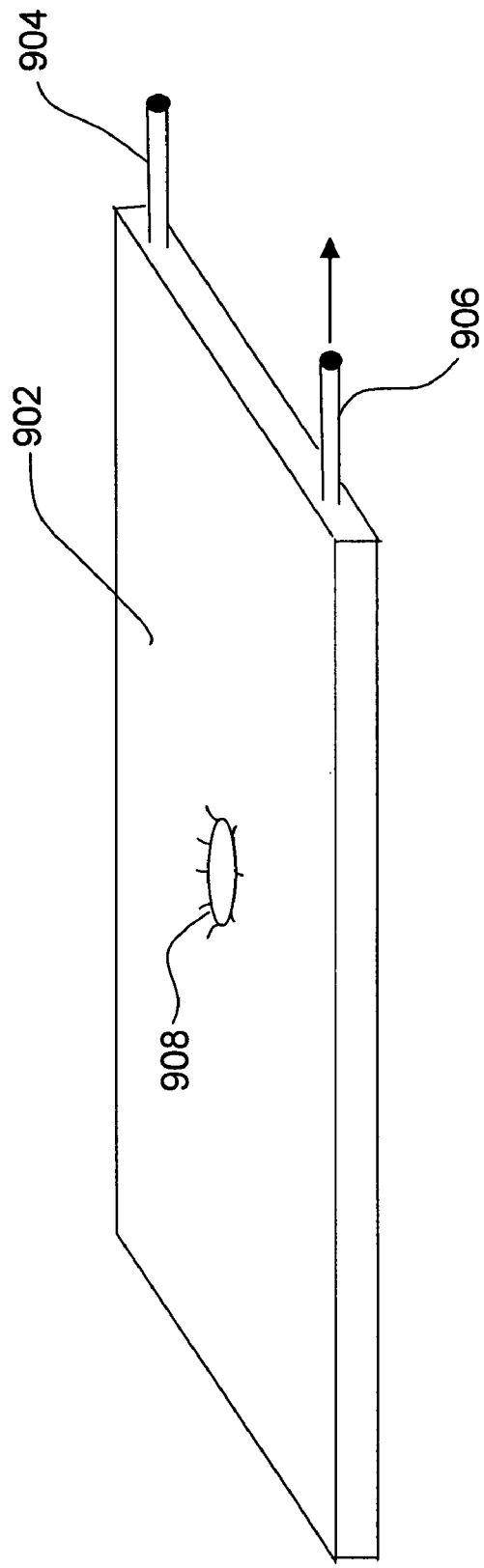
FIG. 9a is a perspective view of an optional flat plate design, in which the plate is absent sharp edges adjacent the inter-analyzer opening.
Figure 9B:
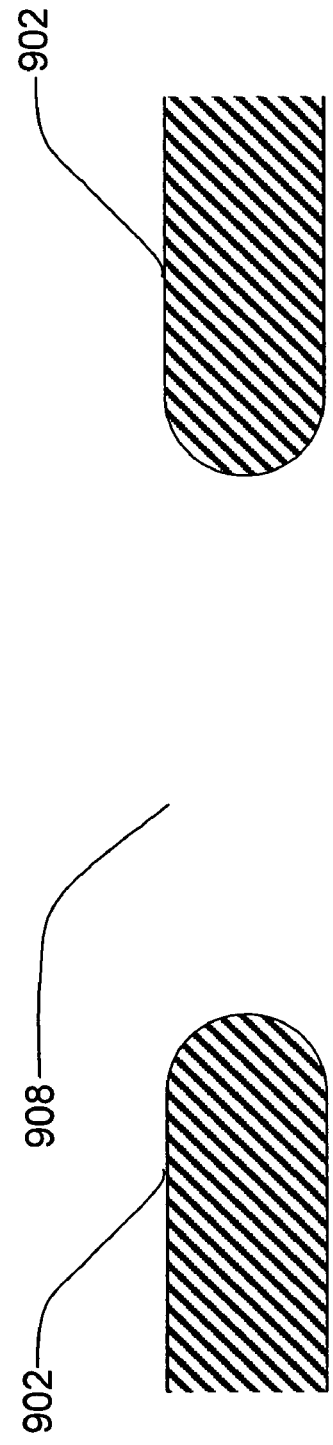
FIG. 9b is an enlarged partial side cross-sectional view of the flat plate of FIG. 9a, showing the shape of the inter-electrode opening in greater detail.

Referring now to FIG. 9a and FIG. 9b, shown is a perspective view and an enlarged partial side cross-sectional view, respectively, of an optional flat plate design, in which the plate 902 is absent sharp edges adjacent the inter-analyzer aperture 908. In the specific example that is shown in FIG. 9a, a flow of a heat-exchange fluid enters plate 902 through a fluid inlet 904, and having passed along a not illustrated channel within the plate, the heat-exchange fluid exits from fluid exit port 906. The periphery of inter-analyzer aperture 908 is curved so as to smoothly join the upper and lower surfaces of plate 902. The absence of sharp edges on plate 902 adjacent the inter-analyzer aperture 908 beneficially guides ions and gas flow through the inter-analyzer aperture 908 and reduces the possibility of electrical arcing between the plate 902 and adjacent electrode surfaces.

The embodiments of the present invention that have been discussed with reference to FIGS. 3 through 7 beneficially provide a very thin and relatively flat FAIMS device, which is readily positioned between a source of ions and the inlet of a post-FAIMS analyzer, such as for instance a mass spectrometer or further FAIMS devices. Advantageously, neither the ionization source nor the post-FAIMS analyzer is mechanically moved during the switching between separation mode and the non-separating TITM of FAIMS.

Figure 10A:
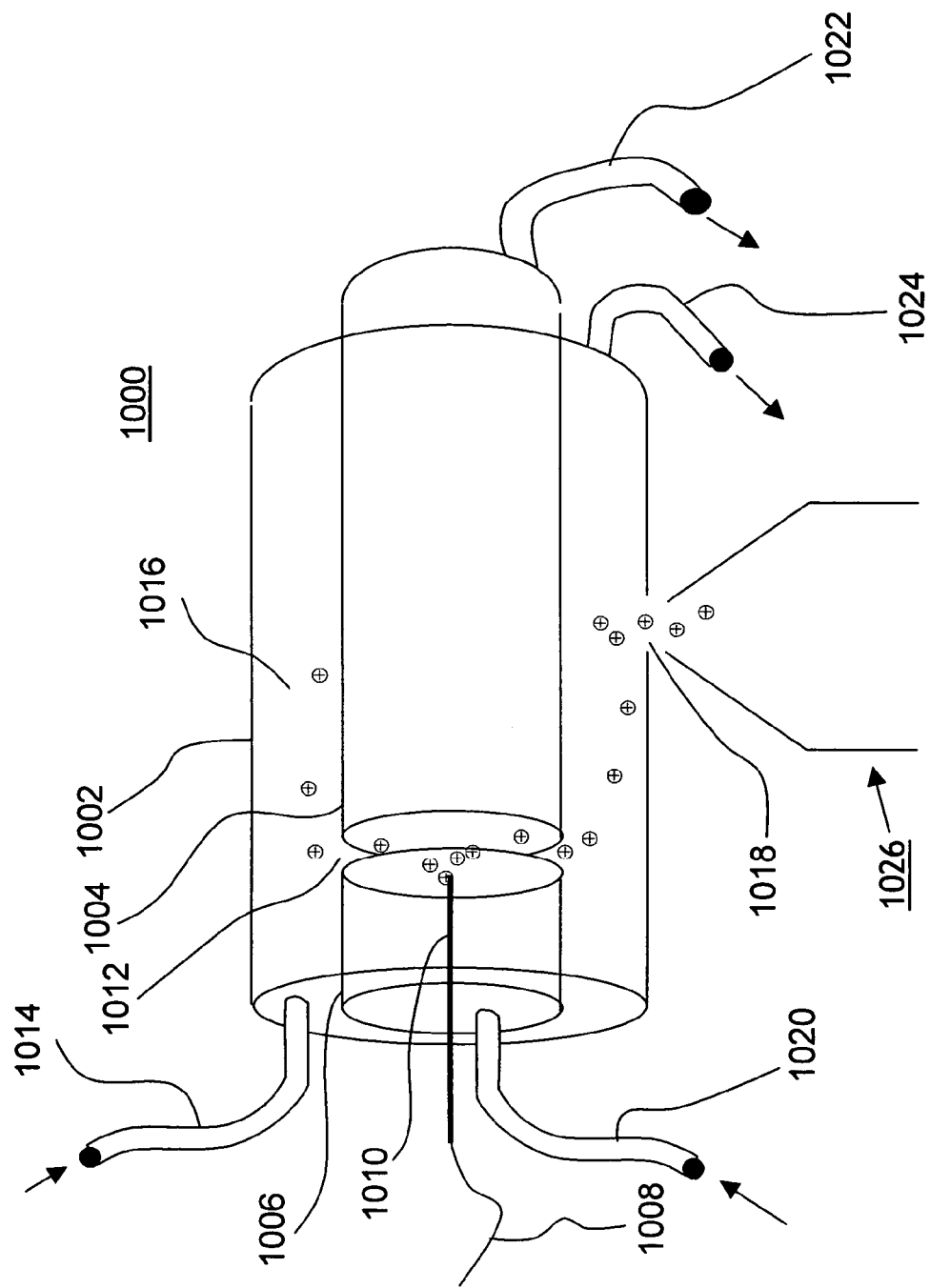
FIG. 10a is a side view of a cylindrical geometry FAIMS including a long cylinder surrounding two shorter axially aligned cylinders, and having a source of ions proximate to a gap between the two shorter aligned cylinders.
Figure 10B:
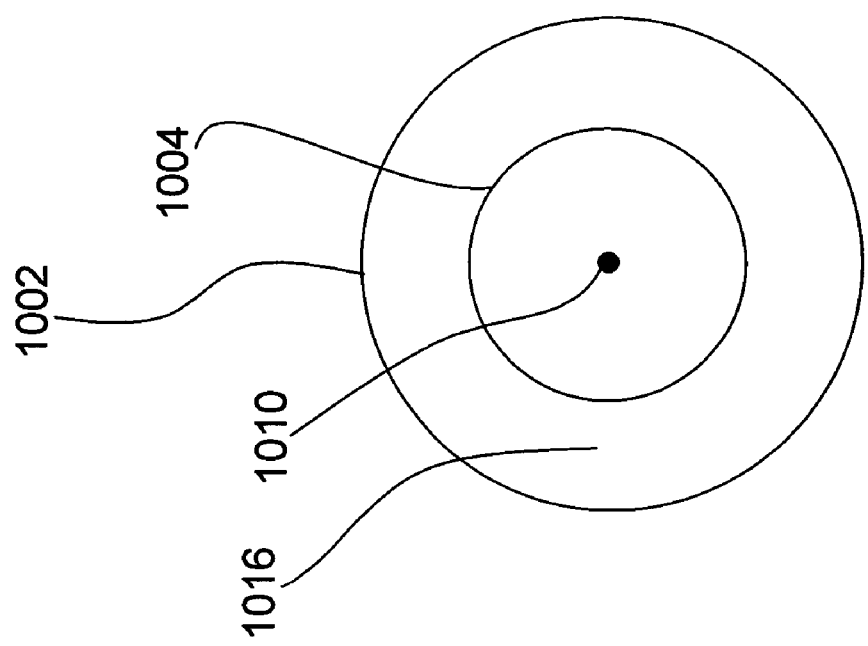

Referring now to FIGS. 10a and 10b, shown is a side view and a simplified end view, respectively, of a cylindrical geometry FAIMS 1000 including a long outer cylinder 1002 surrounding a first inner cylinder 1004 and a second inner cylinder 1006 that is axially aligned with the first inner cylinder 1004. In FIG. 10a, the long outer cylinder is transparent, so as to show more clearly the inner components including the first inner cylinder 1004 and the second inner cylinder 1006. Not illustrated electrically insulating material supports the first inner cylinder 1004 and the second inner cylinder 1006 relative to the long outer cylinder 1002, so as to maintain spacing therebetween.

A flow of liquid sample is provided through a sample delivery tube 1008 to the tip of an ESI source needle 1010. Ions are produced and pushed outward radially because of the high voltage applied to the ESI source needle 1010. Appropriate voltages applied to the shorter second inner cylinder 1006 and the long outer cylinder 1002 drive the ions outwardly in a radial direction away from the source needle 1010 and through a gap 1012 between the shorter second inner cylinder 1006 and the longer first inner cylinder 1004. In this example, the asymmetric waveform and dc offset compensation voltages are applied to the first inner cylinder 1004 through not-illustrated electrical connections.

Referring still to FIGS. 10a and 10b, the ions pass radially outward through the gap 1012 and are entrained in a flow of carrier gas that is supplied by carrier gas conduit 1014 to the annular space between the concentric second inner cylinder 1006 and the long outer cylinder 1002. The carrier gas flow transports the ions along the annular analyzer region 1016 from the gap 1012 to the ion outlet 1018. By application of appropriate asymmetric waveform voltage and dc voltages to the first inner cylinder 1004 and the long outer cylinder 1002, the ions are separated during transport along the analyzer region 1016. A flow of sampler gas provided to the sampler gas conduit 1020 serves to carry neutral molecules and solvent through the space inside of the longer first inner cylinder 1004, after which the gas and the entrained molecules exit from the system through a sampler gas exit conduit 1022. An exit flow of carrier gas is optionally transported out of carrier gas exit conduit 1024. The gas flows, that is to say, the flow through carrier gas conduit 1014, sampler gas conduit 1020, sampler gas exit conduit 1022 and carrier gas exit conduit 1024, are adjusted to ensure that a stream of carrier gas passes into the gap 1012 between the second inner cylinder 1006 and the first inner cylinder 1004. The stream of carrier gas that passes into the gap 1012 is moving in a direction opposite to that of the ions passing outwardly through the same gap 1012, and thus acts to help desolvate the ions and to prevent neutrals from the needle 1010 from contaminating the portion of the carrier gas flow that passes along the analyzer region 1016.

Referring still to FIG. 10a, there are two approaches to providing a non-separated mixture of ions to a post-FAIMS device 1026, such as for instance one of a mass spectrometer, a further FAIMS device, or an ion detector as some non-limiting examples. In a first approach the asymmetric waveform is deactivated and the first inner cylinder 1004 and the outer cylinder 1002 held at a same voltage. In a second approach the asymmetric waveform is deactivated and the first inner cylinder 1004 is retracted away from the second inner cylinder 1006 so that the end of the first inner cylinder 1004 is no longer between the ion source 1010 and the ion outlet 1018. In both of these approaches the mixture of ions produced by the ion source 1010 is not separated by the FAIMS mechanism, and some of the non-separated mixture of ions exits through the ion outlet 1018. Of course, other mechanisms for relative selectivity of ion transmission may still exist, for example the relative rates of loss of various types of ions via diffusion may differ. When operating in these optional non-separating modes, the pathway between the ion source 1010 and the ion outlet 1018 is long and the efficiency of transmission of the ions is not high.

Figure 11:
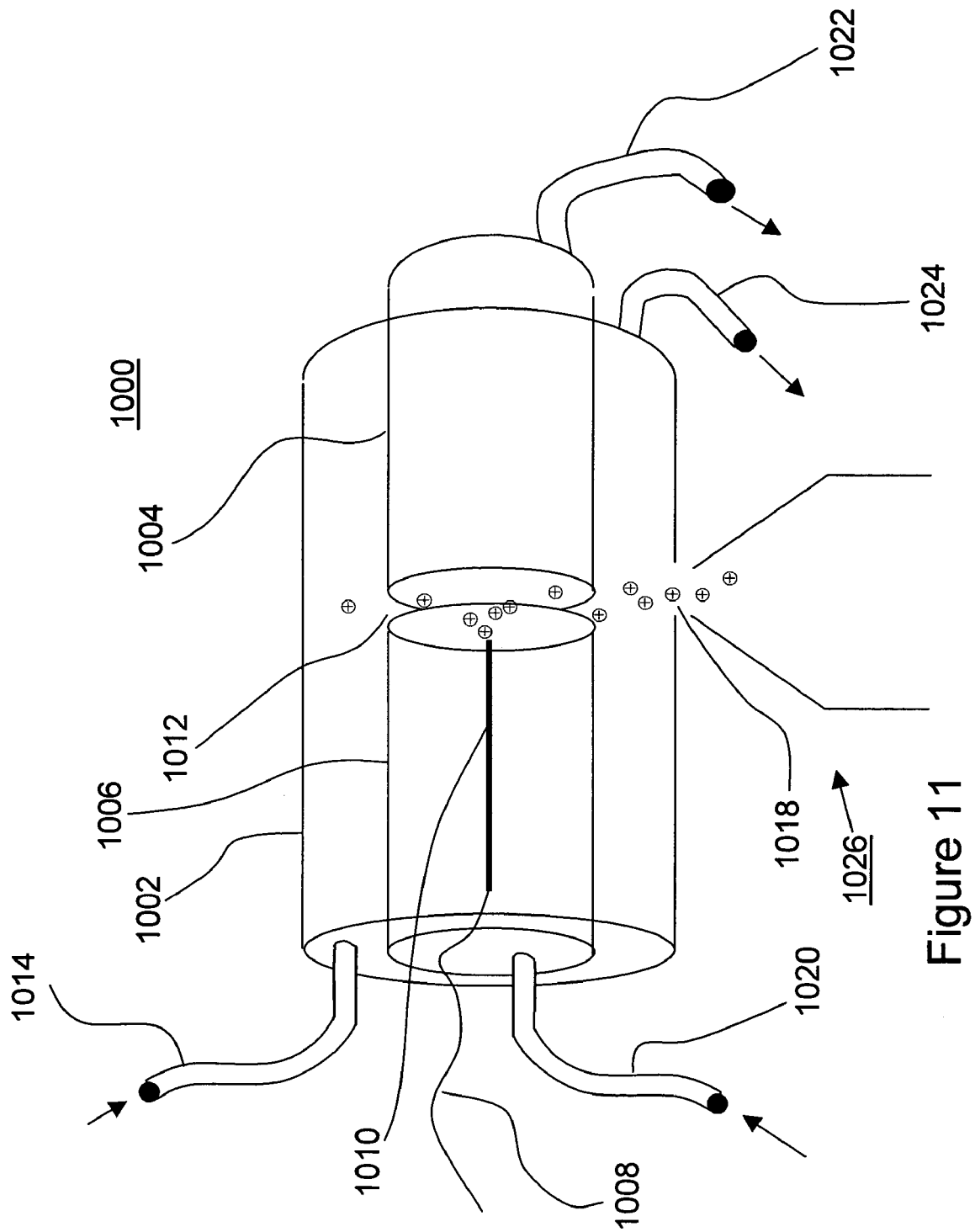
FIG. 11 is a side view of the FAIMS of FIG. 10a with the two shorter axially aligned cylinders translated longitudinally so that the gap between these cylinders is approximately adjacent to the ion outlet.

Referring now to FIG. 11, shown is a side view of the FAIMS of FIG. 10a with the first inner cylinder 1004 and the second inner cylinder 1006 translated longitudinally so that the gap 1012 between these cylinders is approximately adjacent to the ion outlet 1018. FIG. 11 illustrates the FAIMS system 1000 during non-separating, total ion transmission mode whereas FIG. 10a with the application of the asymmetric waveform and a dc compensation voltage illustrates the FAIMS system 1000 during the normal separating operating mode of FAIMS. The conversion between the non-separating and the normal operating mode is achieved via the translation of the first inner cylinder 1004, the second inner cylinder 1006, and the ionization source 1010, and via control of the above-mentioned applied voltages. To this end, a not illustrated controller including an actuator is provided. For instance, the actuator is similar to one of the actuators 328 or 634 as described above. These components are moved so that the gap 1012 becomes aligned with the ion outlet 1018 in the outer cylinder 1002. Accordingly, the actuator is for moving synchronously the first inner cylinder 1004, the second inner cylinder 1006 and the ionization source 1010. The sample delivery tube 1008 must have provision to remain connected during this translation, and similarly the sample gas delivery conduit 1020 and the sampler gas exit conduit 1022 are flexibly connected to support such translational motion of the inner components of FAIMS system 1000.

In FIG. 11, a flow of liquid sample is provided through the sample delivery tube 1008 to the tip of the ESI source needle 1010. Ions are produced and pushed outward radially because of the high voltage applied to the ESI source needle 1010. Appropriate voltages applied to the shorter second inner cylinder 1006 and the long outer cylinder 1002 drive the ions outwardly in a radial direction away from the source needle 1010 and through the gap 1012 between the shorter second inner cylinder 1006 and the longer first inner cylinder 1004. In this example, the appropriate voltage is applied to the first inner cylinder 1004 through not-illustrated electrical connections.

Referring still to FIG. 11, the ions pass radially outward through the gap 1012 and travel to the ion outlet 1018 along an average ion flow path that is substantially perpendicular to the cylinder surfaces. Accordingly, the length of the average ion flow path is approximately equal to the size of the annular space between an outer surface of the first inner cylinder 1004 and an inner surface of the long outer cylinder 1002. The average ion flow path does not include a component along a direction that is parallel to the cylinder surfaces, and as such the ions are not separated according to the FAIMS principle.

Figure 12:
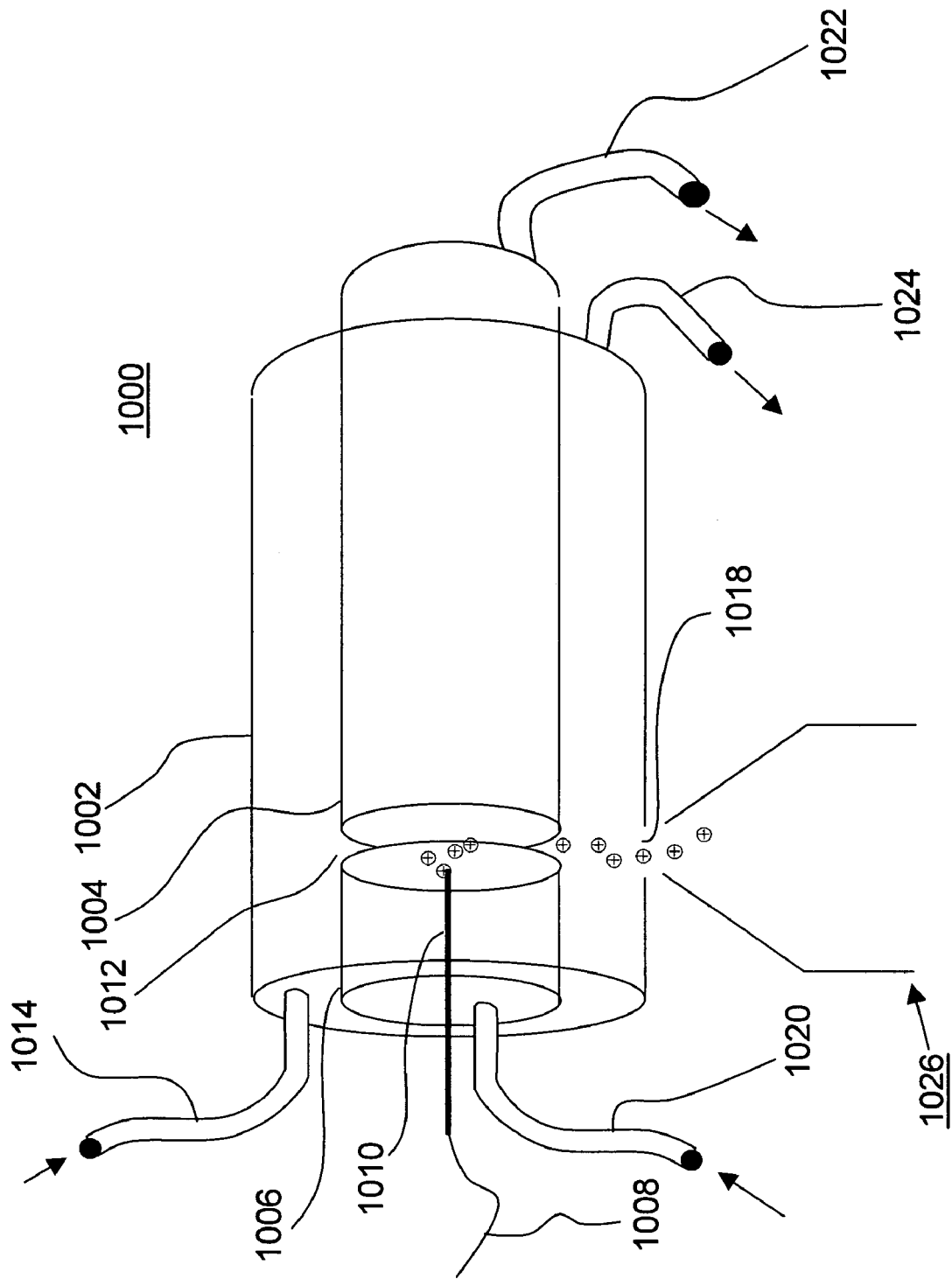
FIG. 12 is a side view of the FAIMS of FIG. 10a with the ion outlet proximate to the gap between the two shorter aligned cylinders.

Referring now to FIG. 12, shown is a side view of the FAIMS of FIG. 10a with the outer cylinder 1002 translated longitudinally so that the ion outlet 1018 is approximately adjacent to the gap 1012 between the first inner cylinder 1004 and the second inner cylinder 1006. FIG. 12 illustrates the FAIMS system 1000 during non-separating, total ion transmission mode whereas FIG. 10a with the application of an asymmetric waveform and a dc compensation voltage illustrates the FAIMS system 1000 during the normal separating operating mode of FAIMS. The conversion between the non-separating and the normal operating mode is achieved via the translation of the long outer cylinder 1002, as well as the post-FAIMS device 1026, such as for instance one of a mass spectrometer, a further FAIMS device, or an ion detector as some non-limiting examples. To this end, a not illustrated controller including an actuator is provided. For instance, the actuator is similar to one of the actuators 328 or 634 as described above. These components are moved so that the ion outlet 1018 becomes aligned with the gap 1012 between the first inner cylinder 1004 and the second inner cylinder 1006. Accordingly, the actuator is for moving synchronously the long outer cylinder 1006, and the post FAIMS device 1026. Of course, translation of heavier or bulkier post FAIMS devices, such as for instance a mass spectrometer, limits the applicability of this approach. Smaller and more compact post FAIMS devices, such as for instance a lightweight ion detector or another FAIMS device, are better suited for this approach.

Referring still to FIG. 12, the ions pass radially outward through the gap 1012 and travel to the ion outlet 1018 along an average ion flow path that is substantially perpendicular to the cylinder surfaces. Accordingly, the length of the average ion flow path is approximately equal to the size of the annular space between an outer surface of the first inner cylinder 1004 and an inner surface of the long outer cylinder 1002. The average ion flow path does not include a component along a direction that is parallel to the cylinder surfaces, and as such the ions are not separated according to the FAIMS principle.

FIG. 11 and FIG. 12 show two ways of relatively moving the ion outlet 1018 relative to the gap 1012. In FIG. 11, only the inner components are translated, which reduces complexity. In contrast, FIG. 12 requires translation of the post-FAIMS device and therefore is more complex depending on the post-FAIMS device. For ease of use, minimization of the number of components that require movement is desired. Furthermore, movement of heavier components, such as for instance the post FAIMS device 1026, is to be avoided when possible.

FIGS. 13a and 13b illustrate a FAIMS system 1300, in which the FAIMS electrodes are cylindrical in geometry, thereby providing the beneficial effects of ion focusing when operating in the normal FAIMS ion separating mode. In addition, a single electrode within FAIMS 1300 is readily translatable between two positions, one position that provides a FAIMS separation and a second position in which FAIMS separation is absent. It is beneficial that the ionization source, which is not shown in FIGS. 13a and 13b, is not mechanically moved. It is also beneficial that most of the FAIMS device is not moved and that the post-FAIMS system, which also is not shown in FIGS. 13a and 13b, is not moved during the change of FAIMS to non-FAIMS operating mode.

Referring now to FIG. 13a, a stream 1302 of ions from a not-illustrated ionization source pass through an ion inlet opening 1304 in a first curved electrode 1306. The curved electrode 1306 is spaced apart from a first curved surface 1308 of an intermediate electrode 1310. The ions pass through an inter-analyzer aperture 1312 in the intermediate electrode 1310. A third curved electrode 1314 is adjacent to a second curved surface 1316 of the intermediate electrode 1310. The stream of ions passes through an ion outlet opening 1318 through the third electrode 1314, and the stream of transmitted ions 1404 is delivered to an optional further analyzer, for example one of a FAIMS, a drift tube IMS, and a mass spectrometer as non-limiting examples.

FIG. 13b is a cross-sectional end perspective view of the FAIMS 1300 of FIG. 13a, with approximate alignment of the ion inlet 1304, the inter-analyzer aperture 1312 and the ion outlet 1318. FIG. 13b is taken by cutting through the FAIMS 1300 in a plane that passes through the aligned ion inlet 1304, the inter-analyzer opening 1312 and the ion outlet 1318, and in practice the device extends longitudinally on both sides of this plane. Not-shown insulating material supports the electrodes in the spaced apart arrangement that is shown in FIG. 13b, and provides gas-tight seals that prevent gas from escaping around the peripheral parts of the electrodes. The not-shown insulating material ensures that gas flows into FAIMS 1300 only through the ion inlet 1304 and flows out of FAIMS 1300 only through the ion outlet 1318.

Still referring to FIGS. 13a and 13b, although there are curved regions between the electrodes, the alignment of the ion inlet 1304, the inter-analyzer opening 1312 and the ion outlet 1318 results in ions crossing the regions between the electrodes in a radial direction relative to the curvatures of the electrodes. This differs from a conventional mode of operation of ion separation in FAIMS where the ions are carried along the space between the electrodes in a direction generally parallel to the surfaces of the electrodes. FIGS. 13a and 13b illustrate the FAIMS device 1300 operating in a non-separating, total ion transmission mode. The distance between the ion inlet 1304 and the ion outlet 1318 is minimized.

FIGS. 14a and 14b illustrate the FAIMS 1300 of FIG. 13a, but with the intermediate electrode 1310 translated along the longitudinal direction so that the position of the inter-analyzer opening 1312 is displaced a distance "A" from the line-of-sight pathway between the ion inlet 1304 and the ion outlet 1318. FIG. 14b also illustrates an average ion flow path followed by a stream of ions 1402 and passing through ion inlet 1304, along a path approximately parallel to the surfaces of the electrodes to the inter-analyzer opening 1312, passing through the inter-analyzer opening 1312 and again following a path approximately parallel to the surfaces of the electrodes to the ion outlet 1318. The stream of ions 1404 that has passed through the ion outlet 1318 is then provided to a further not-shown post-FAIMS device that may optionally be one of a mass spectrometer, an ion detector, a drift type ion mobility spectrometer, or to another FAIMS, as some non-limiting examples.

Still referring to FIGS. 14a and 14b, it is beneficial that the intermediate electrode 1310 is translatable for modifying the length of the path that the ions take when passing from the ion inlet 1304 to the ion outlet 1318. The displacement of the inter-analyzer opening 1312 in FIGS. 14a and 14b results in a pathway approximately twice the displacement "A". In normal ion separation mode with the asymmetric waveform and dc compensating offset voltages applied to the intermediate electrode 1310, the FAIMS separation takes place as the ions are carried along this pathway from the ion inlet 1304 to the inter-analyzer opening 1312, and from the inter-analyzer opening 1312 to the ion outlet 1318. The electric fields vary in strength in the radial direction from each of the curved electrodes 1306 and 1314 towards the intermediate electrode 1310. This variation in electric field strength, E/N, and the applied asymmetric waveform establishes the ion focusing mechanism that is beneficially used to minimize the loss of ions of interest, which are transmitted through FAIMS 1300 at the appropriate DV and CV, to the electrode surfaces.

Still referring to FIGS. 14a and 14b, the time required for transit through this device is beneficially controlled by the relative offset distance "A" that the ions travel to pass through the intermediate electrode. A longer distance "A" improves ion separation, but also increases the period of time required for ions to travel through the FAIMS device. Similarly, the effective separation may be reduced for a beneficial change in the time response of the device when the distance "A" in FIGS. 14a and 14b is minimized. FIGS. 13a and 13b illustrate the condition at the extreme of "A" being nearly zero such that the separation is not effective and the device operates in total ion transmission mode, where specificity is low. In this non-separating mode that is illustrated in FIGS. 13a and 13b, the asymmetric waveform optionally is turned off, and dc voltages are applied to the three electrodes of FAIMS 1300 to maximize ion transmission efficiency between the ion inlet 1304 and the ion outlet 1318.

Figure 15A:
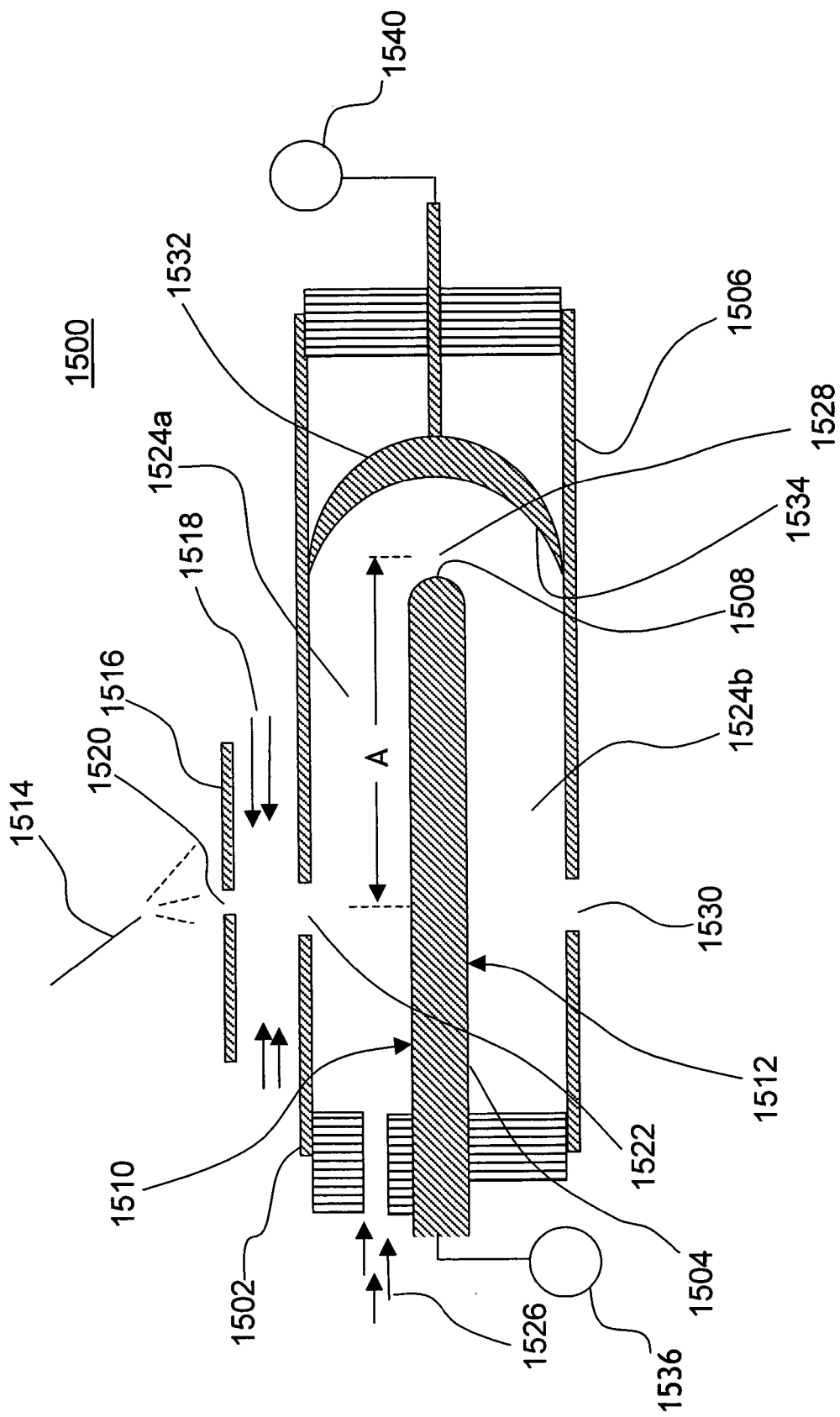
FIG. 15a is a longitudinal cross-sectional view of a parallel-plate geometry FAIMS, with a displacement A between an ion inlet and a transition point and between the transition point and an ion outlet.

Referring now to FIG. 15a, shown is a longitudinal cross-sectional view of a parallel plate FAIMS 1500 including three stacked plates 1502, 1504 and 1506, disposed in a spaced-apart relationship. The central electrode 1504 includes a curved terminus 1508 that is continuous with a first electrode surface 1510 on one side of the electrode 1504 and with a second electrode surface 1512 on a second side of the electrode 1504 that is opposite the first side. Ions that are produced by ion source 1514 drift toward a curtain plate 1516. A flow of a curtain gas 1518, introduced below the curtain plate 1516, divides into two portions, one of which flows outwardly through an aperture 1520 in the curtain plate 1516 so as to prevent neutrals and droplets from entering the curtain plate aperture 1520. Ions are driven against this flow of gas by a voltage gradient that is established between the ion source 1514 and the curtain plate 1516. A field generated by a voltage difference between the curtain plate 1516 and the FAIMS plate 1502 pushes ions that pass through the aperture 1520 in the curtain plate 1516 towards the ion inlet 1522 of FAIMS 1500. The second portion of the curtain gas flows into the ion inlet 1522 and carries the ions along the length of the FAIMS electrodes through the analyzer region 1524a. A second carrier gas flow 1526 is optionally provided to assist in carrying the ions along the analyzer region 1524a. The ions travel an approximate distance indicated as "A" from the inlet 1522 to a transition point 1528, defined near the end of the terminus 1508. The ions are carried by the flow of gas past the transition point 1528 and around the curved terminus 1508 into a second analyzer region 1524b, and travel a second distance "A" to the ion outlet 1530. Since the asymmetric waveform and dc offset voltage is applied to the plate 1504 from power supply 1536, and assuming that the distance between plate 1502 and 1504 and the distance between plate 1504 and 1506 are approximately equal, both analyzer regions 1524a and 1524b operate to separate ions in a substantially equivalent way. Optionally, to improve ion separation resolution, slightly different conditions are imposed in these analyzer regions 1524a and 1524b, by varying electrode spacing, by application of different dc voltages to plates 1502 and 1506 or by the application of different temperatures to the plates 1502 and 1506.

Referring still to FIG. 15a, a curved electrode 1532 is disposed between the plates 1502 and 1506. The curved electrode 1532 includes a concave electrode surface 1534 facing the curved terminus 1508. The concave electrode surface 1534 maintains an approximately constant spacing to the plate 1504 between the analyzer region 1524a and the analyzer region 1524b. Optionally, the curved electrode 1532 is electrically isolated from the electrode plates 1502 and 1506. For instance, not illustrated electrically insulating material is disposed between the ends of the curved electrode 1532 and the plates 1502 and 1506. Of course, the electrically insulating material forms a gas-tight seal to the plates 1502 and 1506 whilst supporting sliding motion of the curved electrode 1532. In that case, a dc voltage applied by optional power supply 1534 is independent of applied dc voltages to plates 1502 and 1506. By selection of appropriate applied dc voltages to each of the plates, optimized conditions for transmitting ions past the transition point 1528 are provided. Alternatively, the curved electrode 1532 is in electrical contact with plates 1502 and 1506.

Figure 15B:
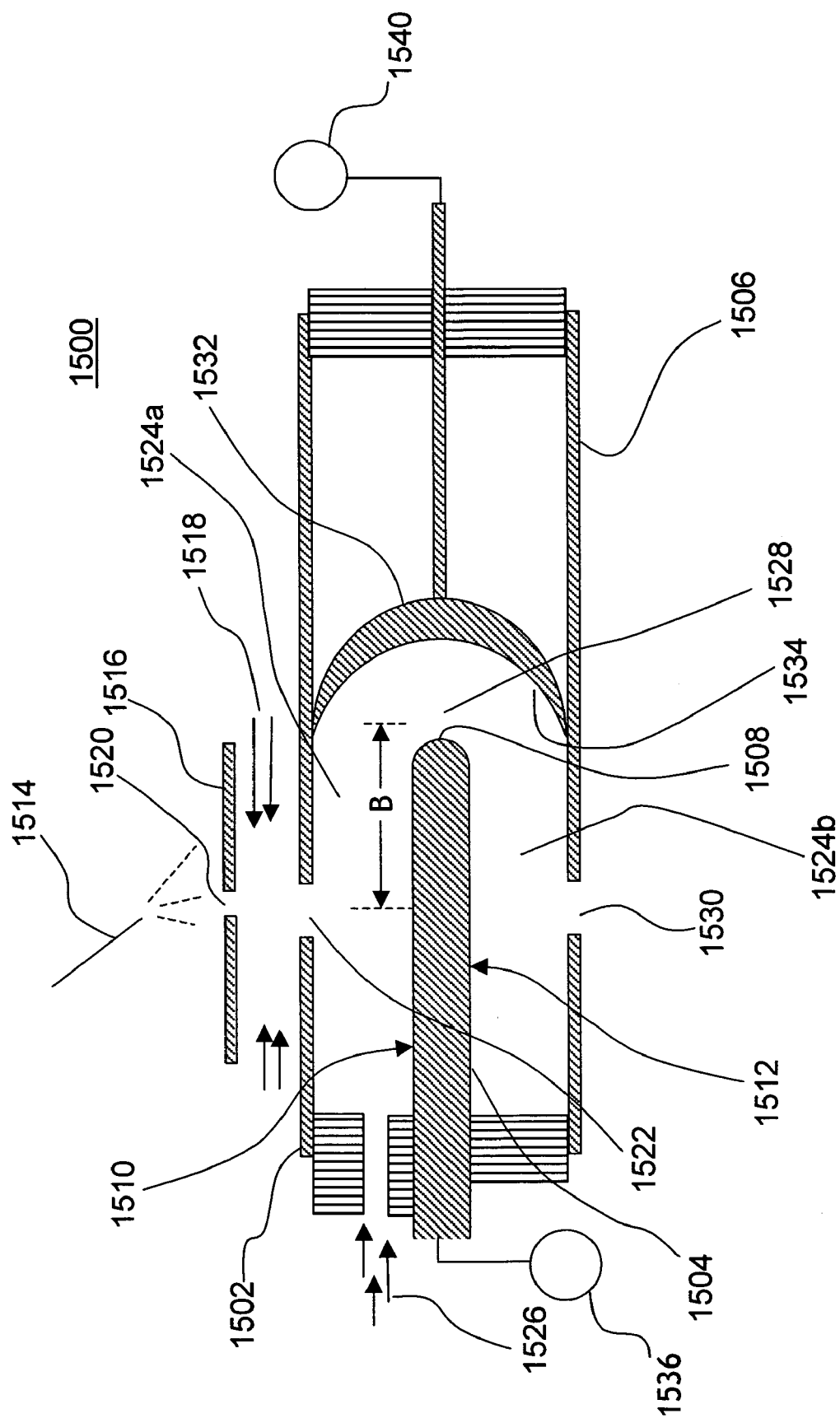
FIG. 15b is a longitudinal cross-sectional view of the parallel-plate geometry FAIMS of FIG. 15a, with a displacement B between the ion inlet and the transition point and between the transition point and the ion outlet.

Referring now to FIG. 15b, shown is a longitudinal cross-sectional view of the FAIMS 1500 of FIG. 15a, with the central electrode 1504 and curved electrode 1532 translated relative to plates 1502 and 1506, such that the position of the transition point 1528 is displaced a distance "B" from the ion inlet 1522 and the ion outlet 1530. In particular, the central plate 1504 and curved electrode 1532 are translated by equal amounts along a same direction, such that the spacing between the curved terminus 1508 and the concave surface 1534 is unchanged from the spacing shown in FIG. 15a. Ions traveling along an average ion flow path between the ion inlet 1522 and the ion outlet 1530 traverse a distance of approximately twice the distance "B" plus the thickness of plate 1504. Accordingly, given substantially identical operating conditions, ions spend less time being separated when the system 1500 is in the state shown in FIG. 15b compared to the state shown in FIG. 15a, in which ions traverse a greater distance of approximately twice the distance "A" plus the thickness of plate 1504. Thus, ions having similar FAIMS separation properties may be separated when the system 1500 is in the state shown in FIG. 15a, but may not be separated when the system 1500 is in the state shown in FIG. 15b. As such, varying the distance between the transition point 1528 and ion inlet 1522 and ion outlet 1530 supports controllably varying specificity of a FAIMS-based ion separation.

Figure 15C:
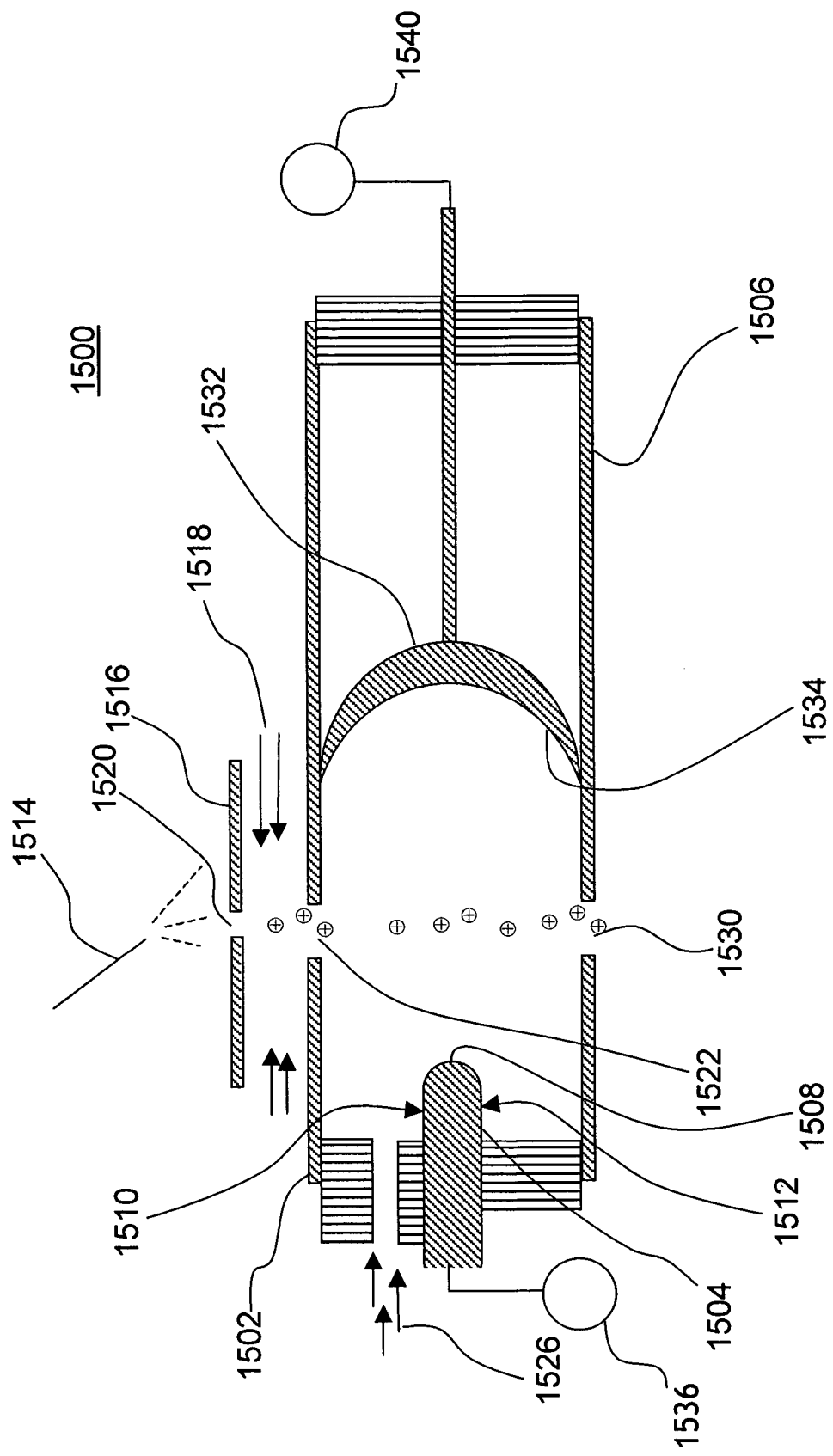
FIG. 15c is a longitudinal cross-sectional view of the parallel-plate geometry FAIMS of FIG. 15a, in a total ion transmission operating mode.

Referring now to FIG. 15c, shown is a longitudinal cross-sectional view of the FAIMS 1500 of FIG. 15a, with the plate 1504 and curved electrode 1532 translated away from each other, such that the plate 1504 is no longer disposed in the line-of-sight pathway between the ion inlet 1522 and the ion outlet 1530. In the state of system 1500 shown in FIG. 15c, ions pass along a shortest ion pathway between the ion inlet 1522 and the ion outlet 1530. Optionally, the asymmetric waveform applied to plate 1504 is shut off. Further optionally, an electric field gradient is established between plate 1502 and plate 1506 for driving ions from the ion inlet 1522 to the ion outlet 1530.

Referring still to FIG. 15c, a not illustrated controller including an actuator for translating the plate 1504 independently of the curved electrode 1532 is provided. Optionally, the actuator also supports synchronized translation of the plate 1504 and of the curved electrode 1532, so as to vary the distance between transition point 1528 and the ion inlet 1522 and the ion outlet 1530, as shown in FIGS. 15a and 15b, whilst maintaining approximately the same spacing from the curved terminus 1508 to the concave surface 1534.

Figure 16:
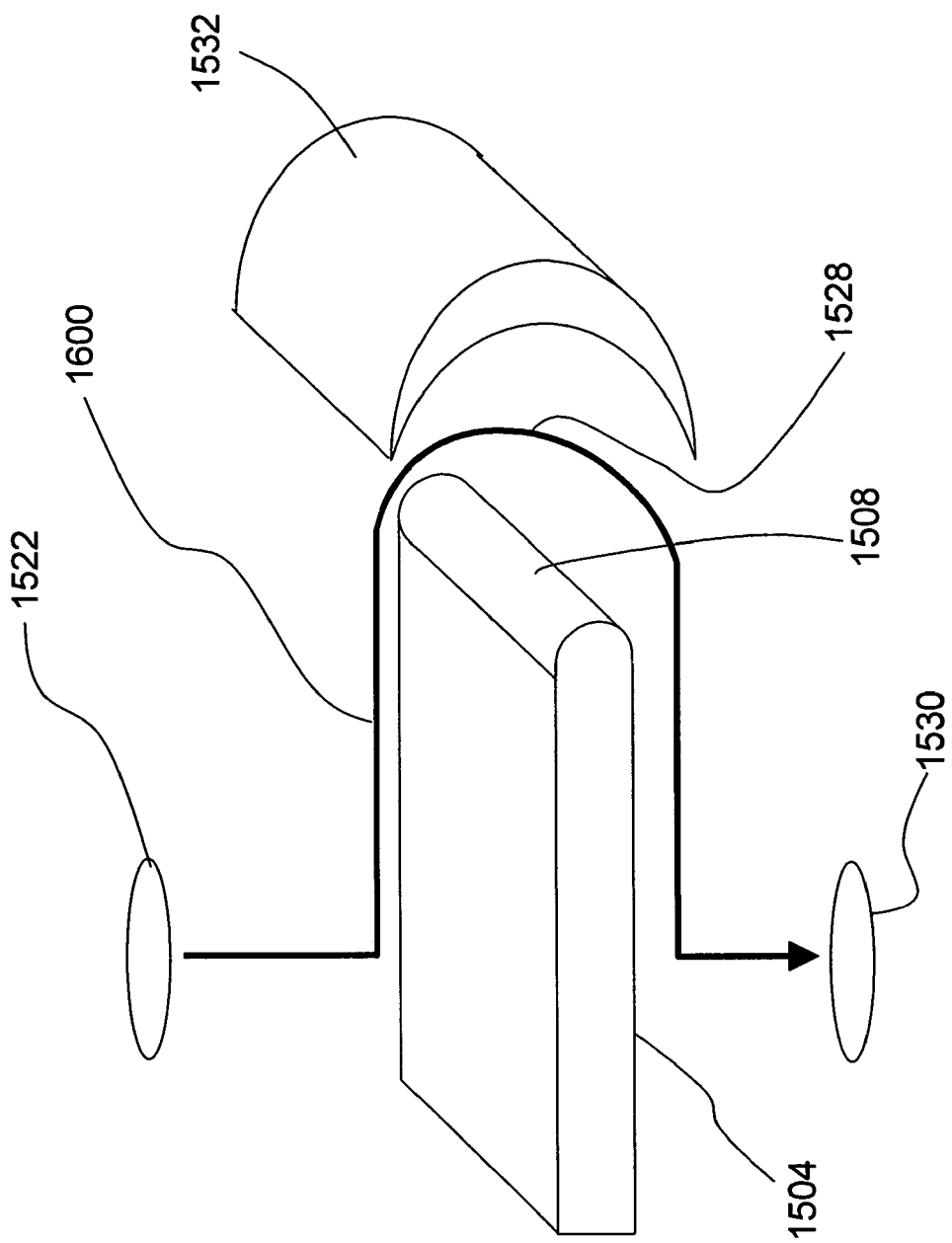
FIG. 16 is a perspective view of the middle plate of the FAIMS system of FIG. 15a disposed in a spaced apart relationship relative to the curved electrode of the FAIMS system of FIG. 15a, and showing an average ion flow path.

Referring now to FIG. 16, shown is a perspective view of the plate 1504 disposed in a spaced apart relationship relative to the curved electrode 1532. An average ion flow path 1600 is shown between the ion inlet 1522 and the ion outlet 1530, and passing through the transition point 1528.

Optionally, a form of side-to-side FAIMS is obtained by modification of the device shown at FIGS. 15a-15c. For instance, the plate 1504 is modified such that a second curved terminus is provided at an end of the plate 1504 opposite the curved terminus 1508. A second concave surface is disposed adjacent the second curved terminus, and the plate 1504 arranged approximately symmetrically with respect to a line passing through the ion inlet 1522 and the ion outlet 1530. In this not illustrated alternative embodiment, a second average ion flow path is defined between the ion inlet 1522 and the ion outlet 1530 that passes through a second transition point adjacent to the second curved terminus. Optionally, during use the modified plate is translated along one direction or the other, parallel to the plates 1502 and 1506. In this way, one of the average ion flow paths is lengthened, whilst the second average ion flow path is shortened. Alternatively, the modified plate is expandable, such that each of the two average ion flow paths is independently variable. Of course, a system including an expandable electrode plate is complicated, and provisions must be made to support the electrode plate and to ensure proper gas flow directionality.

Figure 17:
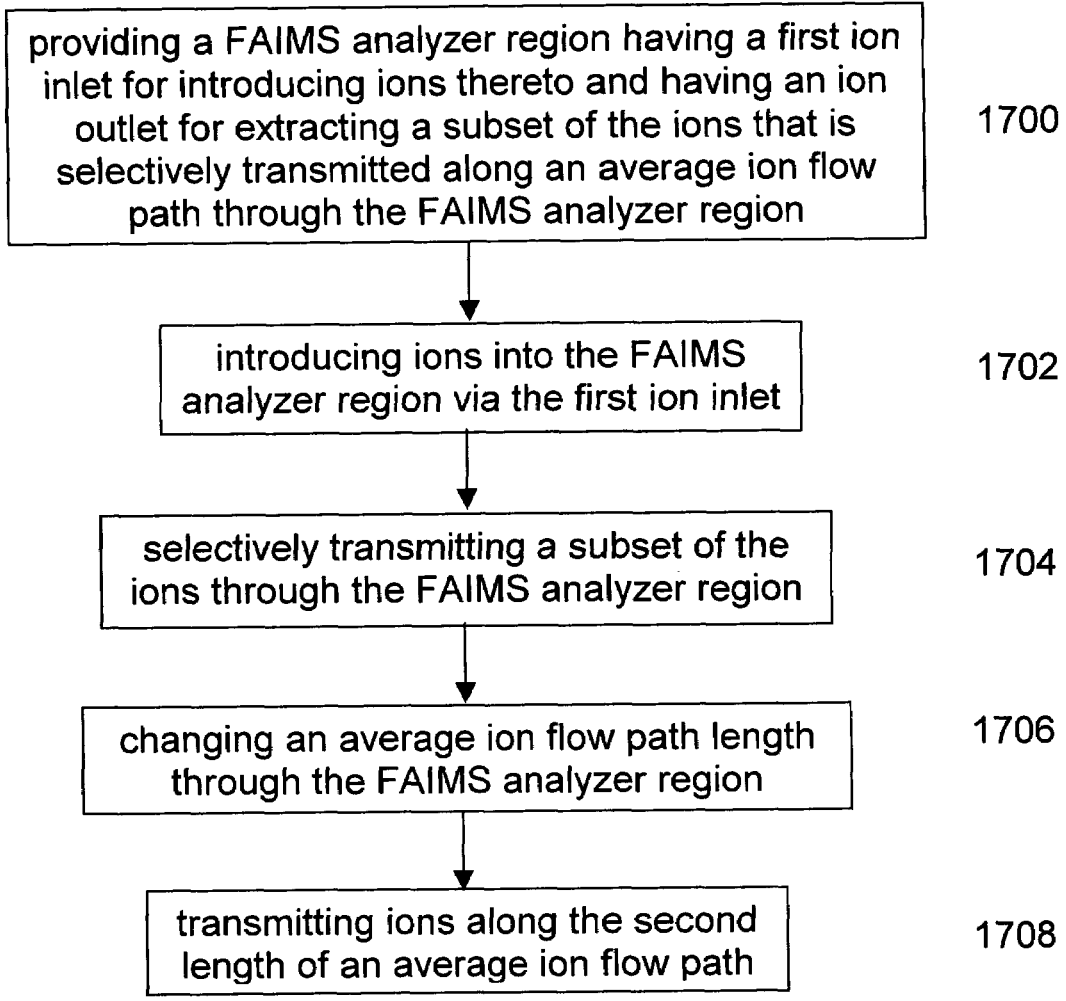
FIG. 17 is a simplified flow diagram of a method for controllably varying specificity of a FAIMS-based ion separation according to an embodiment of the instant invention.

Referring now to FIG. 17, shown is a simplified flow diagram of a method for controllably varying specificity of a FAIMS-based ion separation according to an embodiment of the instant invention. At step 1700 a FAIMS analyzer region is provided. The FAIMS analyzer region including a first ion inlet for introducing ions thereto and an ion outlet for extracting a subset of the ions that is selectively transmitted along an average ion flow path through the FAIMS analyzer region. At step 1702 ions are introduced into the FAIMS analyzer region via the first ion inlet. At step 1704 a subset of the ions is selectively transmitted through the FAIMS analyzer region along a first length of an average ion flow path. At step 1706 an average ion flow path length through the FAIMS analyzer region is changed. At step 1708 ions are transmitted along the second length of an average ion flow path.

Figure 18:
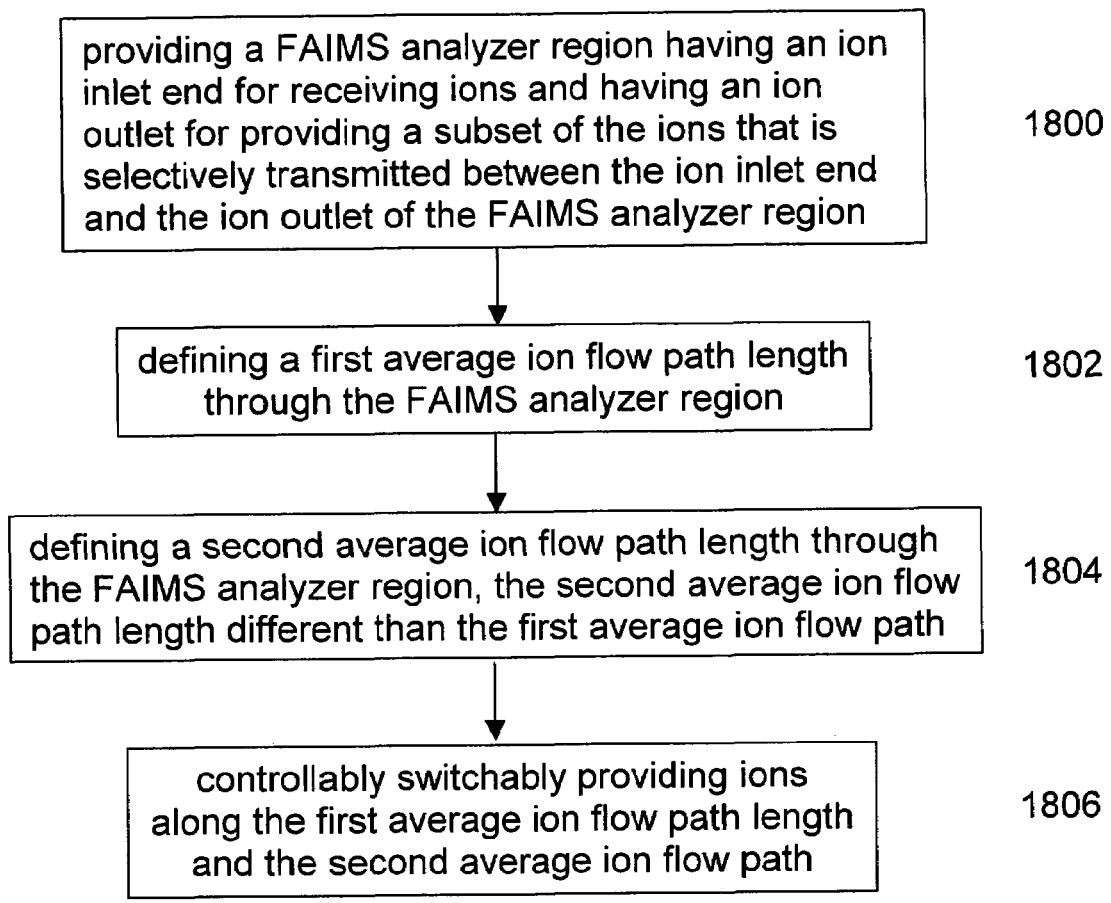
FIG. 18 is a simplified flow diagram of another method for controllably varying specificity of a FAIMS-based ion separation according to an embodiment of the instant invention.

Referring now to FIG. 18, shown is method for controllably varying specificity of a FAIMS-based ion separation according to another embodiment of the instant invention. At step 1800 a FAIMS analyzer region is provided. The FAIMS analyzer region including an ion inlet end for receiving ions and an ion outlet for providing a subset of the ions that is selectively transmitted between the ion inlet end and the ion outlet of the FAIMS analyzer region. At step 1802 a first average ion flow path length is defined through the FAIMS analyzer region. At step 1804 a second average ion flow path length is defined through the FAIMS analyzer region, the second average ion flow path length different than the first average ion flow path length. At step 1806 ions are provided along the first average ion flow path length and the second average ion flow path length in a controllably switchable manner.

Figure 19:
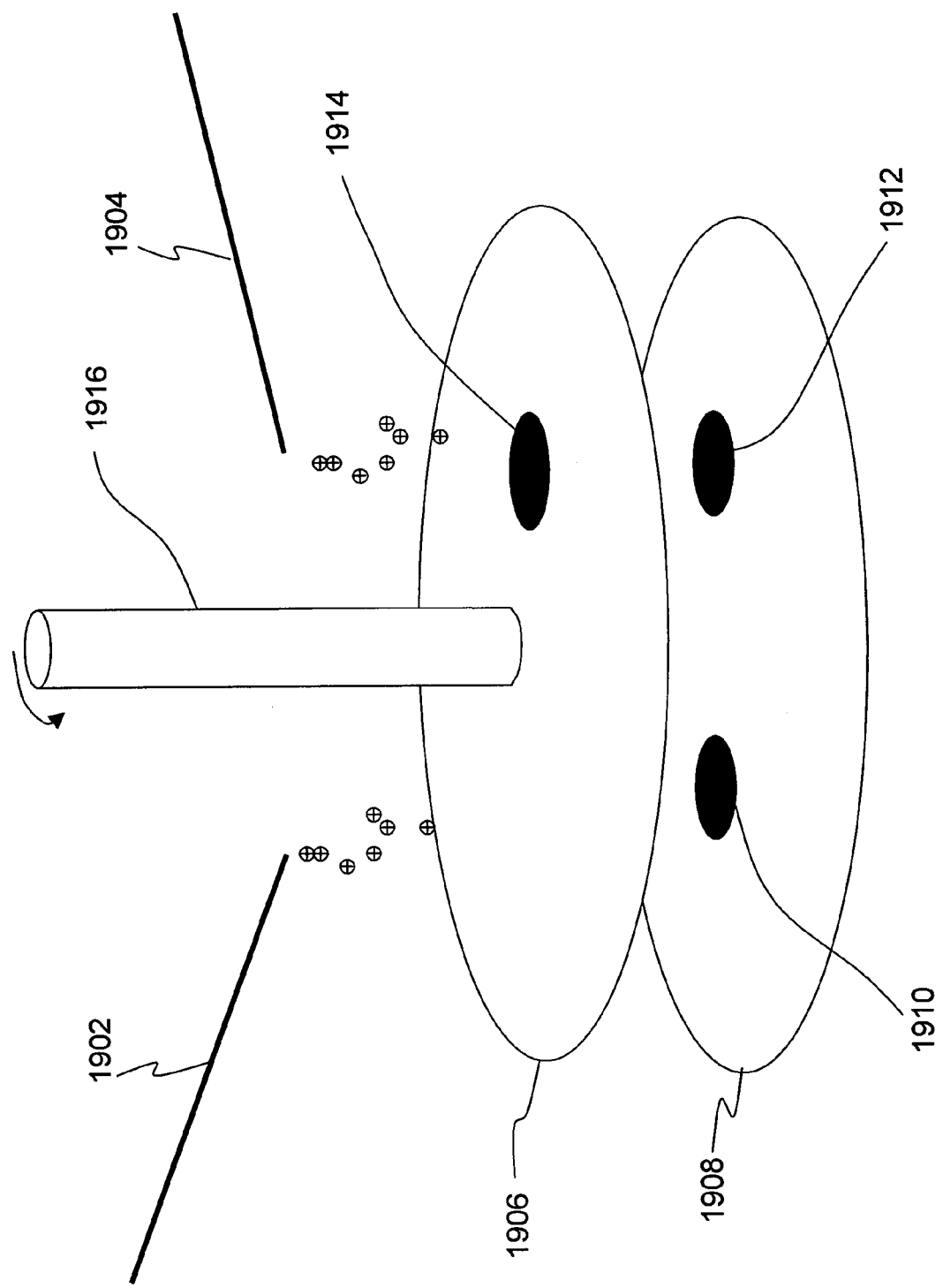
FIG. 19 shows a side view of a single-hole selector electrode according to an embodiment of the instant invention.

FIG. 19 is a schematic diagram that shows two atmospheric pressure ionization sources, in the form of a first electrospray needle 1902 and a second electrospray needle 1904, spraying ions toward a single-hole selector electrode 1906 that is positioned adjacent and parallel to a lower plate 1908 which has two openings 1910 and 1912 defined therethrough. Lower plate 1908 with the two openings 1910 and 1912 is a portion of one of a curtain plate and an outer electrode of a not illustrated FAIMS analyzer. Both cases will be considered in greater detail, below. The single-hole selector electrode 1906 includes a single opening 1914 defined therethrough and is mounted to a drive shaft 1916.

Figure 20A:
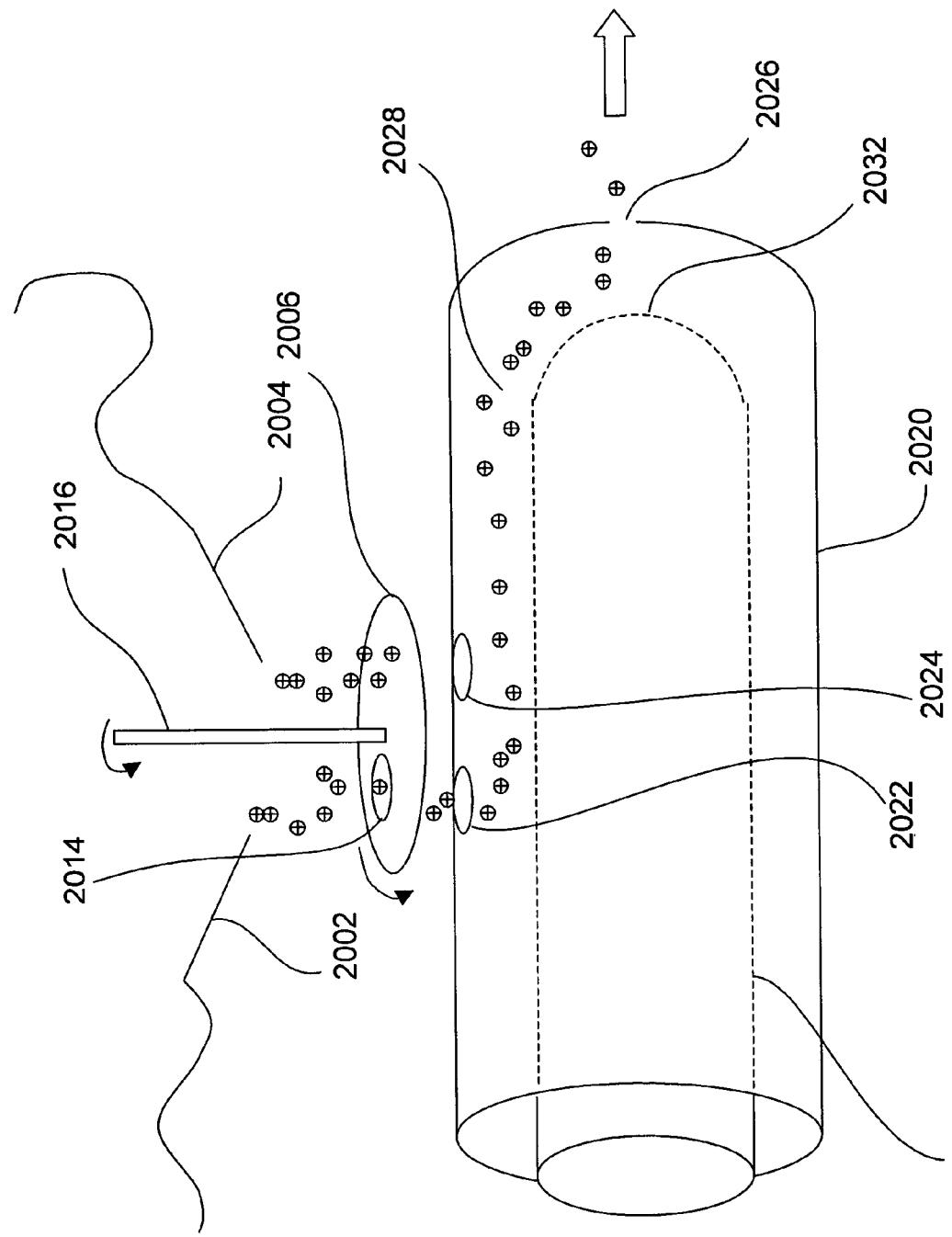
FIG. 20a is a schematic diagram of a single-hole selector electrode disposed adjacent and parallel to an outer electrode of a FAIMS analyzer, in a condition for introducing ions via a first ion inlet orifice.

Referring now to FIG. 20a, shown is a single-hole selector electrode disposed adjacent and parallel to an outer electrode of FAIMS. Elements labeled with the same numerals have the same function as those illustrated in FIG. 19. In FIG. 20a, the outer electrode 2020 of FAIMS has two ion inlet orifices 2022 and 2024 defined therethrough and also defines an ion outlet orifice 2026. An analyzer region 2028 is defined by a space between the outer electrode 2020 and an inner electrode 2030 of the FAIMS. The inner electrode 2030 includes a domed terminus 2032 for directing ions along an average ion flow path within the analyzer region 2028 that passes outwardly through the ion outlet orifice 2026.

In the system shown in FIG. 20a, both the first electrospray needle 2002 and the second electrospray needle 2004 are in continuous operation. The opening 2014 in the single-hole selector electrode 2006 is controllably alignable with the first ion inlet orifice 2022 or the second ion inlet orifice 2024 by rotation of the single-hole selector electrode 2006 about a rotation axis aligned with the drive shaft 2016. For instance, a not illustrated motor or other mechanical device actuates the drive shaft 2016 to rotate the single-hole selector electrode 2006 to adopt one of two possible rotational orientations. In each orientation the single opening 2014 is positioned adjacent to one of the ion inlet orifices 2022 and 2204 into FAIMS. By positioning this selector electrode, the user has the option of introducing ions from either, but not both, ion sources 2002 and 2004 into the FAIMS system at a time.

Referring still to FIG. 20a, the opening 2014 is positioned to allow ions from the first electrospray needle 2002 to pass into the analyzer region 2028. Accordingly, a mixture of ions including different types of ions including an ion type of interest is introduced into the analyzer region 2028 in FIG. 20a. The ions of the mixture are separated according to the FAIMS principle as they traverse the analyzer region 2028, and the ions passing out of FAIMS via the ion outlet orifice 2026 are enriched in the ion type of interest. Types of ions other than the ion type of interest are selectively lost as a result of collisions with an electrode surface of the FAIMS. Ions produced by the second ionization source 2004 impinge upon the single-hole selector electrode 2006 at a point away from the opening 2014 and are neutralized. Accordingly, in FIG. 20a ions from the second ionization source 2004 do not enter the FAIMS analyzer region 2028.

Figure 20B:
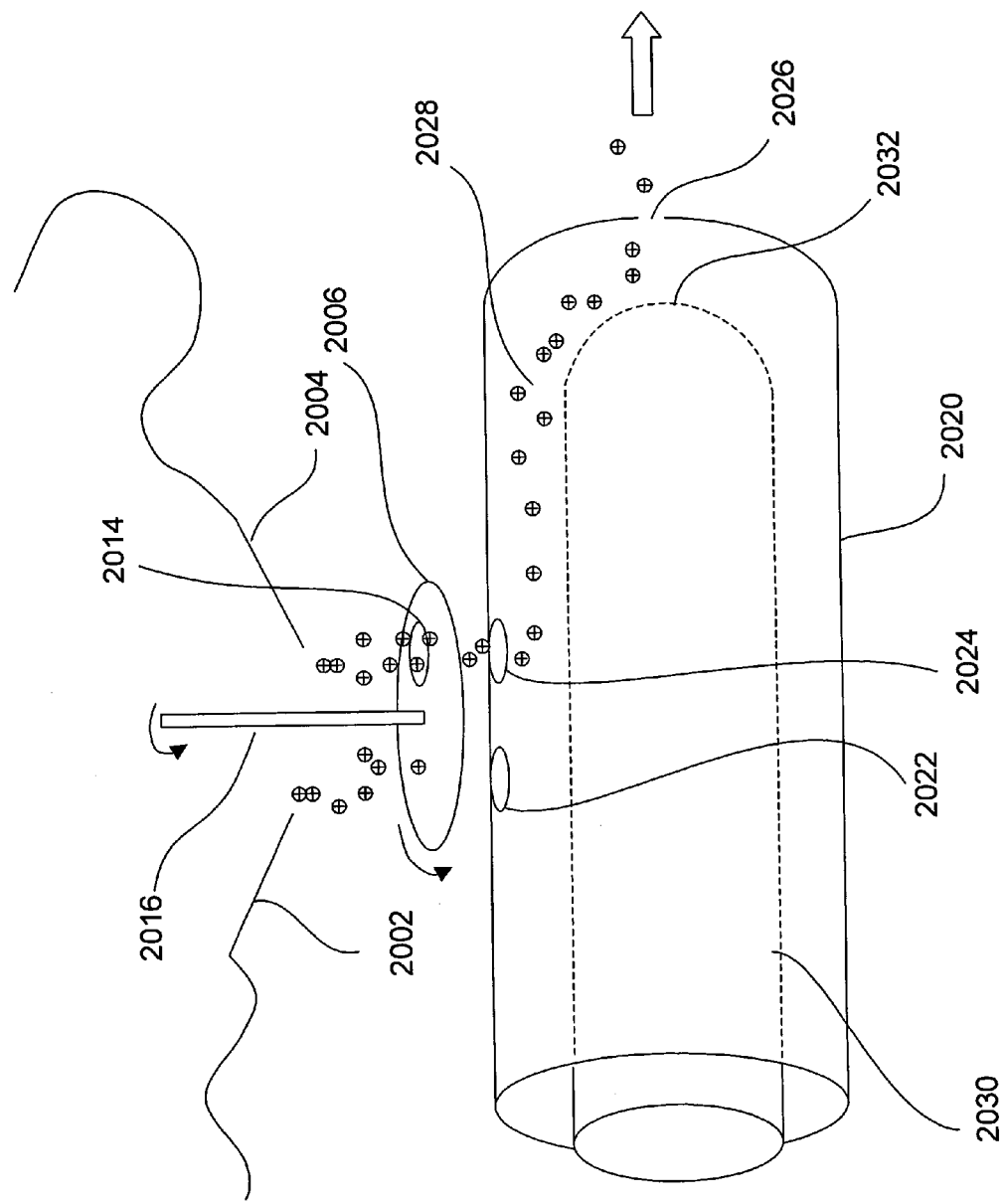
FIG. 20b is a schematic diagram of a single-hole selector electrode disposed adjacent and parallel to an outer electrode of a FAIMS analyzer, in a condition for introducing ions via a second ion inlet orifice.

Referring now to FIG. 20b, shown is the system of FIG. 20a but with the opening 2014 positioned to allow ions from the second electrospray needle 2004 to pass into the analyzer region 2028. Accordingly, a mixture of ions including different types of ions including an ion type of interest is introduced into the analyzer region 2028 in FIG. 20b. The ions of the mixture are separated according to the FAIMS principle as they traverse the analyzer region 2028, and the ions passing out of FAIMS via the ion outlet orifice 2026 are enriched in the ion type of interest. Types of ions other than the ion type of interest are selectively lost as a result of collisions with an electrode surface of the FAIMS. Ions produced by the first ionization source 2002 impinge upon the single-hole selector electrode 2006 at a point away from the opening 2014 and are neutralized. Accordingly, in FIG. 20b ions from the first ionization source 2002 do not enter the FAIMS analyzer region 2028.

Advantageously, the system shown at FIGS. 20a and 20b supports rapid sequencing between different ionization sources and/or different samples. For instance, optionally the ion type of interest produced by the first ionization source 2002 and the ion type of interest produced by the second ionization source 2004 are different types of ions. Further optionally, the first ionization source 2002 and the second ionization source 2004 are different types of ionization sources. Still further optionally, the sample is provided to each of the first ionization source 2002 and the second ionization source after separation using a chromatographic or electrophoretic technique. For instance, the first ionization source 2002 is in communication with an outlet of a HPLC system and the second ionization source is in communication with the outlet of a GC system. Advantageously, sample eluted from one of the HPLC system and the GC system may be analyzed using the FAIMS system during a time of no sample elution from the other one of the HPLC system and the GC system. Since analysis by chromatographic or electrophoretic techniques is characterized by long periods of separation followed by a relatively short elution period, multiplexing several chromatographic or electrophoretic systems into a single FAIMS with rapid switching between sources is efficient.

Figure 21A:
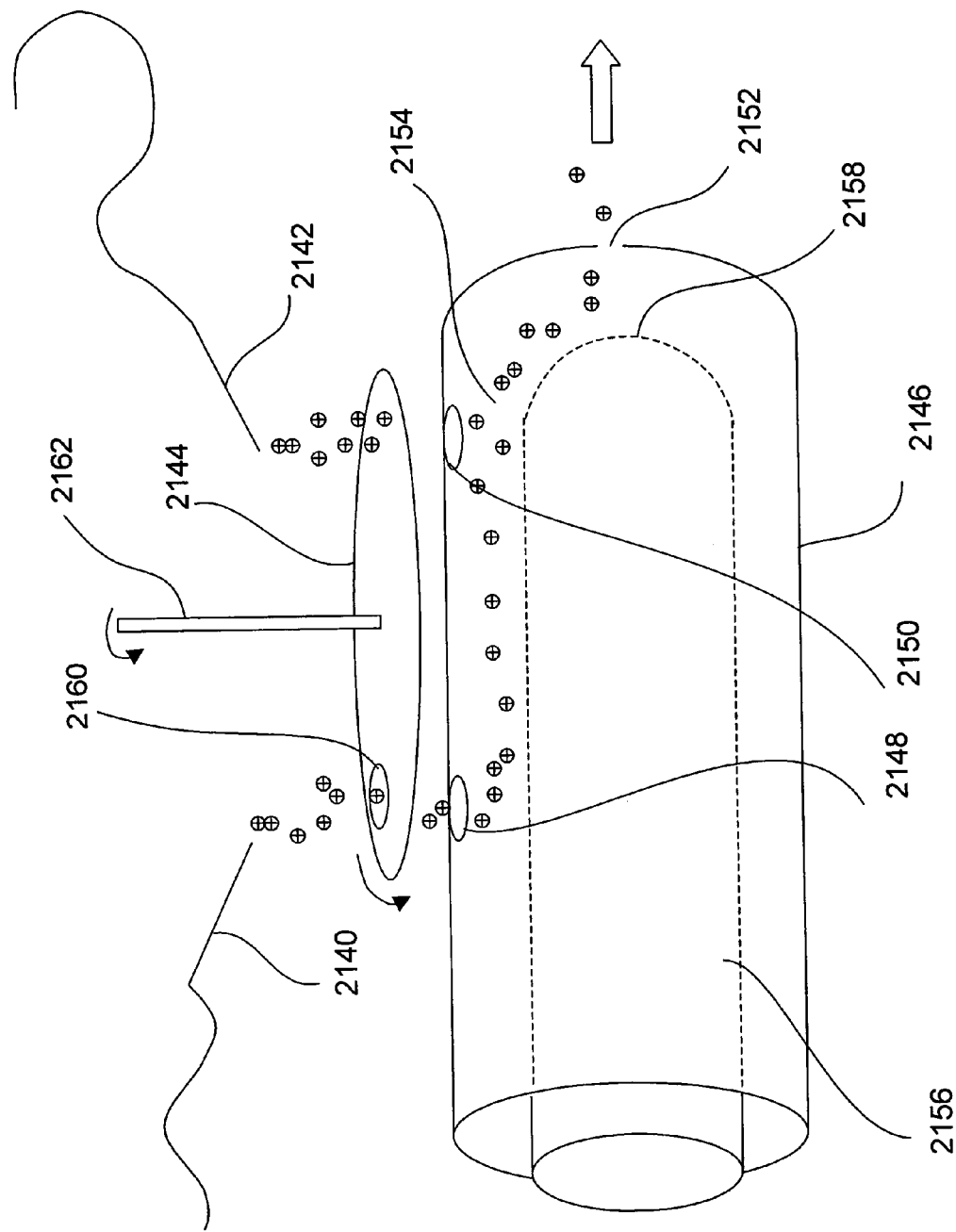
FIG. 21a is a schematic diagram of a single-hole selector electrode disposed adjacent and parallel to an outer electrode of a FAIMS analyzer, in a condition for selectively introducing ions in a FAIMS separation mode via a first ion inlet orifice into the FAIMS analyzer.
Figure 21B:
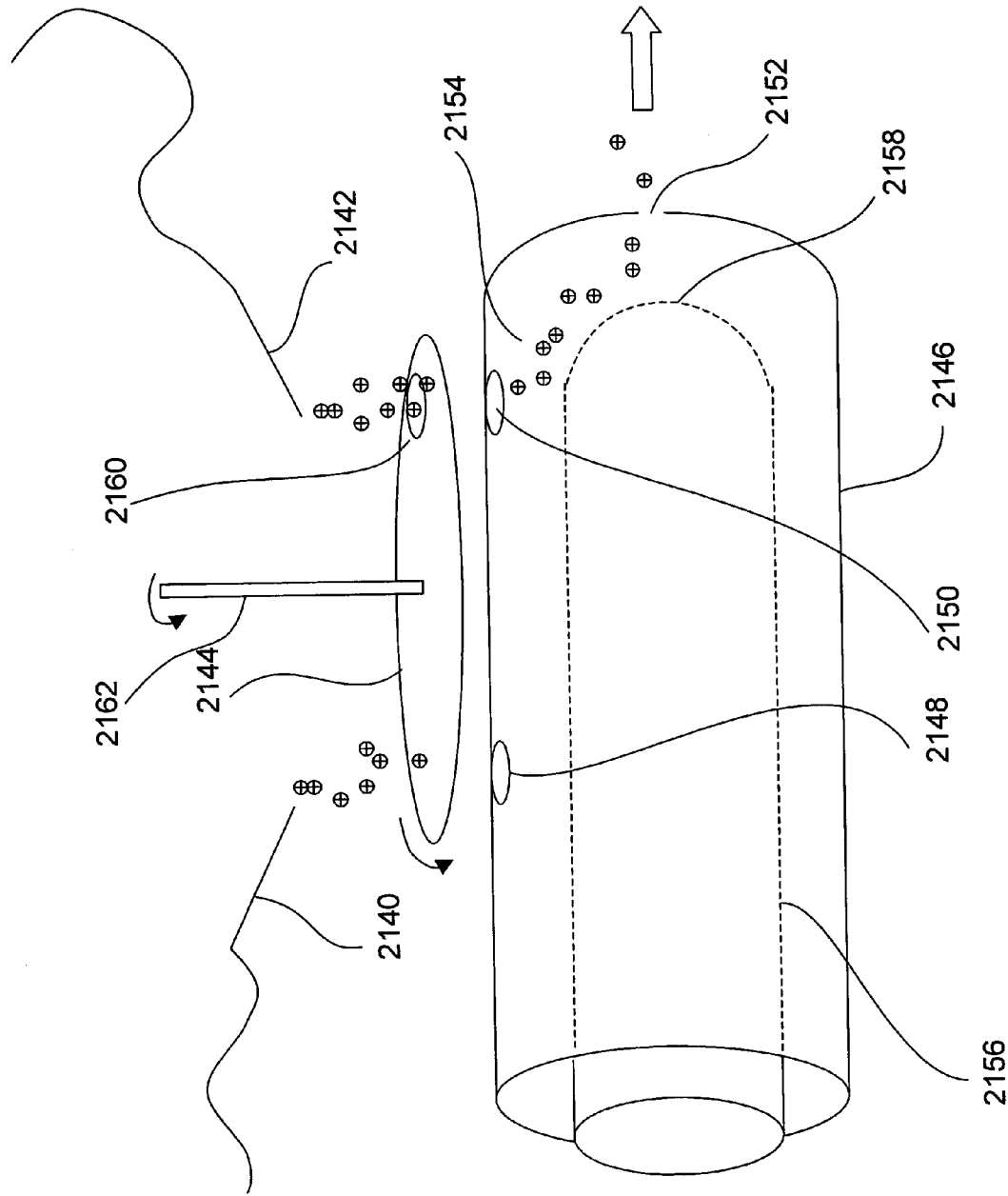
FIG. 21b is a schematic diagram of a single-hole selector electrode disposed adjacent and parallel to an outer electrode of a FAIMS analyzer, in a condition for selectively introducing ions in a total ion mode via a second ion inlet orifice into the FAIMS analyzer.

Referring now to FIGS. 21a and 21b, shown is a single-hole selector electrode disposed adjacent and parallel to an outer electrode of FAIMS. The system shown at FIGS. 21a and 21b is a special case of the system that was described with reference to FIGS. 20a and 20b, above. Two atmospheric pressure ionization sources, in the form of a first electrospray needle 2140 and a second electrospray needle 2142, are disposed for spraying ions toward a single-hole selector electrode 2144 that is positioned adjacent and parallel to an outer electrode 2146 of FAIMS. Two ion inlet orifices 2148 and 2150 are defined through the outer electrode 2146. The outer electrode 2146 also defines an ion outlet orifice 2152. An analyzer region 2154 is defined by a space between the outer electrode 2146 and an inner electrode 2156 of the FAIMS. The inner electrode 2156 includes a domed terminus 2158 for directing ions along an average ion flow path within the analyzer region 2154 that passes outwardly through the ion outlet orifice 2152.

Referring still to FIGS. 21a and 21b, the first ion inlet orifice 2148 is defined within a first portion of the outer electrode 2146 such that ions introduced via the first ion inlet orifice 2148 travel a first distance between the first ion inlet orifice 2148 and the ion outlet orifice 2152. In particular, the first distance is selected to provide an average ion flow path through the analyzer region 2154 that is sufficiently long to support at least partial separation of a first type of ion contained in a mixture of ions introduced via the first ion inlet orifice 2148, from a second type of ion contained in the same mixture. In other words, ions introduced into the analyzer region 2154 via the first ion inlet orifice 2148 are separated according to the FAIMS principle. Conversely, the second ion inlet orifice 2150 is defined within a second portion of the outer electrode 2146 such that ions introduced via the second ion inlet orifice 2150 travel a second distance between the second ion inlet orifice 2150 and the ion outlet orifice 2152, the second distance being shorter than the first distance. In particular, the second distance is selected to provide an average ion flow path through the analyzer region 2154 that is sufficiently short to support transmission of plural types of ions contained in a mixture of ions introduced via the second ion inlet orifice 2150. Optionally by removing the asymmetric waveform and compensation voltage difference between the FAIMS electrodes, and by providing a short ion path, the FAIMS separation mechanism is effectively "turned off" for those ions introduced into the analyzer region 2154 via the second ion inlet orifice 2150.

Referring still to FIGS. 21a and 21b, both the first electrospray needle 2140 and the second electrospray needle 2142 are in continuous operation. An opening 2160 in the single-hole selector electrode 2144 is selectably alignable with the first ion inlet orifice 2148 or the second ion inlet orifice 2150 by rotation of the single-hole selector electrode 2144 about a rotation axis aligned with drive shaft 2162. For instance, a not illustrated motor or other mechanical device actuates the drive shaft 2162 to rotate the single-hole selector electrode 2144 to adopt one of two possible rotational orientations. In each orientation the opening 2160 is positioned adjacent to one of the ion inlet orifices in FAIMS. By positioning this selector electrode, the user has the option of permitting ions from either, but not both, ion sources 2148 and 2150 to enter the FAIMS system.

One non-limiting example of an application for the system that is shown in FIGS. 21a and 21b is for supporting a "total ion" mode of operation with the electric fields removed, and optionally a partial-separation FAIMS mode of operation without the need for changing electric field conditions within the FAIMS analyzer region 2154. Another non-limiting example of an application for the system that is shown in FIGS. 21a and 21b is for supporting use of a LockMass™ or other calibration compound.

In the "total ion" mode of operation both the first electrospray needle 2140 and the second electrospray needle 2142 are producing ions from a same sample material. As is shown at FIG. 21a, when the opening 2160 of the single-hole selector electrode 2144 is aligned with the first ion inlet orifice 2148, a mixture of ions is introduced via the first ion inlet orifice 2148 and some types of ions are selectively transmitted through the analyzer region 2154 to the ion outlet orifice 2152. For a particular combination of applied asymmetric waveform and compensation voltages, only one or a relatively few types of ions are expected to be transmitted between the first ion inlet orifice 2148 and the ion outlet orifice 2152. However, when as is shown at FIG. 21*b* the opening 2160 of the single-hole selector electrode 2144 is aligned with the second ion inlet orifice 2150, a mixture of ions is introduced via the second ion inlet orifice 2150. In this second orientation of the selector electrode, the voltages applied to the FAIMS electrodes are optionally removed, and may be replaced with voltages that result in very low electric fields in the analyzer region. Since the distance between the second ion inlet orifice 2150 and the ion outlet 2152 is short, substantially all types of ions are transmitted between the second ion inlet orifice 2150 and the ion outlet orifice 2152. Optionally, the applied asymmetric waveform and compensation voltages may remain applied. In this case some separation will proceed, but with limited effectiveness because of the short distance between the second ion inlet orifice 2150 and the ion outlet orifice 2152.

Another non-limiting example of an application for the system that is shown in FIGS. 21*a* and 21*b* is for supporting use of a LockMass™ or other calibration compounds. This operation is required in specialized situations where very high mass resolution is needed. The calibration sample may contain precursor chemicals to provide one or more ions of known mass-to-charge (m/z) ratio so that the mass spectrometer mass-scale may be corrected regularly. Because of small physical changes inside the mass spectrometer the mass-scale may be highly accurate for limited periods of time, are therefore the mass-scale requires small refinements on a regular bases during the time when other types of ions of interest are being analyzed. When it is desired that ions of a LockMass™ compound be provided for purposes of calibration, then the single-hole selector electrode 2144 is aligned with the second ion inlet orifice 2150 to support introduction of LockMass™ from the second electrospray needle 2142. Since the LockMass™ compound can be provided at relatively high abundance, it is advantageous to be able to transmit the LockMass™ ions along a flow path through the analyzer region 2154 that is short compared to a flow path for separating ions. In this way, the LockMass™ ions are introduced and pass through the FAIMS analyzer region 2154 to a not illustrated mass spectrometer very rapidly. A delay time associated with the ions passing through a longer portion of the analyzer region 2154 is avoided.

In the systems shown at FIGS. 20*a*-21*b*, the flows of gas have been omitted for the sake of clarity. It is advantageous to provide a curtain gas between the single-hole selector electrode and the outer electrode of FAIMS. Optionally, a flow of a carrier gas is provided within the analyzer region between the inner and outer FAIMS electrodes, to carry the ions along a direction toward the ion outlet. Although electrospray sources have been shown in the figures, many other ion sources can be used in this system including, but not restricted to atmospheric pressure chemical ionization, corona discharge, radioactivity (Ni foil), laser or high energy photons (MALDI, photoionization). In use, electrical connections are made to each electrospray needle (or other ion source components), the rotating selector electrode, to the curtain plate and outer FAIMS electrode to form a voltage gradient to drive the ions from the electrospray needle into the FAIMS analyzer region. In the case of ESI, a strong electric field around the tip of the electrospray needle is required to produce a fine spray of liquid droplets, and the formation of ions. Typical voltages applied for production of positive ions would be: needles at about 3000 volts, the selector electrode at 1000 volts, the curtain plate slightly lower than 1000 and the outer electrode at close to zero volts respectively.

Figure 22A:
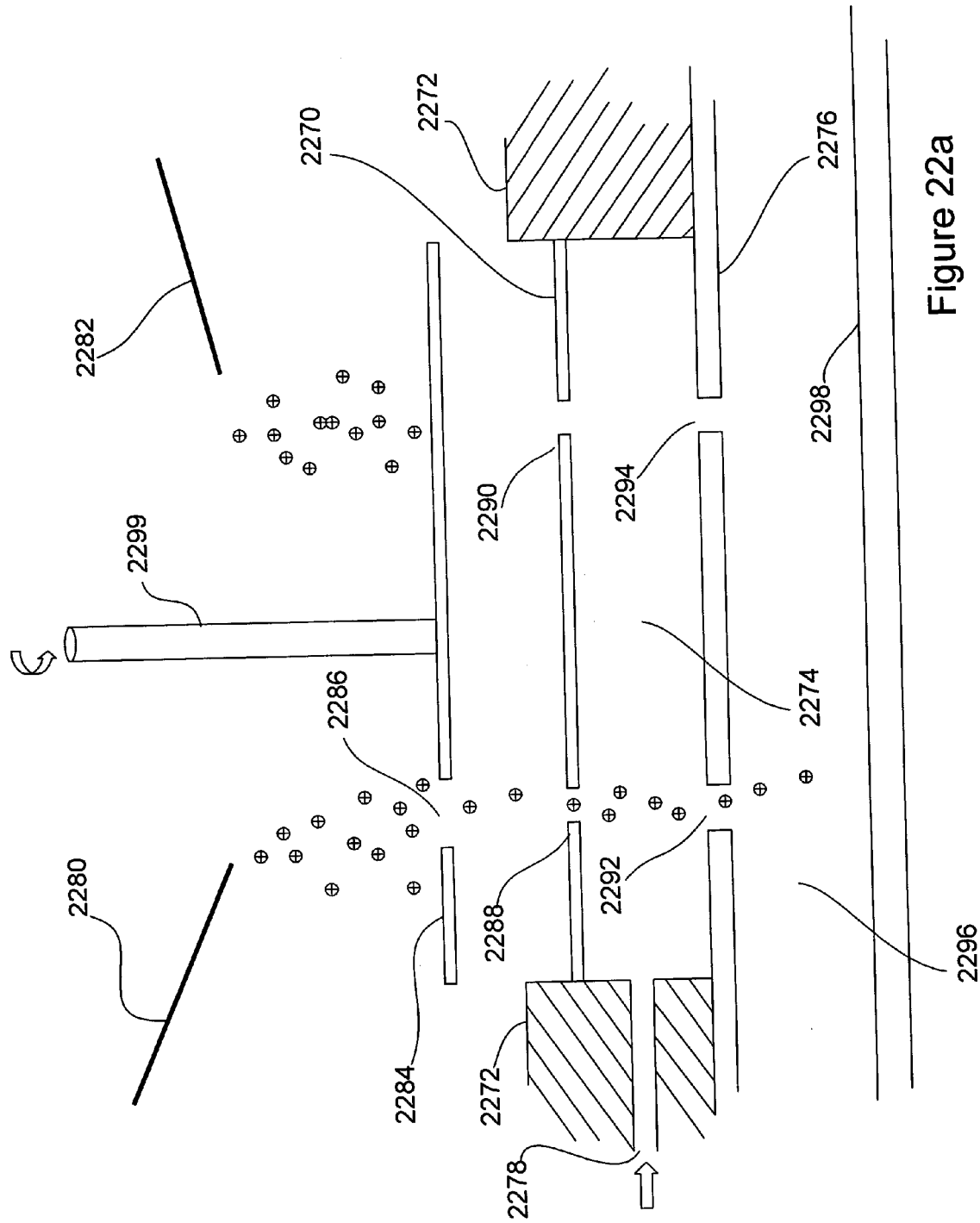
FIG. 22a shows an embodiment of the instant invention including both a rotating selector electrode and a curtain plate, in a first mode of operation.
Figure 22B:
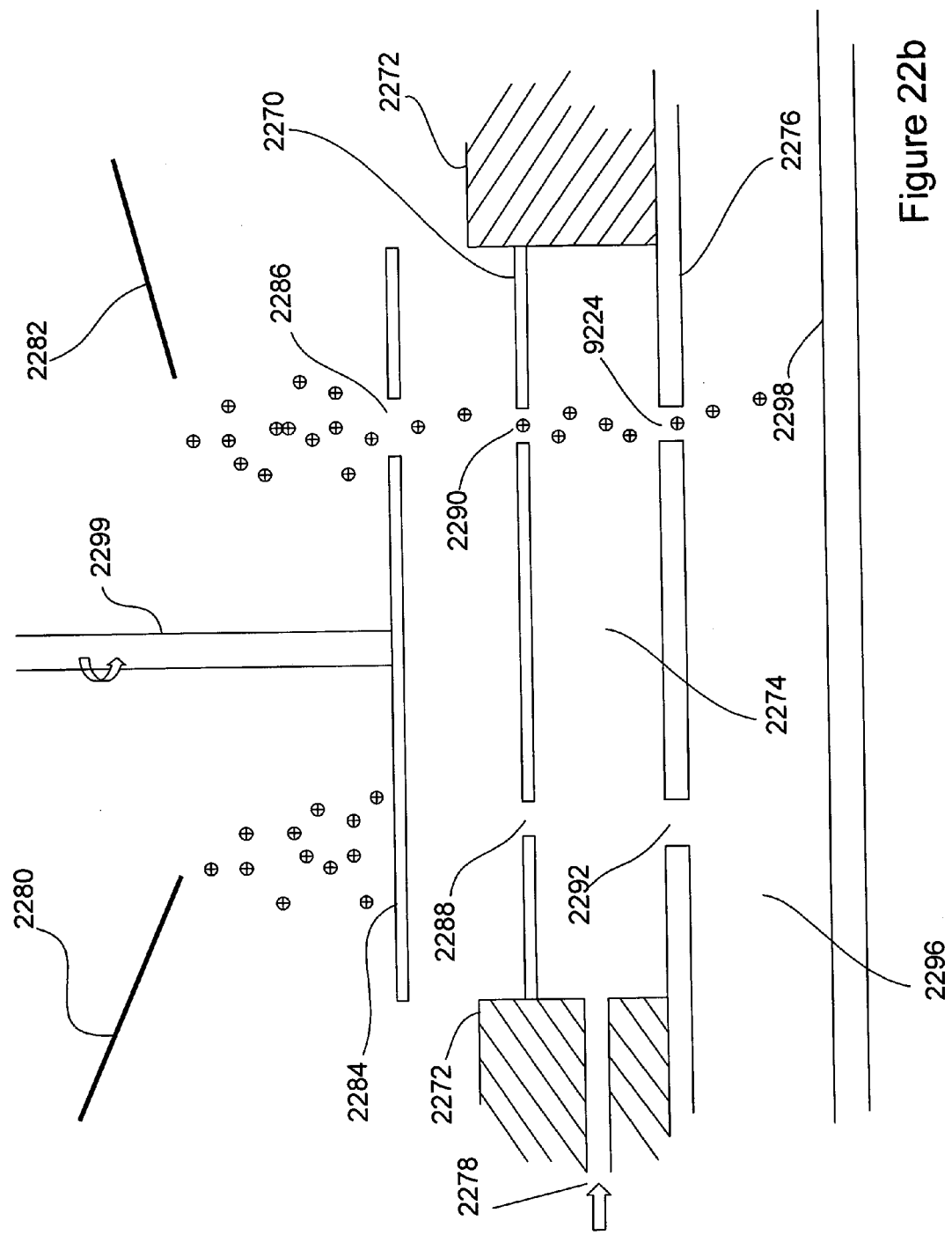
FIG. 22b shows an embodiment of the instant invention including both a rotating selector electrode and a curtain plate, in a second mode of operation.

Referring now to FIGS. 22*a* and 22*b*, shown is a system in which a single-hole selector electrode is disposed adjacent and parallel to a curtain plate of a FAIMS analyzer. The curtain plate 2270 is mounted into gas tight connection with an insulator 2272 that forms a chamber 2274 between the curtain plate 2270 and an upper electrode 2276 of FAIMS. A flow of curtain gas 2278 is delivered to the chamber 2274. FIGS. 22*a* and 22*b* show ions being selected from one of a first electrospray needle 2280 and a second electrospray needle 2282, respectively, by rotation of a single-hole selector electrode 2284 so that a single hole 2286 in the single-hole selector electrode 2284 is adjacent to one of the first electrospray needle 2280 and second electrospray needle 2282, respectively. For instance, a not illustrated motor or other mechanical device actuates a drive shaft 2299 to rotate the single-hole selector electrode 2284 to adopt one of two possible rotational orientations. By positioning the single-hole selector electrode 2284, the user has the option of permitting ions from either, but not both, the first electrospray needle 2280 and second electrospray needle 2282 to enter the FAIMS system.

In the present embodiment, the single-hole selector electrode 2284 is parallel and adjacent to the curtain plate 2270, which has two orifices 2288 and 2290 defined therethrough. The upper electrode 2276 of FAIMS also has two openings 2292 and 2294 defined therethrough and that are aligned with the orifices 2288 and 2290 in the curtain plate 2270. When the three openings are aligned, for example when the single hole 2286 in the single-hole selector electrode 2284 is aligned with openings in the curtain plate 2270 and the upper electrode 2276 of FAIMS, the ions from the selected ionization source passes through the three co-aligned openings and into an analyzer region 2296 of FAIMS between the upper electrode 2276 and a lower electrode 2298. The ions from the other non-selected source impinge on the surface of the single-hole selector electrode 2284, and are discharged. It is advantageous that the ions from the non-selected source do not enter the FAIMS via the aligned openings adjacent to the selected source. Optionally, a blocking plate (not shown) is installed to prevent cross-talk between sources and openings. Advantageously the single-hole selector electrode 2284 and the curtain plate 2270 are in close proximity. The two may optionally be in sliding contact with each other. The single-hole selector electrode 2284 and the curtain plate 2270 are conductive electrodes connected to power supplies that are used to maintain the voltage applied to these electrodes. Similarly the upper electrode 2276 of FAIMS is held at a bias voltage through contacts with a power supply.

Still referring to FIGS. 22*a* and 22*b*, a not illustrated portion of the curtain gas 2278 flows outward through the curtain plate towards the ion source helping to desolvate the ions as they approach the curtain plate. A second (optional) portion of the gas 2278 flows into FAIMS to contribute to (or constitute) the carrier gas that transports the ions through the analyzer region 2296 of FAIMS. The flow of gases that are chosen is dependent on the type ion ionization source that is employed with the present invention. The gases discussed here are specific for the operation of an atmospheric pressure electrospray ionization system. Additionally, in some cases the source of ions may be operated at elevated or reduced temperatures, requiring isolation of FAIMS in order to operate FAIMS at optimum temperature for ion separation and ion transmission.

Referring now to FIG. 23, shown is the system of FIGS. 22*a* and 22*b* in which gas flows are illustrated but ions have been omitted for clarity. Elements labeled with the same numerals have the same function as those illustrated in FIGS. 22*a* and 22*b*. Since there are two openings 2292 and 2294 through the outer electrode 2276 of FAIMS, a portion of the curtain gas optionally flows into each of these openings. The flow from the curtain region 2274 into FAIMS through these two openings 2292 and 2294 optionally is reduced to approximately zero by providing a carrier gas to the analyzer region 2296 independently. However, it is often found that the transmission of ions into the FAIMS analyzer is more efficient if a flow of gas aids transport of the ions from the chamber 2274 between the curtain plate 2270 and outer electrode 2276 and into FAIMS. The curtain gas preferably flows outward through both openings 2288 and 2290 in the curtain plate 2270, as shown in FIG. 23. Optionally, the single-hole selector electrode 2284 is in close proximity or in sliding contact (and at the same electrical potential) with the curtain plate 2270, thus always covering one (or both) of the holes in the curtain plate 2270. It is advantageous in this case to switch rapidly between the two positions, to minimize the disturbance in the gas flows when the two holes in the curtain plate are simultaneously closed.

FIG. 24 illustrates the special case of LockSpray™ used with Waters high resolution TOF mass spectrometers. The first electrospray needle 2480 is used to produce ions of the samples that are being analyzed, while the second electrospray needle 2482 is used for producing ions of the calibration compound. In this LockSpray™ example, the ions from the second electrospray needle 2482 are used for calibrating the mass-scale of the high resolution TOF mass spectrometer, and are passed only occasionally along a calibration channel through FAIMS for short periods of time to permit re-calibration of the mass spectrometer. It is therefore preferred that the opening 2500 in the curtain plate 2270 and the opening 2502 in the outer electrode 2476 of FAIMS are smaller for the calibration channel than the openings used for the analytical channel. Optionally, the number of ions of the calibration compound arriving at the detector is increased by increasing the concentration of the calibration compound delivered to second electrospray needle 2482, thus minimizing the need for high sensitivity through use of large apertures through the curtain plate and outer electrode of FAIMS along the calibration channel.

Figure 25:
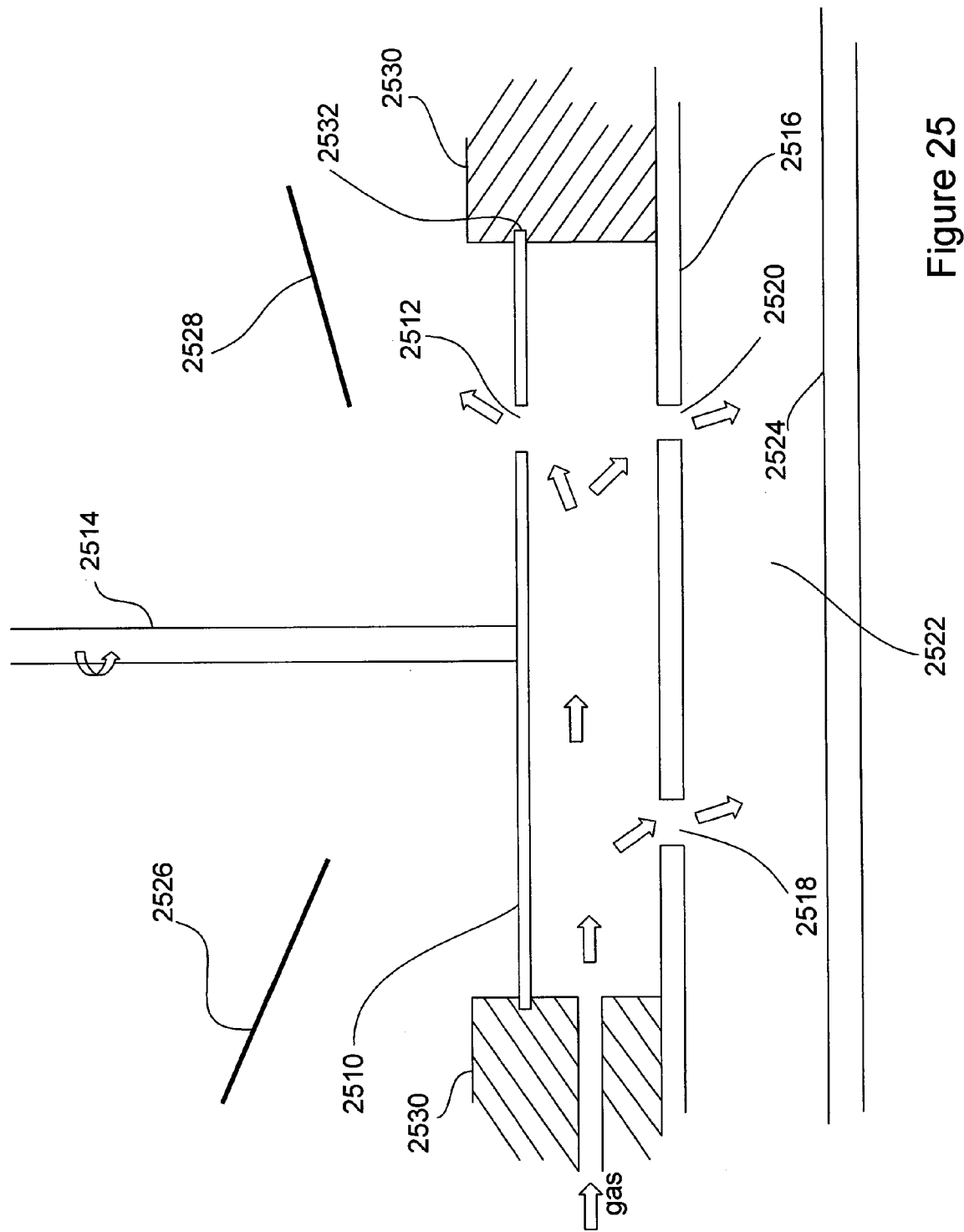
FIG. 25 shows a cross sectional view of an ion introduction region of a system according to another embodiment of the instant invention.

FIG. 25 illustrates in cross section an ion introduction region of a system according to an embodiment of the instant invention. In FIG. 27 a single-hole selector electrode 2510 replaces the curtain plate 2270. The single-hole selector electrode 2510 includes a single opening 2512 defined therethrough and is mounted to a drive shaft 2514. In FIG. 25, an upper electrode 2516 of FAIMS has a first ion inlet orifice 2518 and a second ion inlet orifice 2520 defined therethrough. An analyzer region 2522 is defined by a space between the upper electrode 2516 and a lower electrode 2524 of the FAIMS.

In the system that is shown at FIG. 25, both a first electrospray needle 2526 and a second electrospray needle 2528 are in continuous operation. The opening 2512 in the single-hole selector electrode 2510 is controllably alignable with the first ion inlet orifice 2518 or the second ion inlet orifice 2520 by rotation of the single-hole selector electrode 2510 about a rotation axis aligned with the drive shaft 2514. For instance, a not illustrated motor or other mechanical device actuates the drive shaft 2514 to rotate the single-hole selector electrode 2510 to adopt one of two possible rotational orientations. In each orientation the single opening 2512 is positioned adjacent to one of the ion inlet orifices 2518 and 2520 into FAIMS. By positioning the single-hole selector electrode 2510, the user has the option of introducing ions from either, but not both, ion sources 2526 and 2528 into the FAIMS system at a time.

Certain advantages result from substituting the curtain plate 2270 with the single-hole selector electrode 2510. For instance, the arrangement that is shown at FIG. 25 minimizes the total number of electrodes that are required. On the other hand, this approach requires that the single-hole selector electrode 2510 remain in gas-tight contact with an electrically insulating material 2530, as it smoothly rotates while driven by a drive shaft 2514 and is used to select the source of ions to be delivered to FAIMS. To this end, the single-hole selector electrode 2510 is retained about its periphery within a circumferential groove 2532 that is defined within the electrically insulating material 2530. The electrically insulating material 2530 is disposed adjacent to the upper electrode 2516 and forms a substantially gas-tight seal with the upper electrode 2516, so as to define a curtain gas region proximate the first ion inlet orifice 2518 and the second ion inlet orifice 2520. In previous embodiments discussed above, the curtain plate 2270 is a part of the gas-tight region into which curtain gas is delivered, and it is easier to maintain a gas-tight seal with a stationary, non-moving curtain plate 2270.

It is a further advantage of the system shown at FIG. 25 that during rotation of the single-hole selector electrode 2510, the gas flows are not disturbed. The three gas flows shown in FIG. 25, being two gas flows into the analyzer region of FAIMS via ion inlet orifices 2518 and 2520, and a flow through the single opening 2512 of the selector electrode 2510 towards the ionization sources, do not change during the rotation of the selector electrode 2510. During the rotation, however, there is a period of time during which no ions enter the FAIMS analyzer. This delay is additive with a delay for ion transmission through the FAIMS to a not illustrated ion outlet.

Figure 26A:
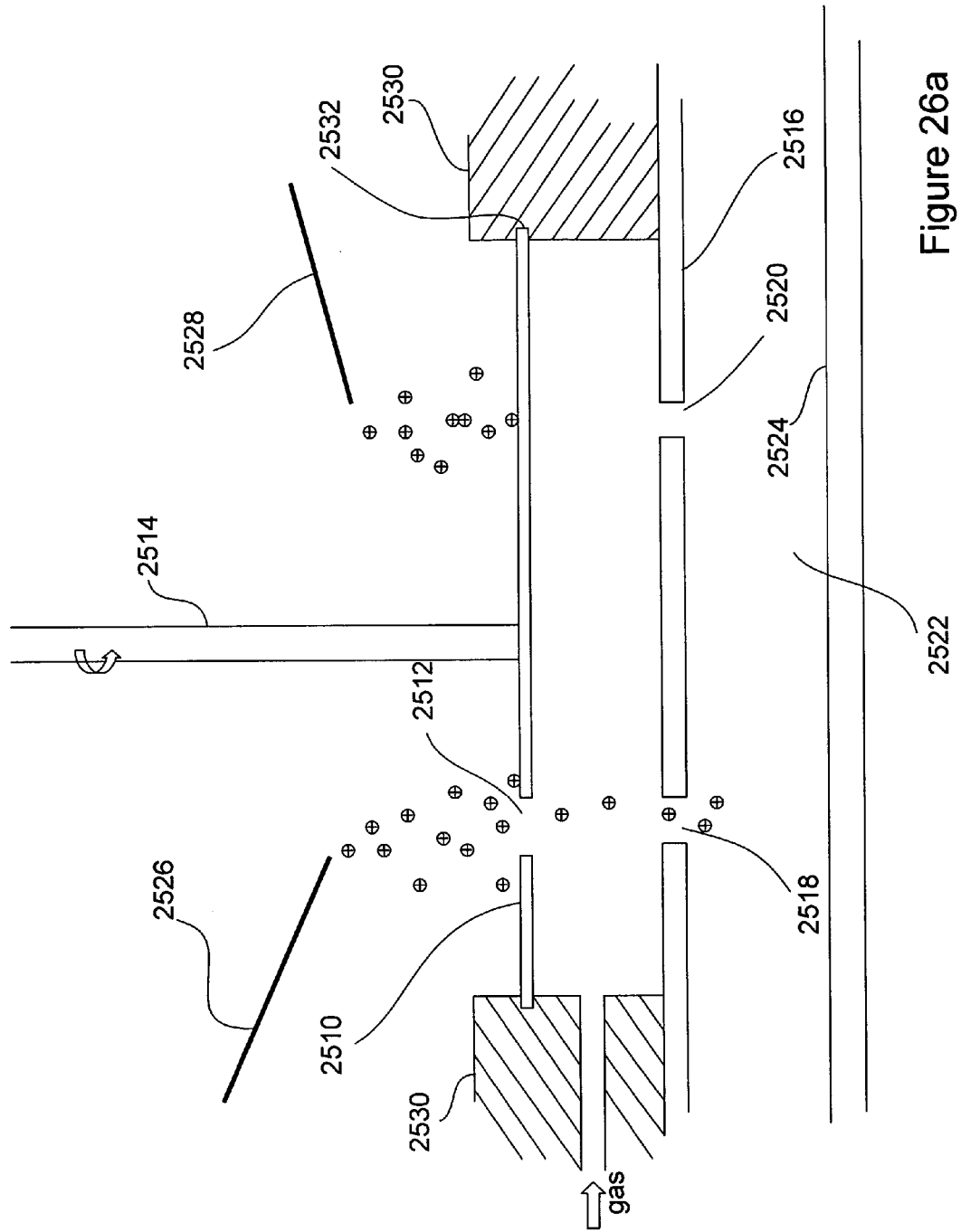
FIG. 26a shows the system of FIG. 25 in a first mode of operation.
Figure 26B:
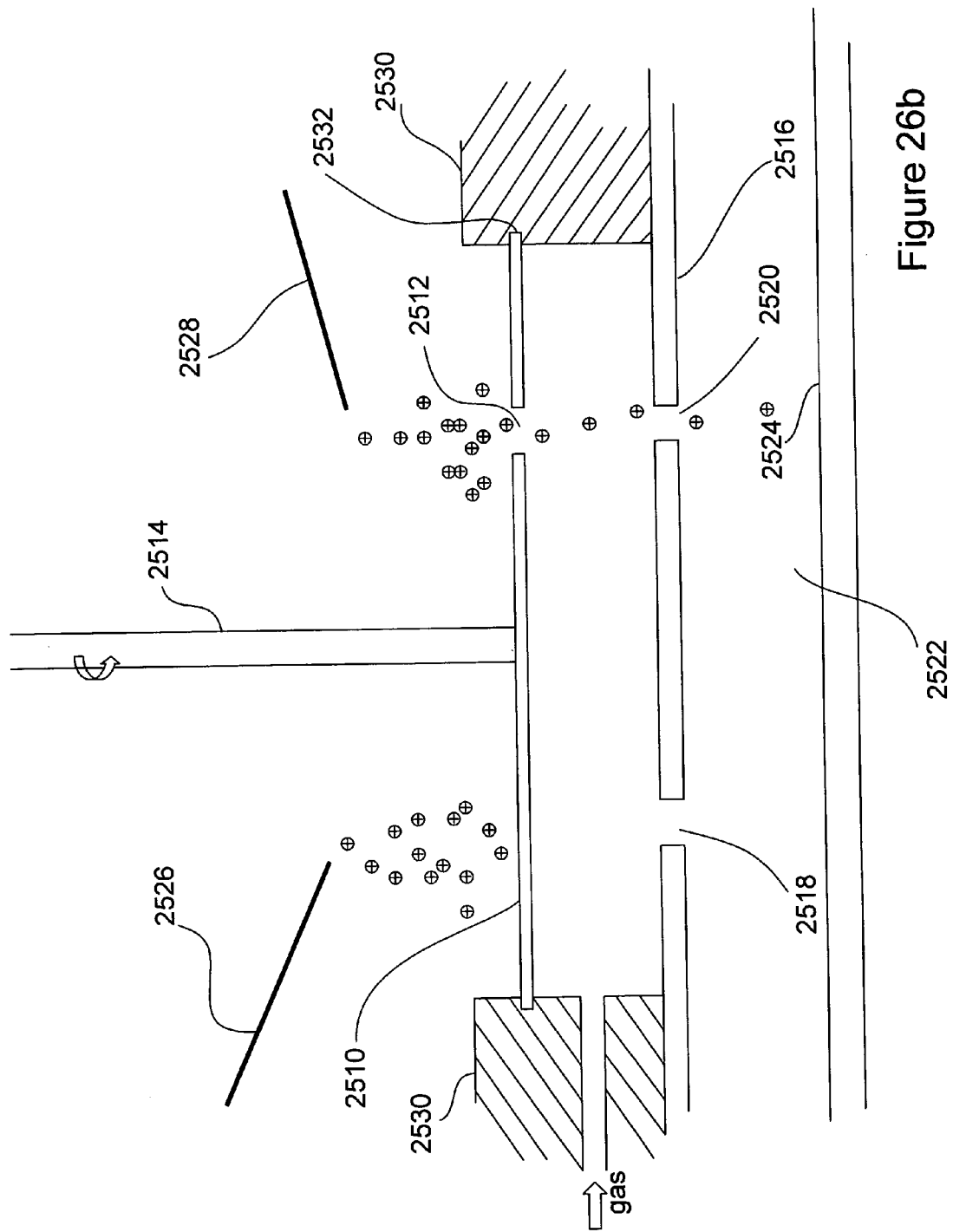
FIG. 26b shows the system of FIG. 25 in a second mode of operation.

FIGS. 26a and 26b illustrate the flow of ions through the system of FIG. 25 when the single-hole selector electrode 2510 is aligned with the first ion inlet orifice 2518 and the second ion inlet orifice 2520, respectively. Elements labeled with the same numerals have the same function as those illustrated in FIG. 25. The periods of time at each of the two possible points of rotation, and the timing of the selection of each ion source is controlled from a master computer system (not shown).

Figure 27A:
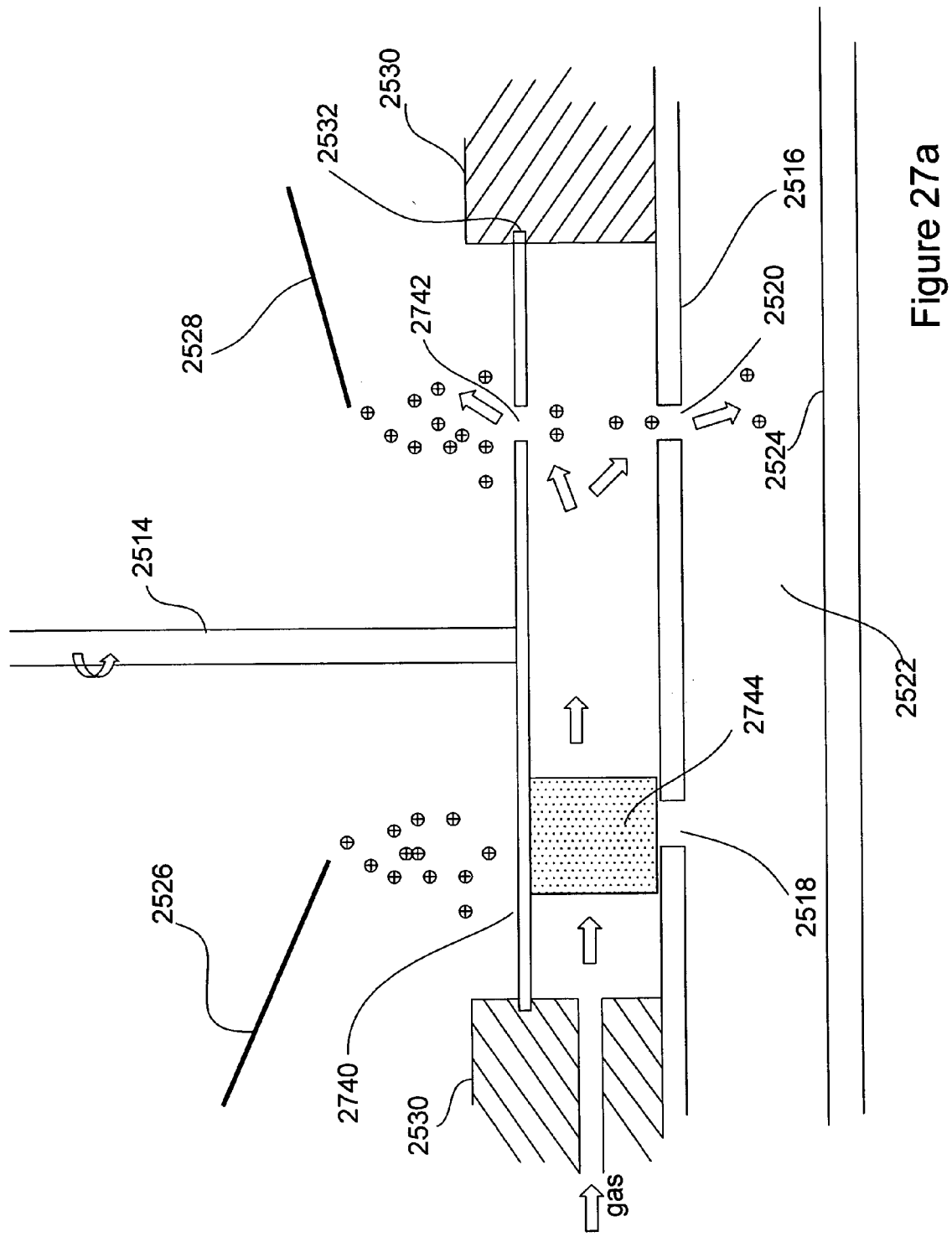
FIG. 27a shows a cross sectional view of an ion introduction region of a system according to another embodiment of the instant invention, in a first mode of operation.
Figure 27B:
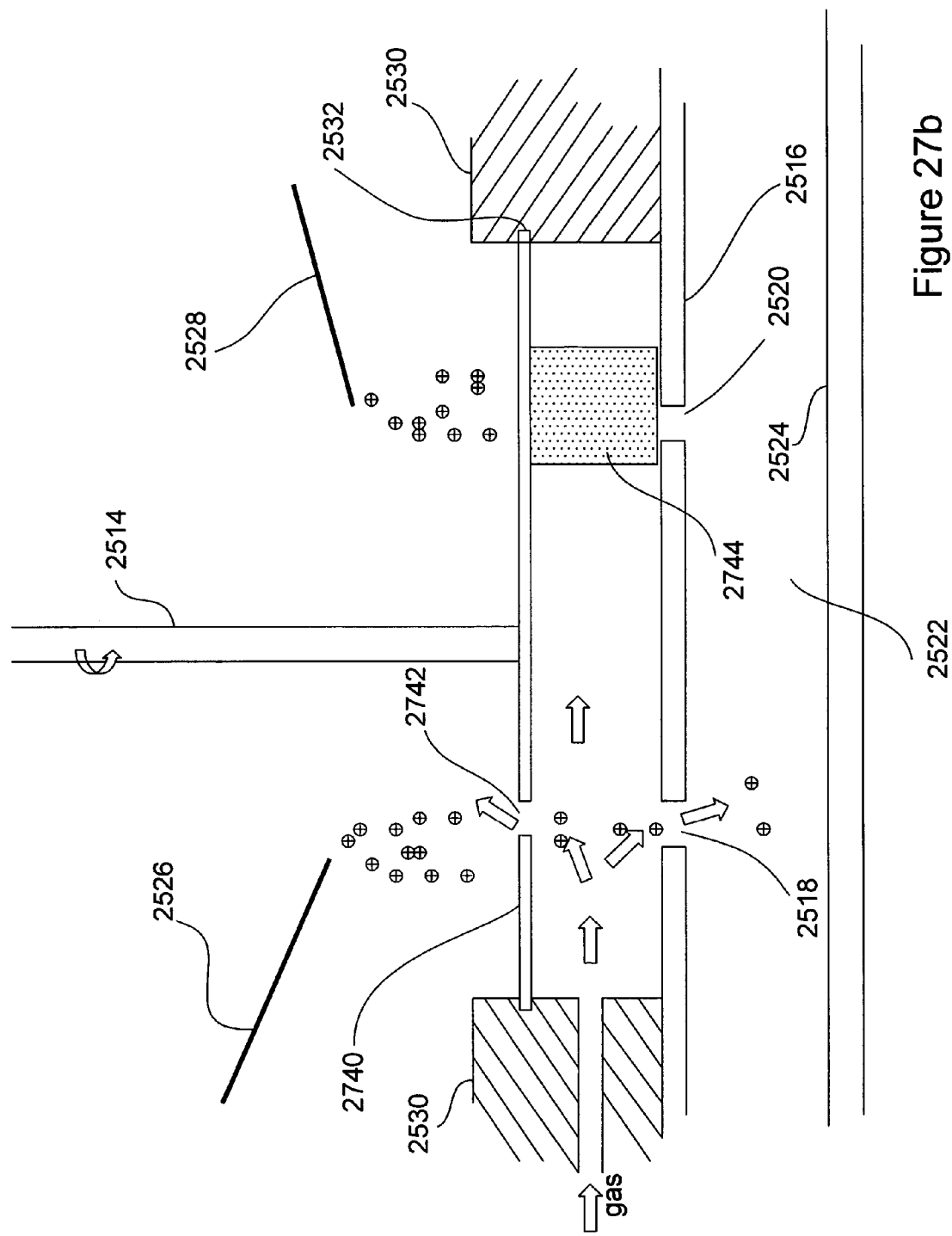
FIG. 27b shows the system of FIG. 27a in a second mode of operation.

FIGS. 27a and 27b show an ion introduction region similar to that discussed with reference to FIGS. 25 through 26b, but including a modified single-hole selector electrode. Elements labeled with the same numerals have the same function as those illustrated in FIGS. 25, 26a and 26b. In the present embodiment, a single-hole selector electrode 2740 has an extension 2744 from the surface facing the upper electrode 2516 of FAIMS, which extension 2744 serves to reduce or eliminate the flow of gas into the non-active orifice (e.g. the first ion inlet orifice 2518 in FIG. 27a and the second ion inlet orifice 2520 in FIG. 27b) in the upper electrode 2516 of FAIMS. Of course, when the non-active orifice is covered by the extension 2744, an active orifice (e.g. the second ion inlet orifice 2520 in FIG. 27a and the first ion inlet orifice 2518 in FIG. 27b) is aligned with an opening 2742 in the single-hole selector electrode 2740. Accordingly, in FIG. 27a ions from the second electrospray needle 2528 are selectively passed into the FAIMS analyzer region 2522 after passing through the opening 2742 and the second ion inlet orifice 2520. Similarly, in FIG. 27b ions from the first electrospray needle 2526 are selectively passed into the FAIMS analyzer region 2522 after passing through the opening 2742 and the first ion inlet orifice 2518.

The extension 2744 is optionally a small disc of insulating material, such as for instance PEEK or Teflon™, that makes contact with the upper electrode 2516 of FAIMS, so as to make gas-tight contact with the upper electrode 2516 while covering one of the ion inlet orifices 2518 and 2520. The extension 2744 is optionally a short cylinder only slightly wider in diameter than a larger one of the ion inlet orifices 2518 and 2520 (e.g. if one of the orifices 2518 and 2520 is dimensioned smaller than the other for LockMass™ applications), and therefore does not interfere substantially with the gas flow elsewhere in the region between the single-hole selector electrode 2740 and the upper electrode 2516 of FAIMS. If the extension 2744 is a conductive material, electrical contact with the upper electrode 2516 must be avoided. Optionally a small disc of insulator is mounted to the lower surface of the extension 2744 to avoid electrical contact when the extension 2744 is fabricated from a conductive material, and to provide complete closure of the opening in the upper electrode 2516 of FAIMS. Since during use the pressure differences are small between the analyzer region and the curtain gas region, absolute gas-tight closure is not essential for significantly reducing the flow of gas through the non-active orifice in the upper electrode of FAIMS 2516.

In the systems shown at FIGS. 22a to 27b, first ion inlet orifice is defined within a first portion of the upper FAIMS electrode such that ions introduced via the first ion inlet orifice travel a first distance between the first ion inlet orifice and an ion outlet orifice. In particular, the first distance is selected to provide an average ion flow path through the analyzer region of FAIMS that is sufficiently long to support at least partial separation of a first type of ion contained in a mixture of ions introduced via the first ion inlet orifice, from a second type of ion contained in the same mixture. In other words, ions introduced into the analyzer region of FAIMS via the first ion inlet orifice are separated according to the FAIMS principle. Optionally, the second ion inlet orifice is defined within a second portion of the upper electrode of FAIMS such that ions introduced via the second ion inlet orifice travel a second distance between the second ion inlet orifice and the ion outlet orifice, the second distance being shorter than the first distance. In particular, the second distance is selected to provide an average ion flow path through the analyzer region of FAIMS that is sufficiently short to support transmission of all types of ions contained in a mixture of ions introduced via the second ion inlet orifice. In this case, the FAIMS separation mechanism is effectively "turned off" for those ions introduced into the analyzer region via the second ion inlet orifice. Accordingly, this optional arrangement supports both a "total ion" mode of operation and use of a LockMass™ or other calibration compound, as described above with reference to FIGS. 21a and 21b.

Alternatively, the second ion inlet orifice is defined within a second portion of the upper electrode of FAIMS such that ions introduced via the second ion inlet orifice travel a second distance between the second ion inlet orifice and the ion outlet orifice. In this case, the second distance is shorter than the first distance but is sufficiently long to support at least partial separation of a first type of ion contained in a mixture of ions introduced via the second ion inlet orifice, from a second type of ion contained in the same mixture. Advantageously, this latter arrangement supports rapid sequencing between different ionization sources and/or different samples. For instance, optionally the ion type of interest produced by the first electrospray needle and the ion type of interest produced by the second electrospray are different types of ions. Further optionally, one of the first electrospray needle and the second electrospray needle is substituted by a different type of ionization source. Still further optionally, the sample is provided to each of the first electrospray needle and the second electrospray needle after separation using a chromatographic or electrophoretic technique. For instance, the first electrospray needle is in communication with an outlet of a HPLC system and the second electrospray needle is in communication with the outlet of a GC system. Advantageously, sample eluted from one of the HPLC system and the GC system may be analyzed using the FAIMS system during a time of no sample elution from the other one of the HPLC system and the GC system. Since analysis by chromatographic or electrophoretic techniques is characterized by long periods of separation followed by a relatively short elution period, multiplexing several chromatographic or electrophoretic systems into a single FAIMS with rapid switching between sources is efficient.

Furthermore, although the FAIMS of FIGS. 22a-27b was described in terms of an upper electrode and a lower electrode, such as for instance is found in a parallel plate geometry FAIMS, the description of the instant invention is equally applicable to other geometries of FAIMS, including but not limited to concentric cylinder geometry electrodes with or without a domed inner electrode; parallel plate geometry electrodes with either curved or flat electrode plates; concentric cylinder geometry electrodes operating in a side-to-side mode; spherical electrodes; quadrupolar electrodes; etc. In those geometries of the FAIMS device that are based upon overlapping concentric cylindrical electrodes, the upper electrode is equivalent to an outer cylindrical electrode and the lower electrode is equivalent to an inner cylindrical electrode.

All of the previous figures illustrate embodiments of the present invention wherein the ion sources are in close proximity to each other. This is advantageous since the mechanical means for opening and closing the openings for ion transmission into FAIMS can be relatively simple. This is also advantageous since the hardware holding the electrospray needles can be compact, and the ion sources may be enclosed within a common housing chamber (not shown here).

Figure 28B:
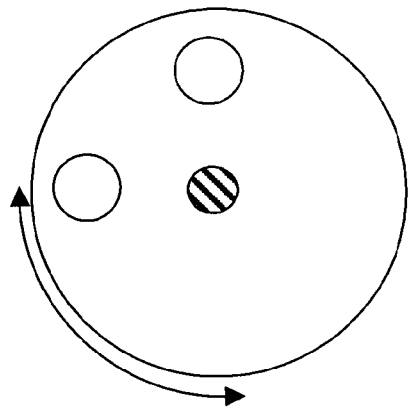
FIG. 28b shows a top view of a multiple-hole selector electrode.
Figure 28D:
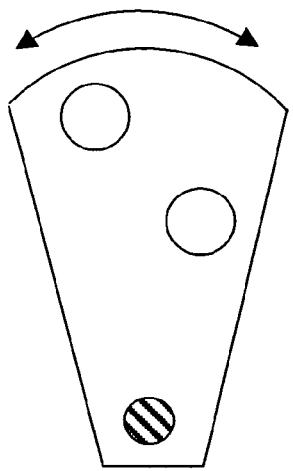
FIG. 28d shows a top view of an eccentrically mounted multiple-hole selector electrode.
Figure 28A:
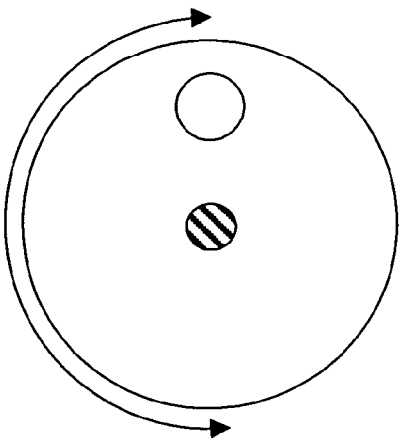
FIG. 28a shows a top view of a single-hole selector electrode.
Figure 28C:
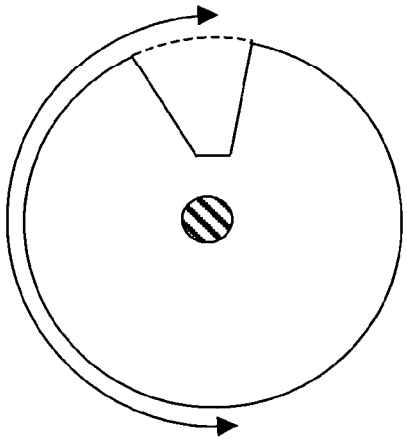
FIG. 28c shows a top view of a notched selector electrode.

Referring now to FIGS. 28a to 28d, shown are several examples of optional selector electrode configurations suitable for use with the various embodiments of the instant invention. FIG. 28a shows a top view of a single-hole selector electrode similar to the one described with reference to FIGS. 19 through 26b. FIG. 28b shows a double-hole selector electrode, in which rotation by 90° about a centrally mounted drive shaft is sufficient for switching between two ion inlet orifices into FAIMS. FIG. 28c shows a notched selector electrode, in which a portion of the selector electrode is cut away or the electrode is formed absent at least a portion of a sector. The shape of the notch in FIG. 28c is for illustrative purposes only, and other suitable shapes may be envisaged. Finally, FIG. 28d shows an alternative arrangement in which a drive shaft is eccentrically mounted to the ion selector electrode. Only a relatively small amount of rotation, relative to other embodiments, about the drive shaft is required to switch between two ion inlet orifices into FAIMS. Preferably, a not-illustrated barrier is provided between the openings in the selector electrode so as to prevent possible cross-talk between the sources and the openings.

Figure 29:
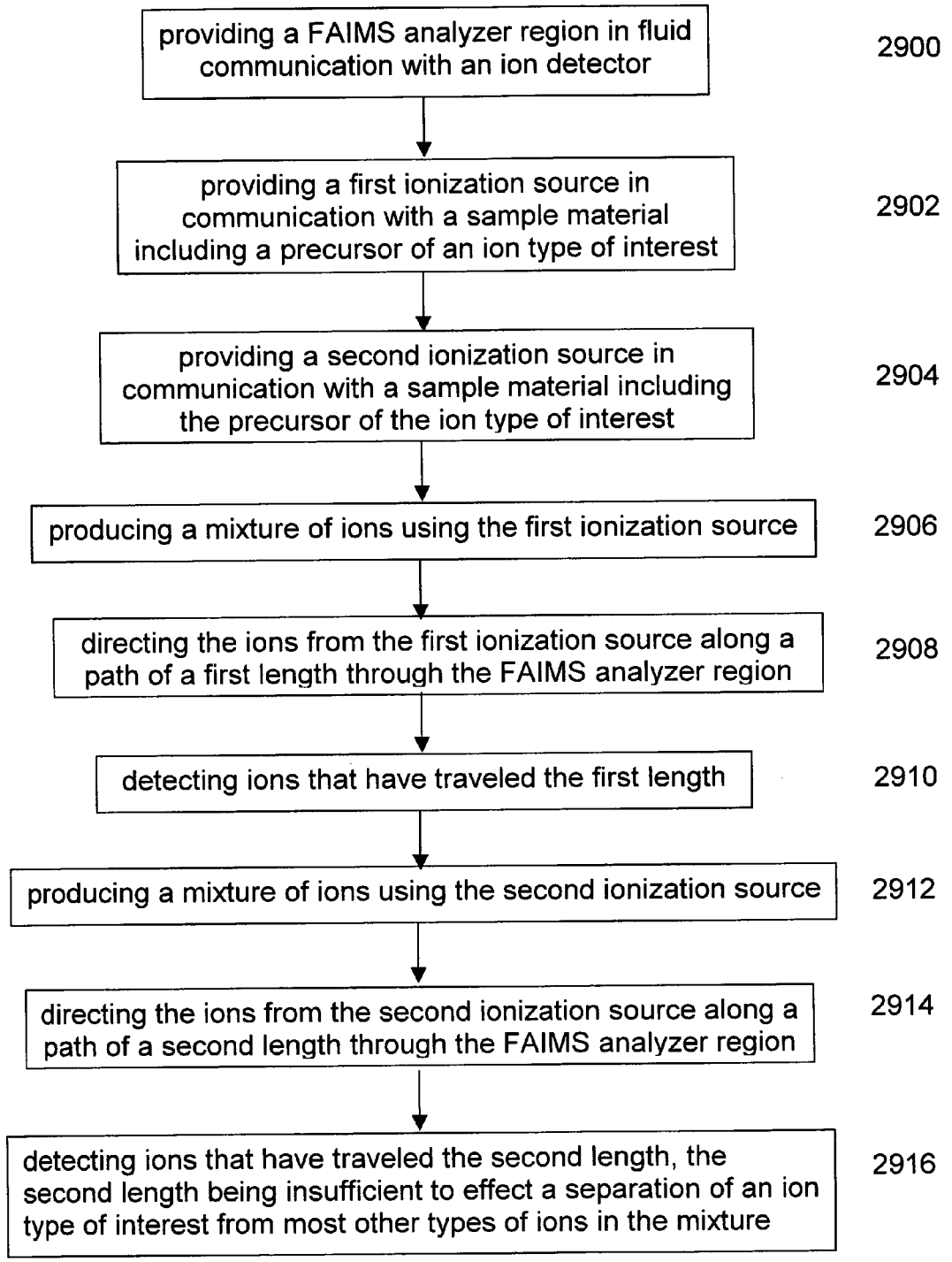
FIG. 29 is a simplified flow diagram of a method of separating ions according to an embodiment of the instant invention.

Referring now to FIG. 29, shown is a simplified flow diagram of a method for separating ions according to an embodiment of the instant invention. At step 2900, a FAIMS analyzer region is provided in fluid communication with an ion detector. At step 2902, a first ionization source is provided in communication with a sample material including a precursor of an ion type of interest. At step 2904, a second ionization source is provided in communication with a sample material including the precursor of the ion type of interest. Using the first ionization source, a mixture of ions is produced at step 2906, the mixture of ions comprising different types of ions including the ion type of interest. During a first period of time, the ions are directed at step 2908 from the first ionization source along a path of a first length through the FAIMS analyzer region, the first length being sufficient to effect at least a partial separation of the ion type of interest from other types of ions that may be in the mixture. Using the ion detector, ions are detected at step 2910 after the ions have traveled the first length. Using the second ionization source, a mixture of ions is produced at step 2912 comprising different types of ions including the ion type of interest. During a second period of time not overlapping with the first period of time, the ions are directed at step 2914 from the second ionization source along a path of a second length through the FAIMS analyzer region, the second length being insufficient to effect a separation of the ion type of interest from most other types of ions in the mixture. At step 2916 and using the ion detector, the ions are detected after the ions have traveled the second length.

Figure 30:
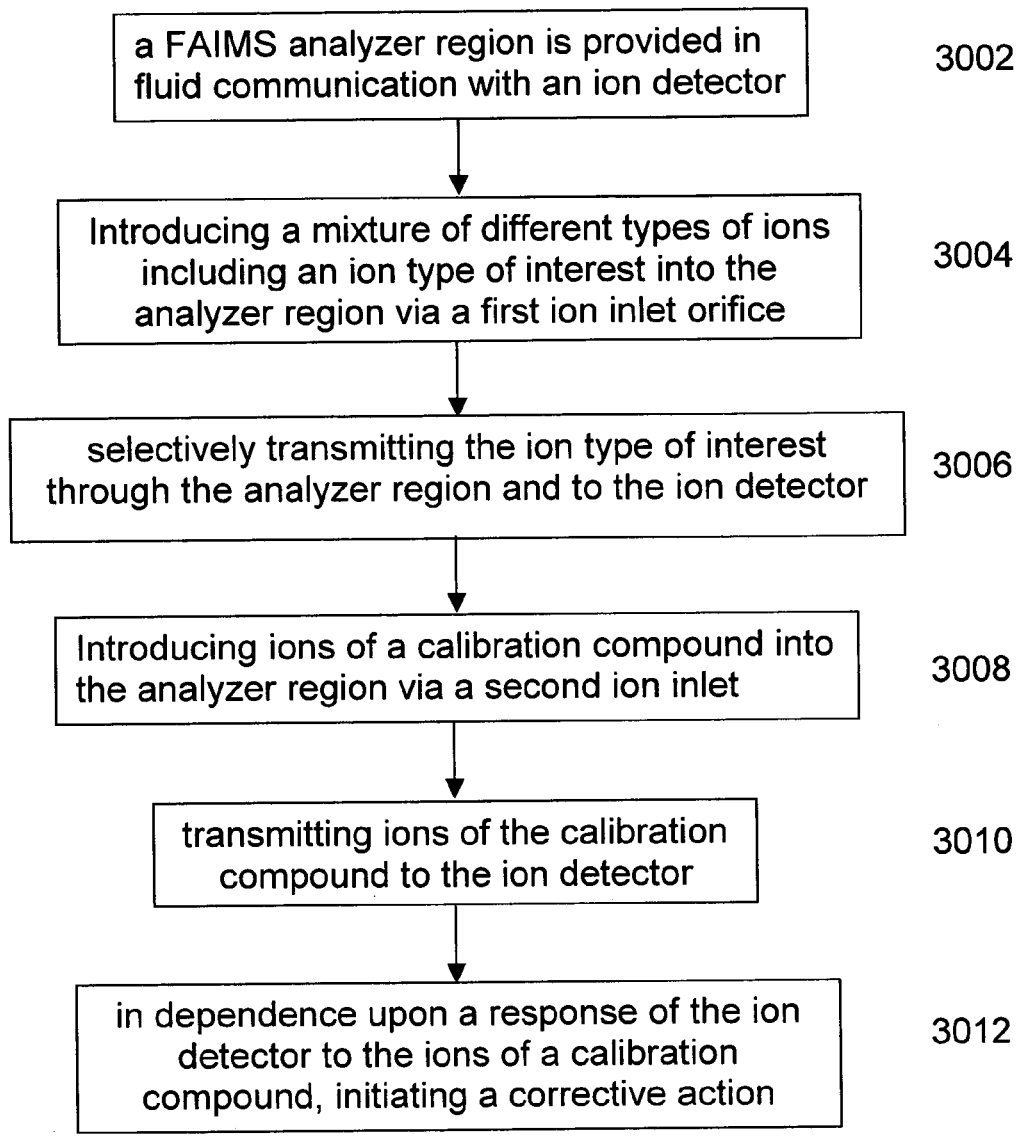
FIG. 30 is a simplified flow diagram of another method of separating ions according to an embodiment of the instant invention.

Referring now to FIG. 30, shown is a simplified flow diagram of another method for separating ions according to an embodiment of the instant invention. At step 3002 a FAIMS analyzer region is provided in fluid communication with an ion detector. At step 3004 a mixture of different types of ions including an ion type of interest is introduced into the analyzer region via a first ion inlet orifice. At step 3006 the ion type of interest is selectively transmited through the analyzer region and to the ion detector. At step 3008 ions of a calibration compound are introduced into the analyzer region via a second ion inlet orifice. At step 3010 the ions of a calibration compound are transmitted to the ion detector. In dependence upon a response of the ion detector to the ions of a calibration compound, the ion detector initiates corrective action, if needed, at step 3012. Upon completion of this corrective action, the mixture of different types of ions including an ion type of interest is introduced into the analyzer region via a first ion inlet orifice, and this ion of interest is selectively transmitted through the analyzer region and to the ion detector. The measurements of the ion of interest taken after the corrective action are improved relative to those that would have been taken absent the corrective action.

Figure 31A:
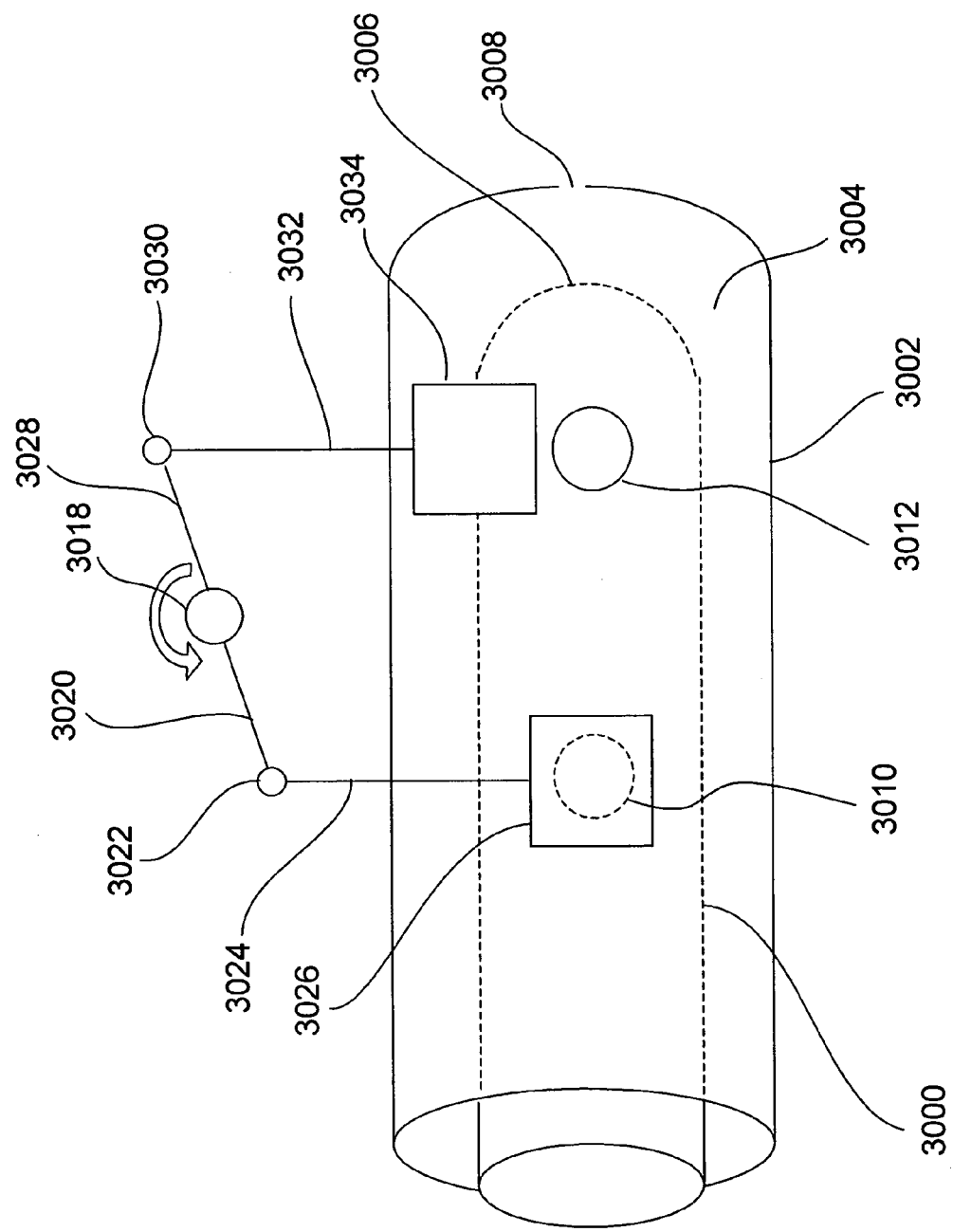
FIG. 31a shows a system according to an embodiment of the instant invention for selecting ions from two ion sources located adjacent to a FAIMS analyzer, while in a first mode of operation.

Referring now to FIG. 31*a*, shown is a system according to an embodiment of the instant invention for selecting ions from two ion sources located adjacent to a FAIMS analyzer, while in a first mode of operation. In FIG. 31*a*, an inner electrode 3000 is provided in an overlapping concentric arrangement with an outer electrode 3002, defining an analyzer region 3004 therebetween. The inner electrode 3000 includes a dome-shaped terminus 3006 for directing ions out of the analyzer region 3004 via an ion outlet orifice 3008. In particular, the ion outlet orifice 3008 is defined in the outer electrode 3002 and lies along the center axis of rotation of the inner electrode 3000. In the FAIMS device that is shown at FIG. 31*a*, two ion inlet orifices 3010 and 3012 are provided within adjacent regions along the length of the outer electrode 3002. During use, a not illustrated power supply is used to provide an asymmetric waveform and a direct current compensation voltage potential between the inner electrode 3000 and the outer electrode 3002 so as to establish an electric field therebetween. Other operational parameters of the FAIMS device, such as for instance gas temperature, gas composition, gas pressure, and the presence of temperature gradients within the gas, also affects ion separation performance. Of course, the FAIMS electrodes 3000 and 3002 are mounted within suitable electrically insulating material (not illustrated) and housed within an appropriate housing (not illustrated) for supporting gas flow through the device. In addition, electrical connections to the electrodes have been omitted for clarity.

Still referring to FIG. 31*a*, two not illustrated ionization sources are provided one each adjacent to the ion inlet orifices 3010 and 3012. By way of non-limiting example, the ionization sources are provided in the form of electrospray ionization sources. Optionally another suitable type of ionization source is used. Further optionally, the two ionization sources include two different types of ionization sources.

FIG. 31*a* also shows an inlet selection system according to an embodiment of the instant invention. The inlet selection system includes an actuator interface 3018. The actuator interface 3018 is for being driven by a controller including a rotating actuator, such as for instance a motor of a type that is typically provided with a Waters/Micromass LockSpray™ calibration system as one non-limiting example. Of course, any other suitable rotating actuator optionally is used. In FIG. 31*a*, the actuator interface 3018 is coupled via a first arm 3020, a first rotating joint 3022 and a second arm 3024 to a first cover portion 3026, and is coupled via a third arm 3028, a second rotating joint 3030 and a fourth arm 3032 to a second cover portion 3034. In the instant example, the first cover portion 3026 is provided in the form of a first cover-plate electrode, and the second cover portion 3034 is provided in the form of a second cover-plate electrode. The actuator interface 3018 is for moving the first cover portion 3026 from a first position in which the ion inlet orifice 3010 is covered by the first cover portion 3026 to a second position in which the ion inlet orifice 3010 is uncovered by the first cover portion 3026. Simultaneously, the actuator interface 3018 is for moving the second cover portion 3034 from a first position in which the ion inlet orifice 3012 is uncovered by the second cover portion 3034 to a second position in which the ion inlet orifice 3012 is covered by the second cover portion 3034. Accordingly, FIG. 31*a* shows the inlet selection system in a first mode of operation, in which the first cover portion 3026 and the second cover portion 3034 are both in the first position. In the first mode of operation, ions that are produced at an ionization source adjacent to the ion inlet 3012 are directed through the ion inlet 3012 and into the analyzer region 3004, whilst ions that are produced at an ionization source adjacent to the ion inlet 3010 are directed toward the first cover portion 3026 where they are neutralized and the charge is carried away via the not illustrated electrical connections to the first cover portion 3026.

As is shown in FIG. 31*a*, the first cover portion 3026 is dimensioned to be larger than the ion inlet orifice 3010, and the second cover portion 3034 is dimensioned to be larger than the ion inlet orifice 3012. Accordingly, each cover portion overlaps with a region of the outer electrode 3002 about the respective ion inlet orifice, such that ions are substantially prevented from entering via a non-selected one of the ion inlet orifices. Preferably, the first through fourth arms 3020, 3024, 3028 and 3032 are stiff arms, such that rotation of the actuator interface 3018 translates into simultaneous motion, but in opposite direction, of the first and second cover portions 3026, 3034. Of course, any other suitable mechanical linkage system for coupling the actuator interface 3018 with the first cover portion 3026 and with the second cover portion 3034, so as to support the functionality described above, is optionally used in place of the arms and rotating joints described herein.

Figure 31B:
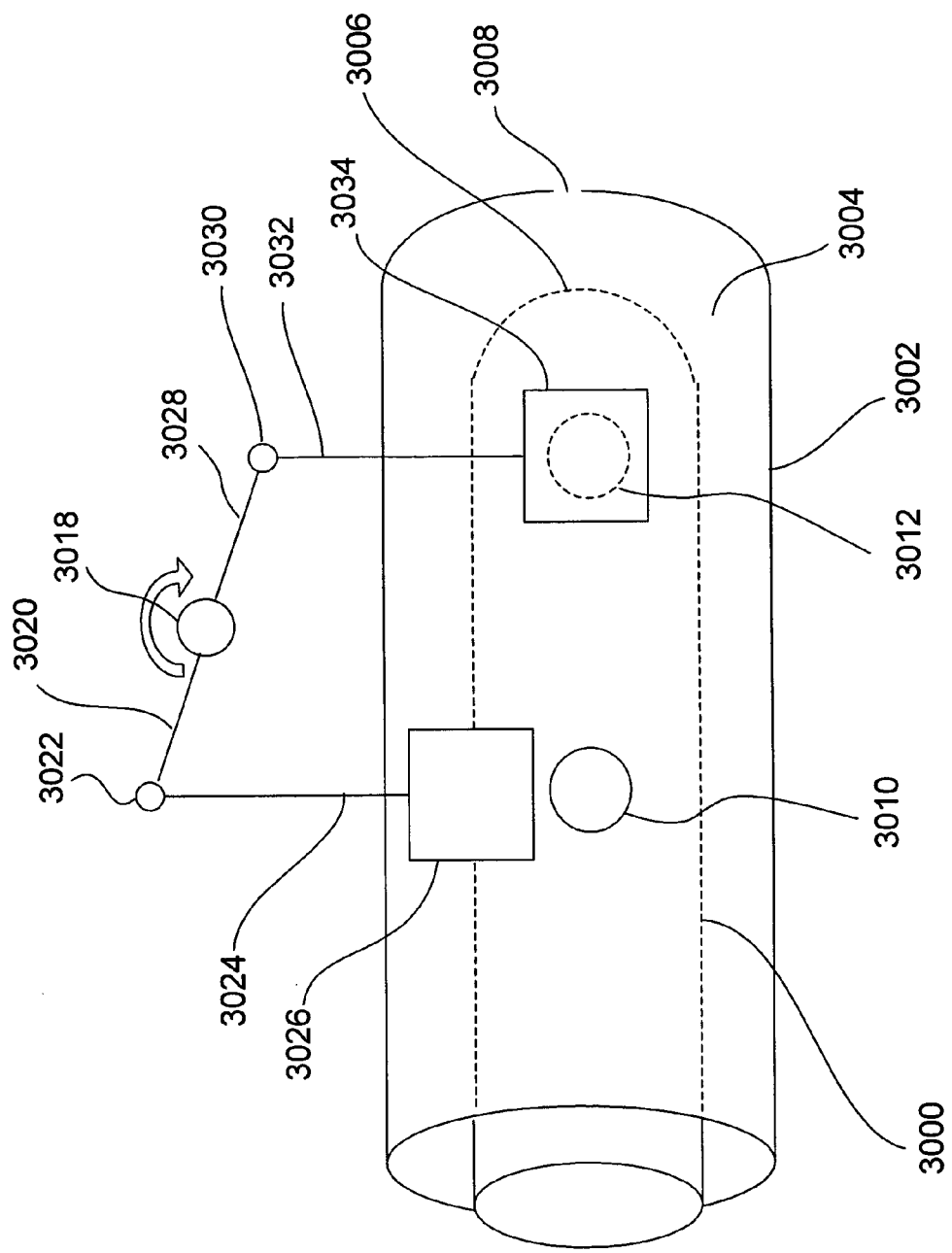
FIG. 31b shows the system of FIG. 31a in a second mode of operation

Referring now to FIG. 31*b*, shown is the system of FIG. 31*a* while in a second mode of operation. Elements labeled with the same numerals have the same function as those illustrated in FIG. 31*a*. In particular, FIG. 31*b* shows the system of FIG. 31*a* subsequent to clock-wise rotation of the actuator interface 3018. In FIG. 31*b*, the first cover portion 3026 is in the second position in which the ion inlet orifice 3010 is uncovered, and the second cover portion 3034 is in the second position in which the ion inlet orifice 3012 is covered. In the second mode of operation, ions that are produced at the ionization source adjacent to the ion inlet orifice 3010 are directed through the ion inlet orifice 3010 and into the analyzer region 3004, whilst ions that are produced at the ionization source adjacent to the ion inlet orifice 3012 are directed toward the second cover portion 3034 where they are neutralized and the charge is carried away via the not illustrated electrical connections to the second cover portion 3034.

Referring now to both FIG. 31a and FIG. 31b, it is an advantage of the system according to the instant embodiment that precise rotational positioning of the actuator interface 3018 is not necessary. In particular, the first cover portion 3026 is moved from a first position in which the first cover portion 3026 overlaps with a substantial area of the outer electrode about the ion inlet orifice 3010, to a second position in which the first cover portion 3026 is substantially withdrawn from the vicinity of the ion inlet orifice 3010. The initial and final positions of the first cover portion are not critical, provided that the ion inlet orifice 3010 is covered when the first cover portion 3026 is in the first position and is uncovered when the first cover portion 3026 is in the second position. There is no opening through the first cover portion that requires precise alignment with the ion inlet orifice 3010 to support ion introduction therethrough, but rather the entire first cover portion 3026 is simply translated out of the path between the ionization source and the ion inlet orifice 3010, so as to uncover the ion inlet orifice for supporting ion introduction therethrough. Accordingly, the inlet selection system according to the instant embodiment is tolerant of, or insensitive to, variations in the rotational position of the actuator interface 3018 from one inlet selection cycle to another. This supports more rapid switching and more reliable switching between ion inlet orifices over time, compared to systems relying upon precise alignment of an opening with the ion inlet orifices of the FAIMS device.

Referring to FIG. 32, shown is a simplified schematic view of a FAIMS analyzer including an array of rod-shaped electrodes, taken along a first direction. In FIG. 32, the first direction is along the length of rod-shaped electrodes of the array. The FAIMS analyzer, which is shown generally at 3210 in FIG. 32, includes an ion inlet plate 3212 with an ion inlet 3214, and an ion outlet plate 3216 with an ion outlet 3218. A not illustrated electrically insulating material supports the plates 3212 and 3216 in a spaced-apart parallel arrangement, one relative to the other. A plurality of rods, shown generally at 3220 in FIG. 32, is disposed within the space between the ion inlet plate 3212 and the ion outlet plate 3216. The plurality of rods 3220 is supported by the not illustrated electrically insulating material in a spaced-apart arrangement, so as to define an analytical gap 3226 between adjacent rods for allowing ions that are introduced via the ion inlet 3214 to propagate in a direction generally toward the ion outlet 3218. Those portions of the plurality of rods 3220 that are adjacent to, and that define the analytical gap 3226 are referred to generally as "electrode portions".

Preferably, individual rods are arranged approximately parallel one to another, but it is to be understood that small deviations from parallel are also envisaged. As will be obvious to one of skill in the art, a plurality of different ion paths exists between the ion inlet 3214 and the ion outlet 3218. Furthermore, ions travelling along different ion paths may travel different distances between the ion inlet 3214 and the ion outlet 3218, as some of the different ion paths through the plurality of rods 3220 are more torturous than others.

For ease of discussion, a second direction in the FAIMS analyzer is defined by the vertical path between the ion inlet 3214 and the ion outlet 3218 and a third direction is defined to be normal to both the first and second directions. Referring again FIG. 32, the third direction is the width (left to right) of the electrode array.

Preferably, the rods are relatively long in the first direction compared to the second direction so as to minimize the number of ions that approach the electrically insulating material supporting the rods. Ions hitting the electrically insulating material create a charged surface thereon. Electrical discharges within the FAIMS analyzer should be avoided as they may create burn tracks in the insulating material which can act as short circuits. Electrical discharges may also lead to chemical contamination of the FAIMS analyzer caused by the degradation of the insulating material.

Individual rods of the plurality of rods 3220 are categorized into two different types of rods 3222 and 3224, which are identified conveniently by the electric voltages applied to them using a not illustrated electrical controller. Rods 3222, shown as crosshatched circles in FIG. 32, have electrical connectors through which an asymmetric waveform is applied. The remaining rods 3224 are shown as open circles in FIG. 32. A dc voltage is applied to either or both of rods 3222 and rods 3224 so that a dc potential difference, identically referred to as the compensation voltage, exists between the two types of rods. Each type of rod corresponds to one of the first or second electrode of a FAIMS analyzer. Furthermore, the rods 3222, the rods 3224, the ion inlet plate 3212 and the ion outlet plate 3216 have electrical connectors through which a dc voltage is applied. Alternately the electrical connectors may be used to set any of rods 3222, rods 3224, the ion inlet plate 3212 and the ion outlet plate 3216 at ground potential. The dc voltages applied to each one of the rods 3224, the ion inlet plate 3212 and the ion outlet plate 3216 are not necessarily identical, since the ion inlet plate 3212 preferably is biased to "push" ions in a direction toward the plurality of rods 3220, whilst the ion outlet plate 3216 preferably is biased to "pull" ions away from the plurality of rods 3220 and in a direction toward the ion outlet 3218. Of course, many other possible combinations of applying the dc voltages and the asymmetric waveform voltage to the individual rods of the FAIMS analyzer 3210 will be apparent to one of skill in the art. It should be understood that the above example is intended to serve as a specific and non-limiting example to facilitate a more complete understanding of the instant invention.

Referring still to FIG. 32, preferably a flow of a gas is provided, during use, between a region proximate the ion inlet 3214, through the plurality of rods 3220, and out of the device 3210 via ion outlet 3218. Preferably, the FAIMS analyzer is substantially gas tight so that the majority of gas exits via the ion outlet 3218. Ions that are entrained in the flow of a gas are carried through the analytical gap 3226 between adjacent rods, toward a region 3238 adjacent the ion outlet 3218, and out through ion outlet 3218 along with the flow of a gas. Since the FAIMS analyzer 3210 transports and separates ions based upon the FAIMS principle, only a sub-set of the ions that are introduced through the ion inlet 3214 are selectively transported to the ion outlet 3218. A portion of the selectively transported ions pass through the ion outlet 3218, and may be transported to one of an ion detection system, another ion mobility spectrometer, or alternatively to a mass spectrometer for further analysis.

Referring now to FIG. 33, shown is schematic view of a portion of the FAIMS analyzer of FIG. 32, taken along the first direction. Elements labeled with the same numerals have the same function as those illustrated at FIG. 32. For the purpose of discussing FIG. 33, it is assumed that the asymmetric waveform with peak voltage DV and the dc compensation voltage (CV) are both applied to rods 3222, whilst rods 3224 are maintained at ground potential. Of course, other combinations of applying the DV and CV will be envisaged by one of skill in the art.

Referring still to FIG. 33, application of the DV and CV to the rods 3222 establishes an electric field within the analytical gap 3226 between adjacent rods. The electric field that is established between any two adjacent rods includes a variable component relating to the application of the asymmetric waveform voltage, and a constant in time component relating to the applied dc voltage. Furthermore, the application of the asymmetric waveform voltage results in an electric field that is stronger in one polarity than in the other. Since the mobility of an ion may be higher or lower in the stronger field than in the lower field of opposite polarity, the oscillation of the ion may cause it to drift towards one of the rods. The dc component of the electric field is applied in order to counteract, or compensate, for this drift. Under the correct combination of applied asymmetric waveform voltage and applied dc voltage difference between the rods, ions with an appropriate ratio of mobility at high electric field strength to mobility at low electric field strength are in a balanced condition. In other words, the electric field arising from the applied CV just matches the drift effect caused by application of the waveform with peak voltage DV. For an ion with an appropriate field-dependence of the ratio of mobility at high field strength to mobility at low field strength, the application of the DV and CV to the rods 3222, with the other rods 3224 held at ground potential, results in a focusing region 3328 surrounding each one of the rods 3222.

The focusing region 3328 around each rod 3222 is defined in terms of the motion of the ions in the vicinity of this region. If, for example, an ion of interest is closer to the rod 3222 than to the focusing region 3328, the effect of the asymmetric waveform voltage is to push the ion away from the rod 3222. Alternatively, if the ion is located beyond the focusing region 3328, the ion tends to move generally towards the rod 3222. In other words, the focusing region 3328 is located a distance from the rod 3222 at which the effect of the waveform that pushes the ions away from the rod 3222 is exactly balanced by the attractive force towards rod 3222 caused by the compensation voltage. Although this balance point actually is an infinitely thin two-dimensional surface, the regions 3328 surrounding each electrode 3222 are illustrated in FIG. 33 with an exaggerated thickness in recognition of the fact that ions oscillate within the electric field, and therefore are distributed over some range of distances from the rod 3222. In addition, the ions are also under the influence of diffusion, ion-ion repulsion, etc., which cause the ions to be located over some finite range of distances rather than being compressed within the infinitely thin two-dimensional surface.

In the absence of a gas flow through the plurality of rods 3220, the ions are expected to migrate to and collect within the focus regions 3328 around the rods 3222 to which the DV and CV are applied. Moreover, the ions become distributed at all locations equally around the circumference of the focus region 3328. Accordingly, a flow of a gas 3330 is provided through the analytical gap 3226 between the rods, to transport the ions through the analytical gap 3226 and toward the ion outlet 3218. The introduction of a flow of gas 3330 results in one of two possible changes to the distribution of ions within the plurality of rods 3220, depending upon the rate of the flow of a gas. At low flow rates, the ions are directed around the circumference of the rods 3222 following the curvature of the focus region 3328. In effect, the flow of a gas 3330 pushes the ions predominantly to the downstream side of the rods 3222. This is possible because there are no barriers to motion of the ions around the focus region 3328. At higher gas flow rates, the ions are no longer constrained to the focus regions 3328, but instead are pulled out of the focus region 3328 by the movement of the flow of a gas 3330. Advantageously, the gas flow 3330 carries selectively transmitted ions away from the plurality of rods 3220 and toward the ion outlet 3218.

Referring now to FIG. 34, illustrated is the effect of electric fields within the FAIMS analyzer of FIG. 32 on the trajectory of ions. Elements labeled with the same numerals have the same function as those illustrated at FIG. 32 and FIG. 33. For the purpose of discussing FIG. 34, it is once again assumed that the asymmetric waveform voltage with peak voltage DV and the dc compensation voltage (CV) are both applied to rods 3222, whilst rods 3224 are maintained at ground potential. In particular, the peak voltage DV is of positive polarity, whereas the CV is of negative polarity. Of course, other combinations of applying the DV and CV will be envisaged easily by one of skill in the art.

Ions 3432 are produced at a not illustrated ionization source, such as for example one of an electrospray ionization source, a corona discharge ionization source, a radioactive nickel foil ionization source, and a MALDI ionization source. Typically, the ions 3432 include at least two different types of ions, such as for example an ion of interest 3432a and an ion that is other than of interest 3432b. The ions 3432 introduced into the FAIMS analyzer become entrained in the flow of a gas 3330, which carries the ions into the analytical gap 3226 between adjacent rods of the plurality of rods 3220. Ions with the correct behavior at high electric field relative to low electric field are selectively transmitted through the analytical gap 3226, whilst other types of ions collide with the rods and are lost. To this end, conditions are selected within the FAIMS analyzer 3210 for transmitting the ions of interest 3432a through the analytical gap 3226.

Two simplified ion trajectories are shown in FIG. 34 in order to better illustrate the behavior of the ions within the analytical gap 3226 of the FAIMS analyzer 3210. Here, and elsewhere, the rapid oscillations of the ion due to the applied asymmetric waveform voltage are not shown on the trajectory. In the instant example, the flow of gas 3330 through the plurality of rods 3220 is sufficiently rapid to pull the ions away from the focus regions 3328 around the rods 3222. In general, positive ions 3432 approaching the rods 3222,3224 are pulled in a direction toward the rods 3222 as a result of the CV of negative polarity (for example) that is applied to the rods 3222. An ion moving along ion trajectory 3434 approaches a first focus region 3328a of one of the rods 3222. The flow of a gas 3330 directs the ion around the rod 3222 following the focus region 3328a, until the ion eventually escapes from the focus region 3328a. The combined effect of the gas flow 3330 and the electric field is to move the ion away from the first focus region 3328a and toward a second focus region 3328b. Provided the ion does not collide with an electrode, the ion eventually traverses the plurality of rods 3220 in a step wise fashion, moving from focus region 3328b to 3328c, from focus region 3328c to 3328d, and from focus region 3328d to the ion outlet 3218 of FIG. 32. Other ions move along other trajectories, such as for example trajectory 3436, in an analogous manner.

Referring still to FIG. 34, the two trajectories 3434 and 3436 pass through the focus region of the same rod 3222 in the vicinity of the region 3438. Ions moving along the trajectories 3434 and 3436 are much closer to each other within the region 3438 than when they entered the plurality of rods 3220.

Accordingly, the FAIMS analyzer 3210 serves to "funnel" the selectively transmitted ions into a relatively narrow region of space for extraction through the ion outlet 3218. Advantageously, this funnelling effect increases ion transmission efficiency by minimizing ion loss as a result of collisions with the ion outlet plate 3216. Furthermore, the flow of a gas 3330 can be used to assist in this funnel effect if the gas flows through the plurality of parallel rods 3220 towards a single ion outlet 3218. Optionally, this funneling effect is further enhanced by establishing a potential gradient within the FAIMS analyzer 3210, for example by the application of different dc voltages to different rods 3224 of the plurality of rods 3220 across the width of the FAIMS analyzer for directing the ions generally toward the center of FIG. 34. Further optionally, ion trajectories are manipulated by the application of predetermined dc voltages to different rods 3224, so as to establish an appropriate potential gradient for affecting ion trajectories in a desired manner. In this way, ions are preferentially directed along a desired average ion flow path. For instance, by application of appropriate potentials ions are preferentially directed along the average ion flow path 3436. By application of different appropriate potentials, ions are optionally directed along the average ion flow path 3434, which in this example is a less direct route between the ion inlet 3214 and the ion outlet 3218, and therefore is longer compared to the average ion flow path 3436. Of course, by application of still other appropriate potentials, other not illustrated average ion flow paths having even longer lengths are defined between the ion inlet 3214 and the ion outlet 3218.

The system described with reference to FIGS. 32 through 34 is an example of a FAIMS including a plurality of first electrode portions and a plurality of second electrode portions interleaved in a repeating sequence with the plurality of first electrode portions. In particular, each first electrode portion of the plurality of first electrode portions has a first length and an outer surface that is at least partially curved in a direction transverse to the first length. Similarly, each second electrode portion of the plurality of second electrode portions has a second length and an outer surface that is at least partially curved in a direction transverse to the second length. The arrangement is such that a space between the outer surface of a first electrode portion and the outer surface of an adjacent second electrode portion defines a portion of the FAIMS analyzer region. A controller including an electrical controller is provided for electrically coupling to at least one of the plurality of first electrode portions and the plurality of second electrode portions. In use, the electrical controller selectably applies a predetermined asymmetric waveform voltage and direct current voltage between predetermined first and second electrode portions to define a first average ion flow path having a first length, and between different predetermined first and second electrode portions to define a second average ion flow path having a second length that is different than the first length.

Figure 35A:
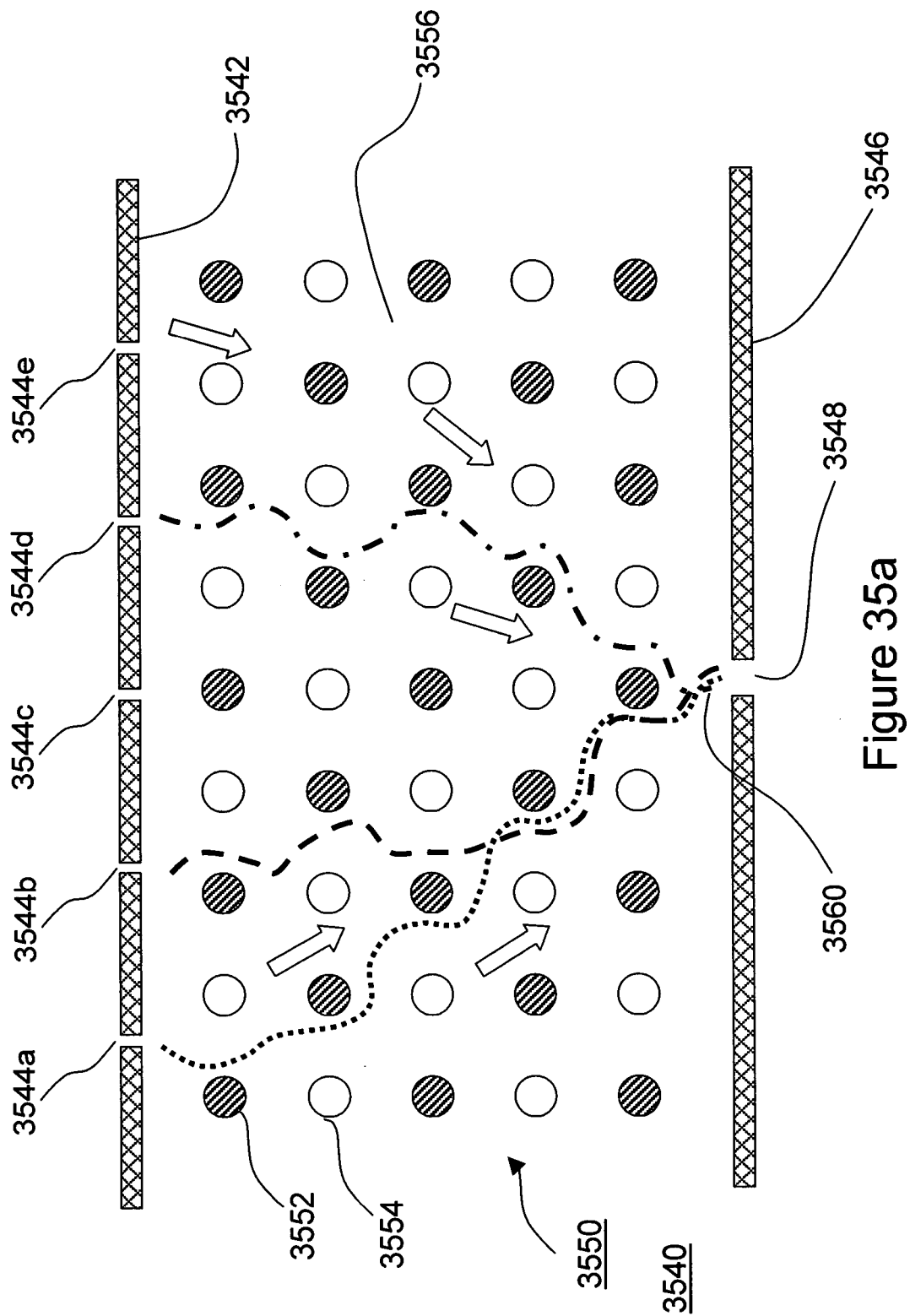
FIG. 35a is a simplified schematic view of another FAIMS analyzer including an array of rod-shaped electrodes according to another embodiment of the instant invention, taken along the first direction.

Referring now to FIG. 35a, shown is a simplified schematic view of another FAIMS analyzer including an array of rod-shaped electrodes according to another embodiment of the instant invention, taken along a first direction. In FIG. 35a, the first direction is along the length of rod-shaped electrodes of the array. The FAIMS analyzer, which is shown generally at 3540 in FIG. 35a, includes a plurality of ion inlets 3544a, 3544b, 3544c, 3544d, and 3544e that are provided in an ion inlet plate 3542, and a single ion outlet 3548 is provided in an ion outlet plate 3546. A not illustrated electrically insulating material supports the plates 3542 and 3546 in a spaced-apart parallel arrangement, one relative to the other. A plurality of rods, shown generally at 3550, is disposed within the space between the ion inlet plate 3542 and the ion outlet plate 3546. The plurality of rods 3550 is supported by the not illustrated electrically insulating material in a spaced-apart arrangement, so as to define an analytical gap 3556 between adjacent rods for allowing ions that are introduced via the plurality of ion inlets 3544a, 3544b, 3544c, 3544d, and 3544e to propagate in a direction generally toward the ion outlet 3548.

Individual rods of the plurality of rods 3550 are categorized into two different types of rods 3552 and 3554, which are identified conveniently by the electric voltages applied to them using a not illustrated electrical controller. Rods 3552, shown as crosshatched circles in FIG. 35a, have electrical connectors through which an asymmetric waveform voltage is applied. The remaining rods 3554 are shown as open circles in FIG. 35a. A dc voltage is applied to either or both of rods 3552 and rods 3554 so that a dc potential difference, identically referred to as the compensation voltage, exists between the two types of rods. Each type of rod corresponds to one of the first or second electrode of a FAIMS analyzer. Furthermore, the rods 3552, the rods 3554, the ion inlet plate 3542 and the ion outlet plate 3546 have electrical connectors through which a dc voltage is applied. Alternately the electrical connectors may be used to set any of rods 3552, rods 3554, the ion inlet plate 3542 and the ion outlet plate 3546 at ground potential. The dc voltages applied to each one of the rods 3554, the ion inlet plate 3542 and the ion outlet plate 3546 are not necessarily identical, since the ion inlet plate 3542 preferably is biased to "push" ions in a direction toward the plurality of rods 3550, whilst the ion outlet plate 3546 preferably is biased to "pull" ions away from the plurality of rods 3550 and in a direction toward the ion outlet 3548. Of course, many other possible combinations of applying the dc voltages and the asymmetric waveform voltage to the individual rods of the FAIMS analyzer 3540 will be apparent to one of skill in the art. It should be understood that the above example is intended to serve as a specific and non-limiting example to facilitate a more complete understanding of the instant invention.

Figure 35B:
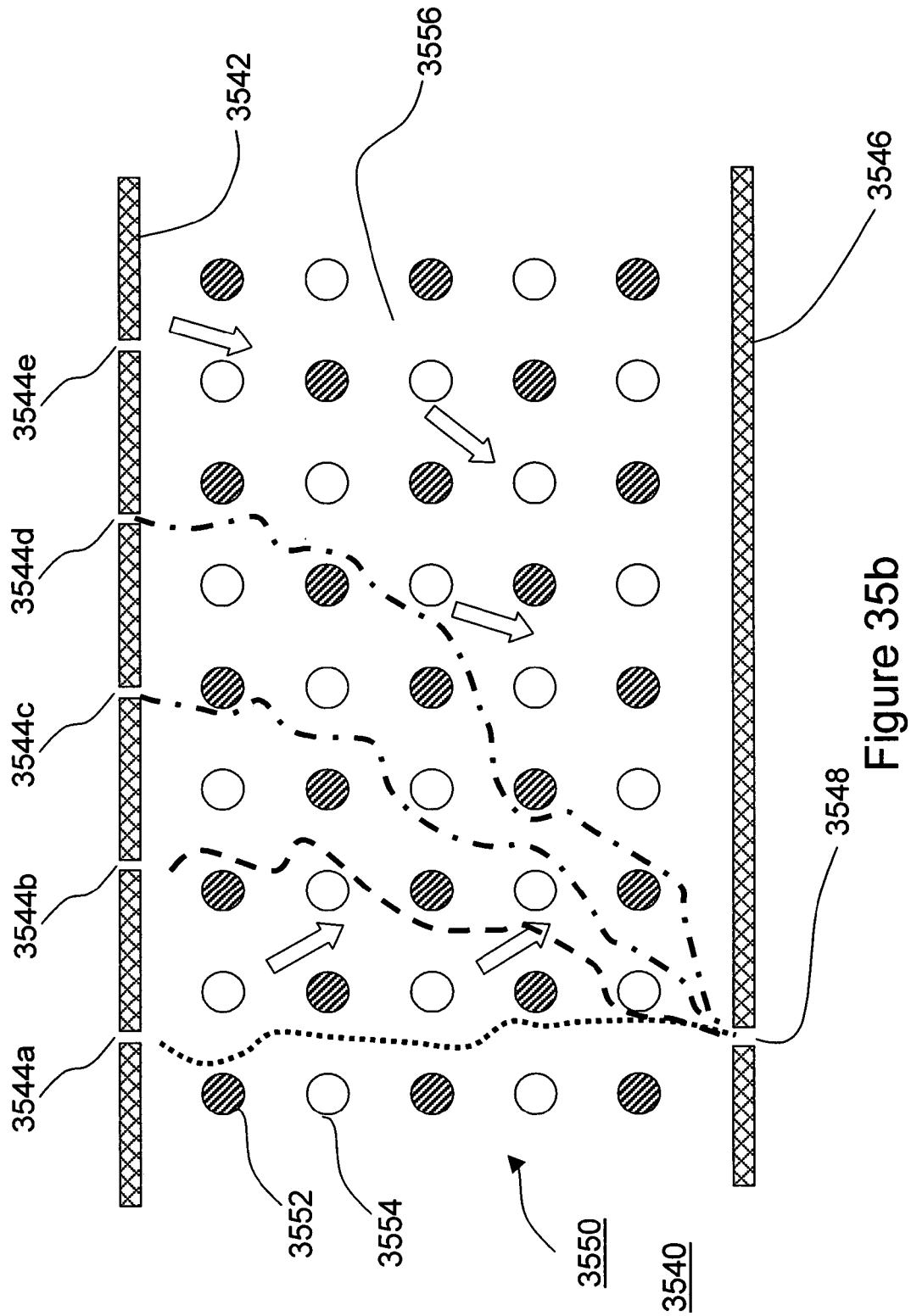
FIG. 35b is a simplified schematic view of another FAIMS analyzer including an array of rod-shaped electrodes according to another embodiment of the instant invention, taken along the first direction.

Referring still to FIG. 35a, the funnel effect that was described above is shown being used to advantage. Ions introduced through each different ion inlet 3544a, 3544b, 3544c, 3544d, and 3544e follow a different trajectory, or average ion flow path. Three such trajectories, or average ion flow paths, are shown in FIG. 35a, which converge toward the single ion outlet 3548 in ion outlet plate 3546. The arrows in FIG. 35a represent gas flowing through the FAIMS analyzer 3540. For example, a flow of gas is introduced through each of the ion inlets 3544a, 3544b, 3544c, 3544d, and 3544e along with the ions. Optionally, supplemental gas flows are introduced through not illustrated gas inlets disposed along the sides of the parallel-rod array FAIMS analyzer 3540. Since there is only one outlet from the FAIMS analyzer 3540, all gas flows through the device, and consequently all ion trajectories, tend to converge at region 3560 adjacent to the ion outlet 3548. Advantageously, near the ion inlet plate 3542 the ions are spread out over a large volume of space, thereby minimizing ion-ion repulsion and space-charge forces. As the ions move along the different trajectories through the analytical gap 3556, some ions collide with the rods and are lost. In particular, those ions that are other than of interest are lost relatively rapidly. Simultaneously, the ions moving along the different trajectories are "funneled" toward a smaller volume of space 3560 prior to being extracted through the ion outlet 3548. Since the number of ions that reach the volume of space 3560 is small relative to the number of ions that are introduced into the analyzer 3540 via ion inlets 3544a, 3544b, 3544c, 3544d, and 3544e, ion-ion repulsion and space-charge forces within the volume of space 3560 are minimized. Optionally, this funneling effect is further enhanced by establishing a potential gradient within the FAIMS analyzer 3540, for example by using a controller including an electrical controller for applying different dc voltages to different rods 3554 of the plurality of rods 3550. In this way, for example, ions are guided generally toward the single ion outlet 3548 in ion outlet plate 3546. Further optionally, ion trajectories are manipulated within other regions of the FAIMS analyzer 3540 by the application of predetermined dc voltages to different rods 3554, so as to establish an appropriate potential gradient for affecting ion trajectories in a desired manner. In this way, ions are preferentially directed along a desired average ion flow path. For instance, by application of appropriate potentials ions are preferentially directed along one of the average ion flow paths shown in FIG. 35a between the ion inlets 3544a, 3544b, 3544c, 3544d, and 3544e and the single ion outlet 3548. By application of different appropriate potentials, ions are optionally directed along another average ion flow path between the ion inlets 3544a, 3544b, 3544c, 3544d, and 3544e and the single ion outlet 3548. As shown in FIG. 35a, some of the different average ion flow paths between the ion inlets 3544a, 3544b, 3544c, 3544d, and 3544e and the single ion outlet 3548 have lengths that differ one to the next. That said, due to the symmetry of the device shown in FIG. 35a, the average ion flow path between ion inlet 3544b and ion outlet 3548 is substantially equal to the average ion flow path between ion inlet 3544d and ion outlet 3548, for example. Optionally, the device shown in FIG. 35a is constructed such that the ion outlet 3548 is aligned with the ion inlet 3544a instead of the ion inlet 3544c, as shown in FIG. 35b. In the system shown in FIG. 35b, the average ion flow path between the ion inlet 3544d and the ion outlet 3548 is substantially longer than the average ion flow path between the ion inlet 3544a and the ion outlet 3548.

Referring now to FIG. 36, shown is a simplified schematic view of yet another FAIMS analyzer including an array of rod-shaped electrodes, taken along the first direction. In FIG. 36, the first direction is along the length of rod-shaped electrodes of the array. The FAIMS analyzer, which is shown generally at 3670 in FIG. 36, includes an ion inlet plate 3672 with an ion inlet 3674, and an ion outlet plate 3676 with an ion outlet 3678. A not illustrated electrically insulating material supports the plates 3672 and 3676 in a spaced-apart parallel arrangement, one relative to the other. A plurality of rods, shown generally at 3680, is disposed within the space between the ion inlet plate 3672 and the ion outlet plate 3676. The plurality of rods 3680 is supported by the not illustrated electrically insulating material in a spaced-apart arrangement, so as to define an analytical gap 3686 between adjacent rods for allowing ions that are introduced via the ion inlet 3674 to propagate in a direction generally toward the ion outlet 3678. As will be obvious to one of skill in the art, a plurality of different ion paths, or average ion flow paths, exists between the ion inlet 3674 and the ion outlet 3678. Furthermore, ions travelling along different ion paths may travel different distances between the ion inlet 3674 and the ion outlet 3678, as some of the different ion paths through the plurality of rods 3680 are more torturous than others.

Individual rods of the plurality of rods 3680 are categorized into two different types of rods 3682 and 3684, which are identified conveniently by the electric voltages applied to them using a not illustrated electrical controller. Rods 3682, shown as crosshatched circles in FIG. 36, have electrical connectors through which an asymmetric waveform voltage is applied. The remaining rods 3684 are shown as open circles in FIG. 36. A dc voltage is applied to either or both of rods 3682 and rods 3684 so that a dc potential difference, identically referred to as the compensation voltage, exists between the two types of rods. Each type of rod corresponds to one of the first or second electrode of a FAIMS analyzer. Furthermore, the rods 3682, the rods 3684, the ion inlet plate 3672 and the ion outlet plate 3676 have electrical connectors through which a dc voltage is applied. Alternately the electrical connectors may be used to set any of rods 3622, rods 3624, the ion inlet plate 3612 and the ion outlet plate 3616 at ground potential. The dc voltages applied to each one of the rods 3684, the ion inlet plate 3672 and the ion outlet plate 3676 are not necessarily identical, since the ion inlet plate 3672 preferably is biased to "push" ions in a direction toward the plurality of rods 3680, whilst the ion outlet plate 3676 preferably is biased to "pull" ions away from the plurality of rods 3680 and in a direction toward the ion outlet 3678. Of course, many other possible combinations of applying the dc voltages and the asymmetric waveform voltage to the individual rods of the FAIMS analyzer 3670 will be apparent to one of skill in the art. It should be understood that the above example is intended to serve as a specific and non-limiting example to facilitate a more complete understanding of the instant invention.

Referring now to FIG. 32 and FIG. 36, it is clear that the placement of the rods is not important to the overall motion of the ions through a FAIMS analyzer according to the instant invention. Rather, it is the fact that the array of rods is symmetrical around each rod 3222, 3682 to which the asymmetric waveform voltage is applied. When such a condition is satisfied, the ions may travel in any direction that the gas is flowing and experience approximately identical conditions. This is illustrated by a comparison of FIG. 32 and FIG. 36. In particular, the rods in FIG. 36 are arranged in a second optional pattern, different from the cubic array shown in FIG. 32 by rotation of the symmetric pattern of rods by about 45 degrees. Of course, other angels of rotation are also envisaged.

Again referring to FIG. 36 illustrates an advantage of this particular arrangement of rods. In particular, the gas flow carries an ion from a focus region around a rod to which is applied the asymmetric waveform voltage, to a focus region around a next rod in the path of gas flow to which is applied the asymmetric waveform voltage. If the ion inlet 3674 is aligned with one of the electrodes 3682 to which the asymmetric waveform voltage and compensation voltages are applied, the ion can easily follow a trajectory 3688 to the exit orifice 3678. This undulating motion maximizes the ion's travel through focus regions and the ion transmission efficiency is very high, since no part of the trajectory permits the ion sufficient freedom to diffuse toward and collide with a rod. Trajectory calculations show that the fields are always moving the ions away from colliding with the rods.

Figures 37A, 37B:
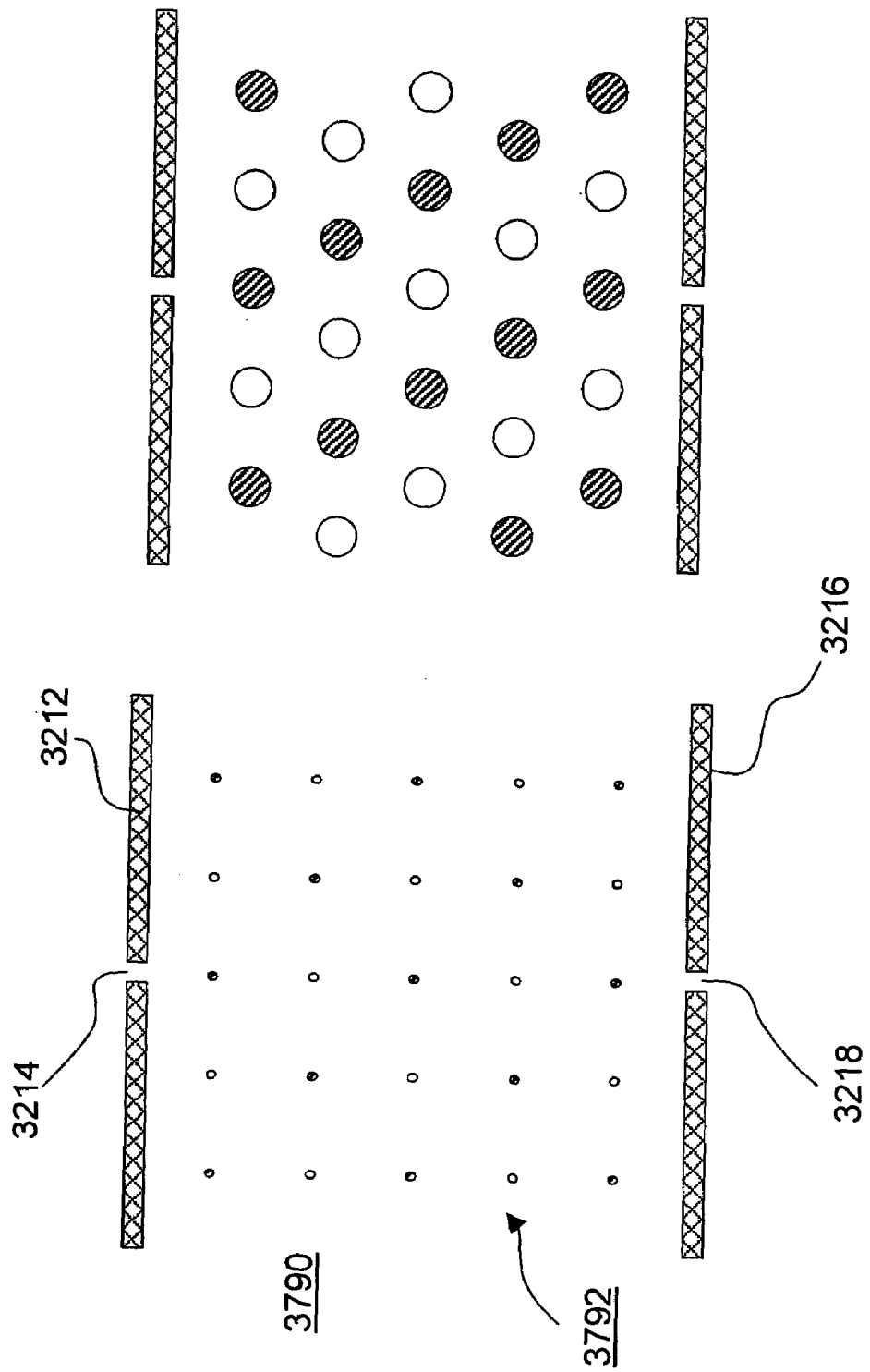
FIG. 37a is a simplified schematic view of a FAIMS analyzer according to an embodiment of the instant invention including a plurality of wire electrodes.
FIG. 37b is a simplified schematic view of a FAIMS analyzer according to an embodiment of the instant invention including an array of rod-shaped electrodes in a first closest packing arrangement.
Figure 37C:
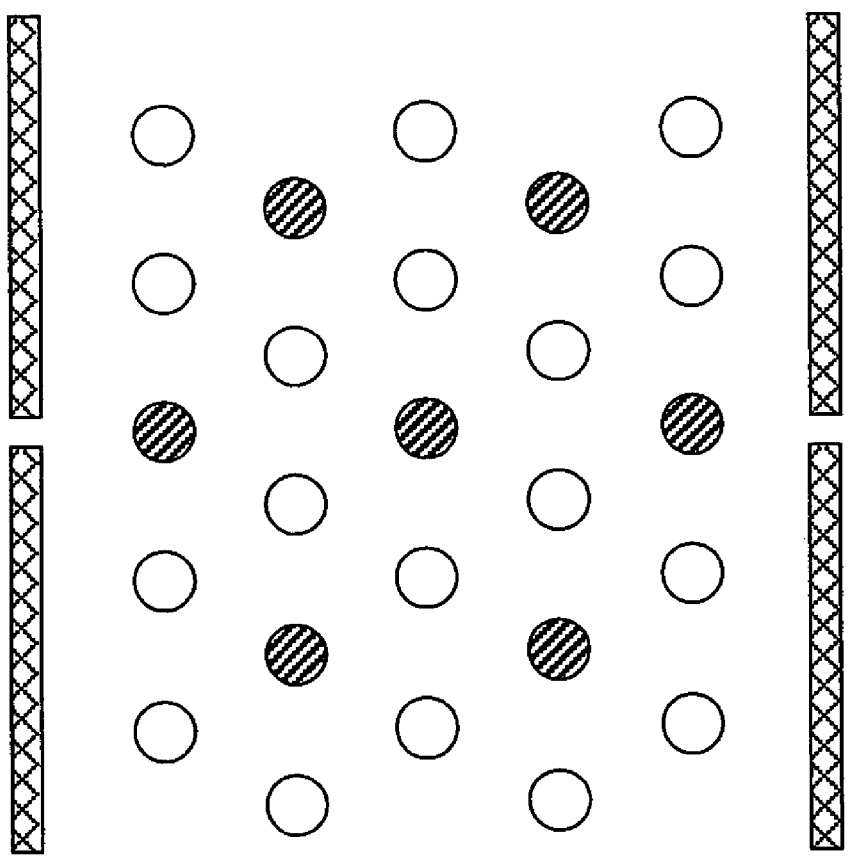
FIG. 37c is a simplified schematic view of a FAIMS analyzer according to an embodiment of the instant invention including an array of rod-shaped electrodes in a second closest packing arrangement.
Figure 37D:
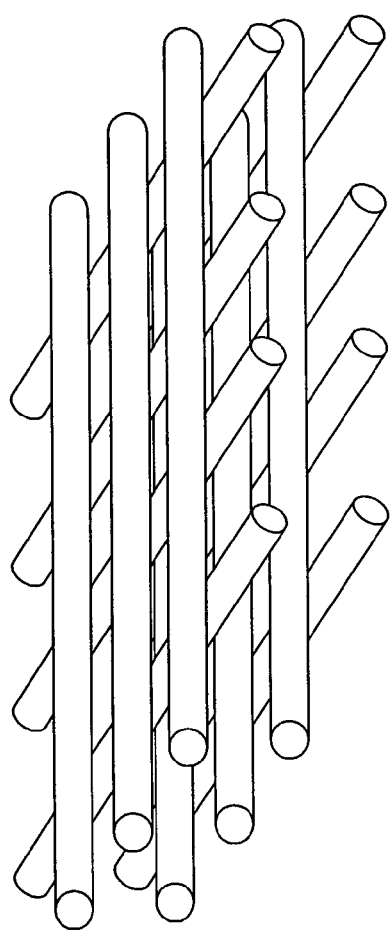
FIG. 37d is a simplified schematic view of a FAIMS analyzer according to an embodiment of the instant invention including a two-dimensional layered array of rod-shaped electrodes.
Figure 37E:
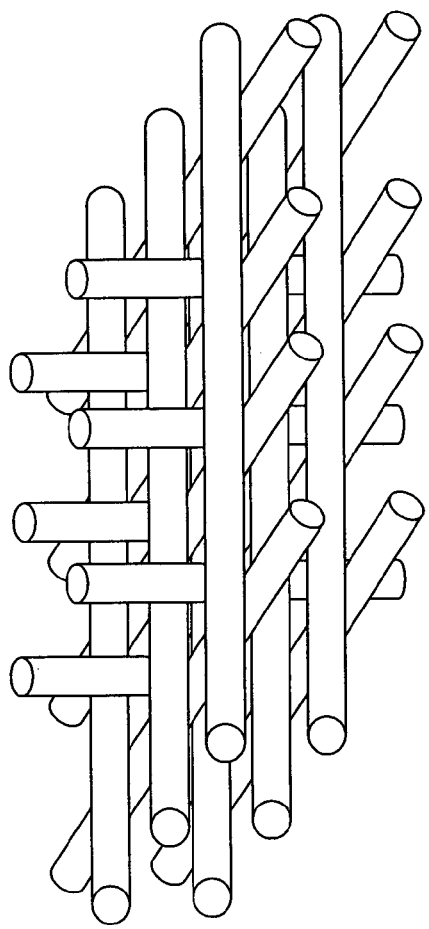
FIG. 37e is a simplified schematic view of a FAIMS analyzer according to an embodiment of the instant invention including a three-dimensional layered array of rod-shaped electrodes.

In each of the above embodiments, electrodes are provided in the form of rods to which are applied the various electric voltages. Optionally, the electrodes are provided in the form of wires, or in the form of rods having a smaller diameter relative to the inter-rod spacing than has been described above. FIG. 37a shows a simplified schematic view of a FAIMS analyzer 3790 according to an embodiment of the instant invention including a plurality of wire electrodes 3792. Elements labeled with the same numerals have the same function as those illustrated at FIG. 32.

In yet another optional arrangement the rods may be close packed so that six other rods symmetrically surround each rod as shown for example at FIGS. 6b and 6c, or arranged in layers of rods where each layer is perpendicular to the next as shown at FIGS. 6d and 6e. Of course, other similar arrangements of the rods may be easily envisaged, without departing from the spirit and scope of the instant invention.

Further optionally, the rods that are shown in any of FIGS. 32 through 37e are other than circular in cross-section. For instance, optionally the rods are elliptical in cross section.

Still further optionally, the rods that are shown in any of FIGS. 32 through 37e are hollow and fabricated from a conductive material. Optionally, the rods include a non-conductive core that is one of hollow and solid, with a conductive outer surface.

Referring now to FIG. 38, shown is a simplified exploded view of yet another FAIMS analyzer including an array of rod-shaped electrodes according to the instant invention, including two sets of electrode rods. In particular, a plurality of rods 5110 is mounted to a same plate 5112, which includes an electrical contact for connection, during use, to an electrical controller capable of applying an asymmetric waveform voltage to the same plate 5112. Optionally, a CV is applied to the same plate 5112 via an electrical contact. Similarly, a second plurality of rods 5114 is mounted to a different plate 5116, which includes an electrical contact for connection, during use, to an electrical controller capable of applying at least a dc voltage to the different plate 5116. Advantageously, only a single electrical contact is require to apply the asymmetric waveform voltage to each rod of the plurality of rods 5110 via the same plate 5112. Similarly, only a single electrical contact is required to apply the dc voltage to each rod of the plurality of rods 5114 via the same plate 5116. Optionally, each rod of the plurality of rods 5110 and each rod of the second plurality of rods 5114 protrudes through an electrically insulating material 5118, which supports the rods and maintains a desired spacing between the rods. Furthermore, the electrically insulating material insulates rods of the first plurality of rods 5110 from the different plate 5116, and insulates rods of the second plurality of rods 5114 from the same plate 5112. Optionally, a free end of each rod terminates at an electrically insulating endcap member.

Referring now to FIG. 39a, shown is an exploded isometric view of the FAIMS analyzer of FIG. 38. FIG. 39b shows an isometric view of the FAIMS analyzer of FIG. 38. The electrically insulating material 5118 is omitted in FIGS. 39a and 39b for improved clarity. Rods of the first plurality of rods 5110 are mounted to the same plate 5112 and rods of the second plurality of rods 5114 are mounted to the different plate 5116 such that, when in the assembled condition shown in FIG. 39b, each rod of the first plurality of rods is adjacent to one or more rods of the second plurality of rods. The block arrows in FIG. 39b indicate the direction of gas flow through analyzer. Of course, rods mounted to one of the same plate 5112 and the different plate 5116 are electrically insulated from the other one of the same plate 5112 and the different plate 5116 such as optionally by the not illustrated insulating material 5118.

Figures 40A, 40B:
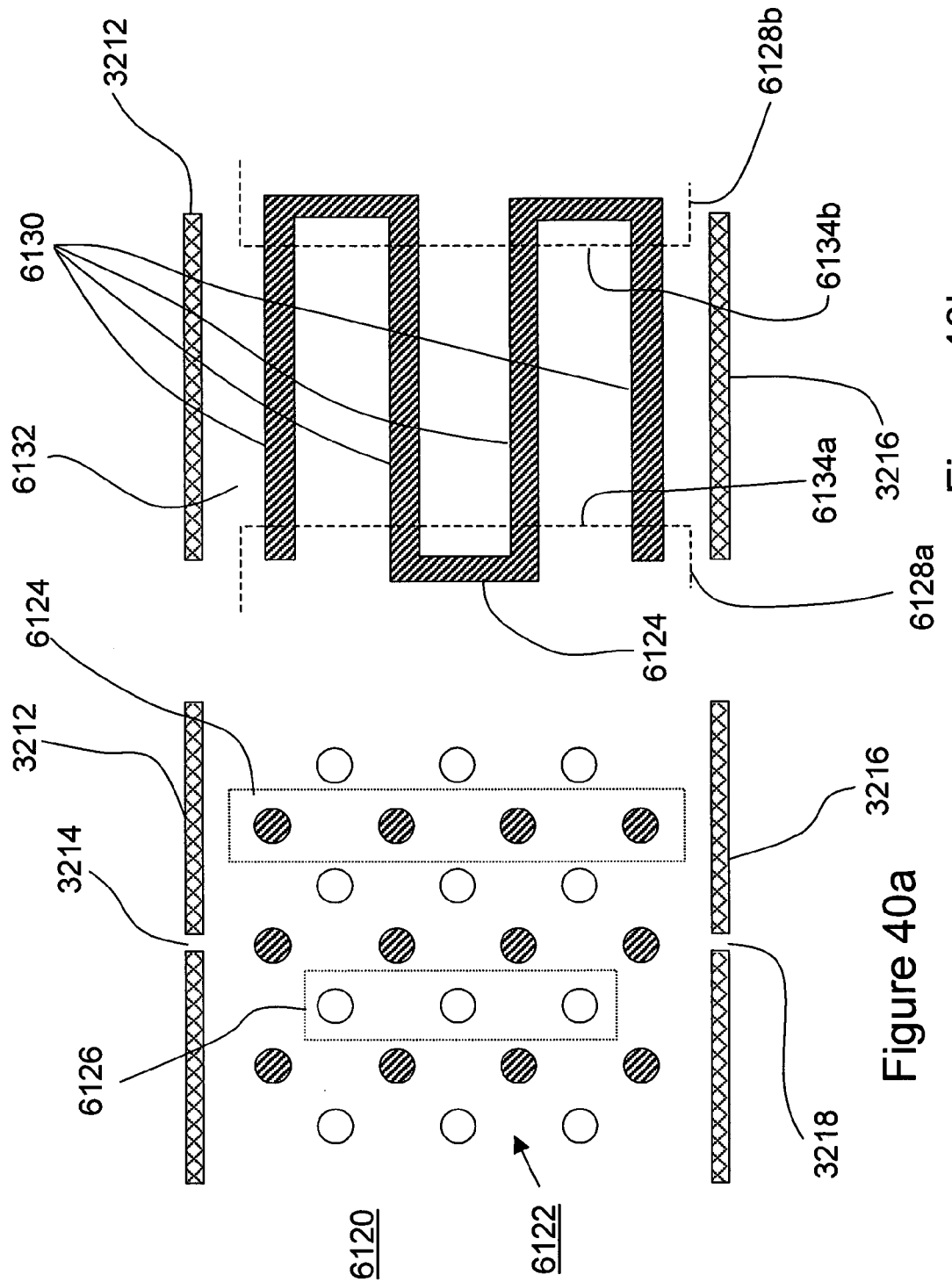
FIG. 40a is a simplified schematic view of a FAIMS analyzer including a formed electrode according to another embodiment of the instant invention, taken along a first direction; and, FIG. 40b is a simplified schematic view of the FAIMS analyzer of FIG. 40a taken along a direction normal to the first direction.

Referring now to FIG. 40a, shown is a simplified schematic view of a FAIMS analyzer including a formed electrode, taken along a first direction. The FAIMS analyzer, shown generally at 6120, includes a not illustrated electrical controller that is connectable to an electrode assembly 6122. The electrode assembly 6122 includes formed electrodes, including a first type of formed electrode 6124 and a second type of formed electrode 6126. In the instant example, the first type of formed electrode 6124 and the second type of formed electrode 6126 are arranged approximately parallel one to the other, in a spaced-apart alternating sequence as shown in FIG. 40a. The first type of formed electrode 6124 and the second type of formed electrode 6126 are embedded within an electrically insulating material (not shown in FIG. 40a). The electrode assembly 6122 is disposed between an ion inlet plate 3212 including an ion inlet 3214, and an ion outlet plate 3216 including an ion outlet 3218.

Referring now to FIG. 40b, shown is a simplified schematic view of the FAIMS analyzer of FIG. 40a taken along a second direction normal to the first direction. For the sake of clarity, only the first type of formed electrode 6124 is shown in FIG. 40b. The first type of formed electrode 6124 is shown embedded within an electrically insulating material 6128a, 6128b, such that a plurality of rod-shaped portions 6130 of the first type of formed electrode 6124 is disposed within a gap 6132 between facing surfaces 6134a, 6134b of the electrically insulating material 6128a, 6128b, respectively. Of course, other combinations of formed electrodes and substantially rod-shaped electrodes may be envisaged by one of skill in the art.

Of course, different configurations of an electrical controller are envisaged as options for providing the asymmetric waveform voltage and the CV. Power sources may be combined in one housing or may be in the form of separately housed components. The electrical controller may include an electronic circuit, for instance to generate the asymmetric waveform, or may be a simple device such as an electrically conducting wire for maintaining an electrode at ground potential. The term electrical controller has been used to denote the means by which a desired voltage is applied and maintained on an electrode. Although the foregoing detailed description of the instant invention describes electrical voltages as being applied to specific electrodes of the various electrode assemblies, for example via electrical contacts carried on the specific electrodes, it is to be understood that the effect is to apply a desired voltage between electrodes so as to establish an electrical field for separating the ions. Of course, the strength of the electric field that is established is dependent upon the voltages that are applied between the electrodes, as well as the distance between the electrodes that are used to establish the fields.

Numerous other embodiments may be envisaged without departing from the spirit and scope of the invention.

What is claimed is:

1. An apparatus for separating ions, comprising:
a FAIMS analyzer region having a first ion inlet for introducing ions into the FAIMS analyzer region and having an ion outlet for extracting a subset of the ions that is selectively transmitted along an average ion flow path defined through the FAIMS analyzer region; and,
a controller for controllably varying a length of an average ion flow path through the FAIMS analyzer region.

2. An apparatus according to claim 1, wherein the controller comprises an actuator.

3. An apparatus according to claim 2, wherein the FAIMS analyzer region has a second ion inlet for introducing ions into the FAIMS analyzer region.

4. An apparatus according to claim 3, wherein a distance between the first ion inlet and the ion outlet defines a first length of an average ion flow path and wherein a distance between the second ion inlet and the ion outlet defines a second length of an average ion flow path.

5. An apparatus according to claim 4, wherein the actuator comprises an ion inlet selector.

6. An apparatus according to claim 5, wherein the ion inlet selector comprises a selector electrode having an opening defined therethrough, the selector electrode moveable between a first position in which the opening is aligned with the first ion inlet for supporting introduction of ions into the FAIMS analyzer region via the first ion inlet and a second position in which the opening is aligned with the second ion inlet for supporting introduction of ions via the second ion inlet.

7. An apparatus according to claim 3, comprising a first electrode and a second electrode disposed in a spaced-apart relationship one relative to the other, a space between the first electrode and the second electrode defining the FAIMS analyzer region.

8. An apparatus according to claim 7, wherein the first ion inlet is defined through a first portion of the first electrode such that ions introduced via the first ion inlet travel a first length along an average ion flow path between the first ion inlet and the ion outlet, and wherein the second ion inlet is defined through a second portion of the first electrode such that ions introduced via the second ion inlet travel a second length along an average ion flow path between the second ion inlet and the ion outlet.

9. An apparatus according to claim 8, wherein the second length is shorter than the first length.

10. An apparatus according to claim 9, wherein the actuator comprises an ion inlet selector.

11. An apparatus according to claim 10, wherein the ion inlet selector comprises a selector electrode having an opening defined therethrough, the selector electrode moveable between a first position in which the opening is aligned with the first ion inlet for supporting introduction of ions into the FAIMS analyzer region via the first ion inlet and a second position in which the opening is aligned with the second ion inlet for supporting introduction of ions via the second ion inlet.

12. An apparatus according to claim 7, comprising an electrical controller for applying an asymmetric waveform voltage and a direct current compensation voltage between the first electrode and the second electrode.

13. An apparatus according to claim 3, comprising a first ionization source disposed adjacent to the first ion inlet for providing a flow of analyte ions produced from a sample material for introduction via the first ion inlet.

14. An apparatus according to claim 13, comprising a second ionization source disposed adjacent to the second ion inlet orifice for providing a flow of ions produced from the sample material for introduction via the second ion inlet.

15. An apparatus according to claim 13, comprising a second ionization source disposed adjacent to the second ion inlet orifice for providing a flow of ions produced from a LockMass calibration compound for introduction via the second ion inlet.

16. An apparatus according to claim 1, wherein the controller comprises an electrical controller.

17. An apparatus according to claim 16, wherein the FAIMS analyzer region comprises:
a plurality of first electrode portions, each first electrode portion of the plurality of first electrode portions having a first length and an outer surface that is at least partially curved in a direction transverse to the first length; and,
a plurality of second electrode portions interleaved in a repeating sequence with the plurality of first electrode portions, each second electrode portion of the plurality of second electrode portions having a second length and an outer surface that is at least partially curved in a direction transverse to the second length, a space between the outer surface of a first electrode portion and the outer surface of an adjacent second electrode portion defining a portion of the FAIMS analyzer region,
wherein the electrical controller is for electrically coupling to at least one of the plurality of first electrode portions and the plurality of second electrode portions, for selectably applying a predetermined asymmetric waveform voltage and direct current voltage between predetermined first and second electrode portions to define a first average ion flow path having a first length, and between different predetermined first and second electrode portions to define a second average ion flow path having a second length that is different than the first length.

18. An apparatus according to claim 17, comprising a second ion inlet into the FAIMS analyzer region, wherein the first average ion flow path is defined between the first ion inlet and the ion outlet, and the second average ion flow path is defined between the second ion inlet and the ion outlet.

19. An apparatus according to claim 17, wherein the first average ion flow path and the second average ion flow path are defined between the first ion inlet and the ion outlet.

20. An apparatus according to claim 19, wherein the plurality of first electrode portions comprises a plurality of first electrode rods, each first electrode rod of the plurality of first electrode rods defining one first electrode portion of the plurality of first electrode portions.

21. An apparatus according to claim 20, wherein the plurality of second electrode portions comprises a plurality of second electrode rods, each second electrode rod of the plurality of second electrode rods defining one second electrode portion of the plurality of second electrode portions.

22. An apparatus according to claim 19, wherein one of the plurality of first electrode portions and the plurality of second electrode portions comprises a formed-electrode.

23. A method for separating ions, comprising:
providing a FAIMS analyzer region having a first ion inlet for introducing ions thereto and having an ion outlet for extracting a subset of the ions that is selectively transmitted along an average ion flow path through the FAIMS analyzer region;
introducing ions into the FAIMS analyzer region via the first ion inlet;
selectively transmitting a subset of the ions through the FAIMS analyzer region along a first length of an average ion flow path;
changing an average ion flow path length through the FAIMS analyzer region; and,
transmitting ions along the second length of an average ion flow path.

24. A method according to claim 23, comprising providing a second ion inlet for introducing ions into the FAIMS analyzer region, wherein a distance between the first ion inlet and the ion outlet defines the first length and wherein a distance between the second ion inlet and the ion outlet defines the second length.

25. A method according to claim 24, wherein changing an average ion flow path length through the FAIMS analyzer region comprises actuating an ion inlet selector between a first orientation in which an opening of the ion inlet selector is aligned with the first ion inlet for supporting ion introduction therethrough, and a second orientation in which the opening of the ion inlet selector is aligned with the second ion inlet for supporting ion introduction therethrough.

26. A method according to claim 23, wherein transmitting ions along the second length of an average ion flow path comprises selectively transmitting a second subset of the ions.

27. A method according to claim 26, wherein an ion composition of the second subset of ions is substantially the same as an ion composition of the subset of ions.

28. A method for separating ions, comprising:
providing a FAIMS analyzer region having an ion inlet end for receiving ions and having an ion outlet for providing a subset of the ions that is selectively transmitted between the ion inlet end and the ion outlet of the FAIMS analyzer region;

defining a first average ion flow path length through the FAIMS analyzer region;

defining a second average ion flow path length through the FAIMS analyzer region, the second average ion flow path length different than the first average ion flow path length; and, controllably switchably providing ions along the first average ion flow path length and the second average ion flow path length.

29. A method according to claim 28, wherein defining the first average ion flow path length comprises providing a first ion inlet within a portion of the ion inlet end, such that the first average ion flow path length is defined between the first ion inlet and the ion outlet.

30. A method according to claim 29, wherein defining the second average ion flow path length comprises providing a second ion inlet within a different portion of the ion inlet end, such that the second average ion flow path length is defined between the second ion inlet and the ion outlet.

31. An apparatus for separating ions, comprising:

a FAIMS analyzer region controllably switchable between a low specificity mode of operation and a high specificity mode of operation and defined by at least a space between a plurality of spaced-apart electrode surfaces, the FAIMS analyzer region in communication with an ionization source for providing a flow of ions including a known ion, and with an ion outlet for extracting ions including the known ion from the FAIMS analyzer region; and, a controller for controllably switching the FAIMS analyzer region between the low specificity mode of operation and the high specificity mode of operation.

* * * * *